United States Patent
Lee et al.

(10) Patent No.: US 10,211,407 B2
(45) Date of Patent: Feb. 19, 2019

(54) CONDENSED CYCLIC COMPOUND AND ORGANIC LIGHT-EMITTING DEVICE INCLUDING THE SAME

(71) Applicant: SAMSUNG DISPLAY CO., LTD., Yongin-si, Gyeonggi-do (KR)

(72) Inventors: Eunyoung Lee, Yongin-si (KR); Youngkook Kim, Yongin-si (KR); Junha Park, Yongin-si (KR); Munki Sim, Yongin-si (KR); Eunjae Jeong, Yongin-si (KR); Seokhwan Hwang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 161 days.

(21) Appl. No.: 14/937,780

(22) Filed: Nov. 10, 2015

(65) Prior Publication Data
US 2016/0276597 A1 Sep. 22, 2016

(30) Foreign Application Priority Data

Mar. 16, 2015 (KR) .................. 10-2015-0036186

(51) Int. Cl.
| | |
|---|---|
| C07D 491/052 | (2006.01) |
| C07F 9/6561 | (2006.01) |
| H01L 51/00 | (2006.01) |
| C09K 11/02 | (2006.01) |
| H01L 51/50 | (2006.01) |

(52) U.S. Cl.
CPC ...... H01L 51/0071 (2013.01); C07D 491/052 (2013.01); C07F 9/6561 (2013.01); C09K 11/025 (2013.01); H01L 51/0058 (2013.01); H01L 51/0067 (2013.01); H01L 51/0072 (2013.01); H01L 51/5012 (2013.01); H01L 51/5072 (2013.01)

(58) Field of Classification Search
CPC ............... C07D 491/052; C09K 11/025; C07F 9/65616; C07F 9/6561; H01L 51/0058; H01L 51/0067; H01L 51/0071; H01L 51/0072
See application file for complete search history.

(56) References Cited

U.S. PATENT DOCUMENTS

| | | |
|---|---|---|
| 5,645,948 A | 7/1997 | Shi et al. |
| 2003/0165715 A1 | 9/2003 | Yoon et al. |
| 2004/0053069 A1 | 3/2004 | Sotoyama et al. |
| 2004/0137270 A1 | 7/2004 | Seo et al. |
| 2007/0131929 A1 | 6/2007 | Bae et al. |
| 2011/0240979 A1* | 10/2011 | Kim .................... C07D 487/04 257/40 |

FOREIGN PATENT DOCUMENTS

| | | | |
|---|---|---|---|
| JP | 10-17860 A | | 1/1998 |
| JP | 11-87067 A | | 3/1999 |
| JP | 11-322756 | * | 11/1999 |
| JP | 4060669 B2 | | 3/2008 |
| KR | 10-0525408 B1 | | 11/2005 |
| KR | 10-0691543 B1 | | 3/2007 |
| KR | 10-2007-0062920 A | | 6/2007 |
| KR | 10-2010-0108924 A | | 10/2010 |
| WO | WO 2010/114264 A2 | | 10/2010 |

OTHER PUBLICATIONS

Dejon, L.; Mohammed, H.;Du, P.; Jacob, C.;Speicher, A.—Synthesis of chromenoindole derivatives from Robinia pseudoacacia, Med. Chem. Commun, 2013, 4, pp. 1580-1583.*

(Continued)

*Primary Examiner* — Anca Eoff
(74) *Attorney, Agent, or Firm* — Lewis Roca Rothgerber Christie LLP

(57) ABSTRACT

An organic light-emitting device includes: a first electrode; a second electrode facing the first electrode; and an organic layer between the first electrode and the second electrode, the organic layer including an emission layer; a hole transport region between the first electrode and the emission layer; and an electron transport region between the emission layer and the second electrode. At least one of the emission layer and the electron transport region includes a condensed cyclic compound represented by one selected from Formulae 1-1 and 1-2:

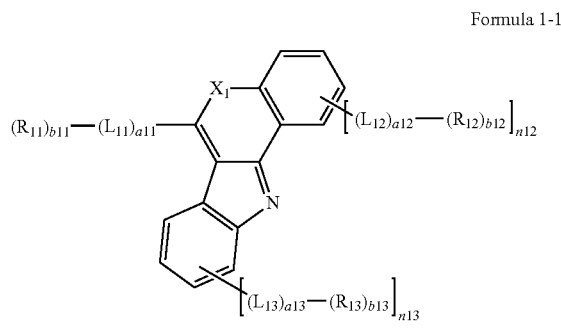

Formula 1-1

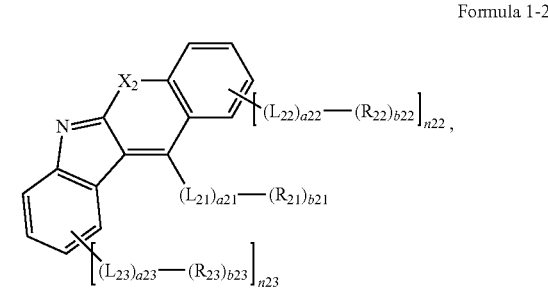

Formula 1-2

The organic light-emitting device including one or more of the condensed cyclic compounds according to embodiments of the present disclosure may have low driving voltage, high efficiency, high luminance, and long lifespan.

20 Claims, 1 Drawing Sheet

(56) References Cited

OTHER PUBLICATIONS

Minozzi, M.; Nanni, D.; Zanardi, G.; Calestani, G.—Multi-step radical spro-cyclization of an alkynylaryl isothiocyanate, ARKIVOC, 2006 (vi), pp. 6-14.*

Clark, P.D.; McKinnon, D.M.—The preparation of some thiochroman-3-ones and derivatives, 1982, Can. J. Chem. vol. 60, 1982, pp. 243-248.*

Graczol-Fordos, E.; Novak, T.; Blasko, G.; Fejes, I.; Perron-Sierra, F.; Nyerges, M.—Synthesis of Chromeno (2,3-b)Indole Derivatives, Heterocycles, vol. 87, No. 10, 2013, pp. 2053-2069 (Year: 2013).*

Machine translation of JP 11-322756, published on Nov. 24, 1999 (Year: 1999).*

O'Shea, D. et al.—Exploration of the structure-activity relationship of a novel tetracyclic class of TSPO ligands—Potential novel positron emitting tomography imaging agents, Bioorganic & Medicinal Chemistry Letters 23 (2013), pp. 2368-2372 (Year: 2013).*

Adachi, Chihaya et al., "Confinement of charge carriers and molecular excitons within 5-nm-thick emitter layer in organic electroluminescent devices with a double heterostructure", Applied Physics Letters, Aug. 6, 1990, pp. 531-533, vol. 57, No. 6.

Johansson, Nicklas et al., "Solid-State Amplified Spontaneous Emission in Some Spiro-Type Molecules: A New Concept for the Design of Solid-State Lasing Molecules", Advanced Materials, 1998, pp. 1136-1141, vol. 10, No. 14.

Nanjo, Takeshi et al., "Synthesis of 3-Acyl-2-arylindole via Palladium-catalyzed Isocyanide Insertion and Oxypalladation of Alkyne", Organic Letters, Mar. 7, 2013, pp. 3754-3757, vol. 15, No. 14.

Peng, Wei et al., "Synthesis and in vitro antiproliferative activity of new 11-aminoalkylamino-substituted chromeno[2,3-b]indoles", European Journal of Medicinal Chemistry, Oct. 24, 2012, pp. 441-451, vol. 58.

Sakamoto, Youichi et al., "Synthesis, Characterization, and Electron-Transport Property of Perfluorinated Phenylene Dendrimers", Journal for the American Chemical Society, Feb. 15, 2000, pp. 1832-1833, vol. 122, No. 8.

Tang, C.W. et al., "Organic electroluminescent diodes", Applied Physics Letters, Sep. 21, 1987, pp. 913-915, vol. 51, No. 12.

Tao, Y.T. et al., "Sharp green electroluminescence from 1H-pyrazolo[3,4-b]quinoline-based light-emitting diodes", Applied Physics Letters, Sep. 11, 2000, pp. 1575-1577, vol. 77, No. 11.

Website: "Chromeno[4,3-b]indole", ChemSpider, http://www.chemspider.com/Chemical-Structure.10635577.html?rid=ca372b1b-7685-4ad3-8dca-d34d2b6a572f, 1 page.

Yamaguchi, Shigehiro et al., "Diphenylamino-Substituted 2,5-Diarylsiloles for Single-Layer Organic Electroluminescent Devices", Chemistry Letters, 2001, pp. 98-99.

* cited by examiner

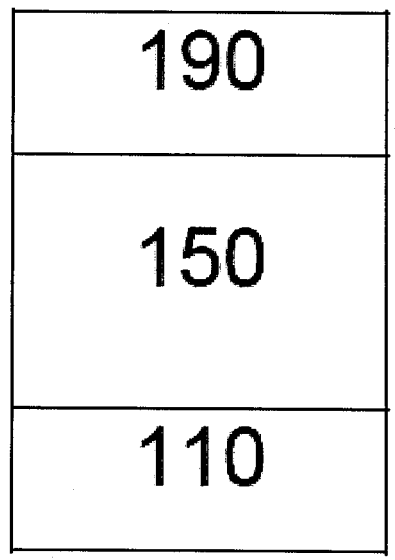

CONDENSED CYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2015-0036186, filed on Mar. 16, 2015, in the Korean Intellectual Property Office, the entire disclosure of which is incorporated herein by reference.

BACKGROUND

1. Field

One or more aspects of embodiments of the present disclosure relate to a condensed cyclic compound and an organic light-emitting device including the same.

2. Description of the Related Art

Organic light emitting devices are self-emission devices that have wide viewing angles, high contrast ratios, short response times, and excellent brightness, driving voltage, and response speed characteristics, and can produce full-color images.

An organic light-emitting device may include a first electrode positioned on a substrate, and a hole transport region, an emission layer, an electron transport region, and a second electrode, which are sequentially positioned on the first electrode. Holes provided from the first electrode may move toward the emission layer through the hole transport region, and electrons provided from the second electrode may move toward the emission layer through the electron transport region. Carriers (e.g., holes and electrons) are then recombined in the emission layer to produce excitons. These excitons change from an excited state to a ground state, thereby generating light.

SUMMARY

One or more aspects of embodiments of the present disclosure relate to a novel condensed cyclic compound and an organic light-emitting device including the same.

Additional aspects will be set forth in part in the description which follows and, in part, will be apparent from the description, or may be learned by practice of the presented embodiments.

According to an embodiment of the present disclosure, a condensed cyclic compound represented by one selected from Formulae 1-1 and 1-2 is provided:

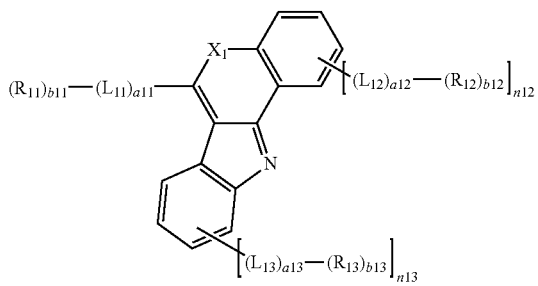

Formula 1-1

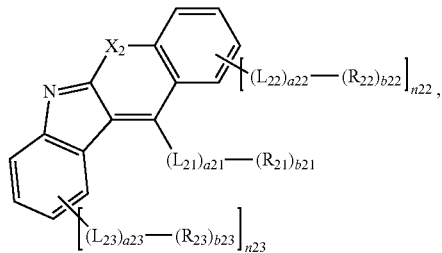

Formula 1-2 wherein in Formulae 1-1 and 1-2, $X_1$ and $X_2$ may be each independently O or S;

$L_{11}$ to $L_{13}$ and $L_{21}$ to $L_{23}$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a11 to a13 and a21 to a23 may be each independently selected from 0, 1, 2 and 3, and when a11 is 2 or more, 2 or more $L_{11}$(s) may be identical to or different from each other, and when a12 is 2 or more, 2 or more $L_{12}$(s) may be identical to or different from each other, and when a13 is 2 or more, 2 or more $L_{13}$(s) may be identical to or different from each other, and when a21 is 2 or more, 2 or more $L_{21}$(s) may be identical to or different from each other, and when a22 is 2 or more, 2 or more $L_{22}$(s) may be identical to or different from each other, and when a23 is 2 or more, 2 or more $L_{23}$(s) may be identical to or different from each other;

$R_{11}$ to $R_{13}$ and $R_{21}$ to $R_{23}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —P(=O)($Q_4$)($Q_5$), —S(=O)($Q_6$), and —S(=O)$_2$($Q_7$);

b11 to b13 and b21 to b23 may be each independently selected from 0, 1, 2, and 3, and when b11 is 2 or more, 2 or more $R_{11}$(s) may be identical to or different from each other, and when b12 is 2 or more, 2 or more $R_{12}$(s) may be identical to or different from each other, and when b13 is 2 or more, 2 or more $R_{13}$(s) may be identical to or different from each other, and when b21 is 2 or more, 2 or more $R_{21}$(s)

may be identical to or different from each other, and when b22 is 2 or more, 2 or more $R_{22}$(s) may be identical to or different from each other, b23 is 2 or more, 2 or more $R_{23}$(s) may be identical to or different from each other; and n12, n13, n22 and n23 may be each independently selected from 0, 1, 2, 3, and 4.

The compound represented by Formula 1-1 is neither Compound A nor Compound B, and the compound represented by Formula 1-2 is not Compound D:

Compound A

Compound B

Compound D

At least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —B($Q_{14}$)($Q_{15}$), and —N($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —B($Q_{24}$)($Q_{25}$) and —N($Q_{26}$)($Q_{27}$); and —Si($Q_{31}$)($Q_{32}$)($Q_{33}$), —B($Q_{34}$)($Q_{35}$), and —N($Q_{36}$)($Q_{37}$), wherein $Q_1$ to $Q_7$, $Q_{11}$ to $Q_{17}$, $Q_{21}$ to $Q_{27}$ and $Q_{31}$ to $Q_{37}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to another embodiment of the present disclosure, provided is an organic light-emitting device including: a first electrode; a second electrode facing the first electrode; and an organic layer between the first electrode and the second electrode, the organic layer including an emission layer, and at least one selected from the condensed cyclic compounds described above.

BRIEF DESCRIPTION OF THE DRAWINGS

These and/or other aspects will become apparent and more readily appreciated from the following description of the embodiments, taken in conjunction with the drawing.

The drawing is a schematic view of an organic light-emitting device according to one or more example embodiments.

DETAILED DESCRIPTION

Reference will now be made in more detail to embodiments, examples of which are illustrated in the accompanying drawing, wherein like reference numerals refer to the like elements throughout. In this regard, the present embodiments may have different forms and should not be construed as being limited to the descriptions set forth herein. Accordingly, the embodiments are merely described below, by referring to the drawing, to explain aspects of the present description. As used herein, the term "and/or" includes any and all combinations of one or more of the associated listed items. Expressions such as "at least one selected from" and "one selected from," when preceding a list of elements, modify the entire list of elements and do not modify the individual elements of the list. Further, the use of "may" when describing embodiments of the present disclosure refers to "one or more embodiments of the present disclosure."

A condensed cyclic compound according to some embodiments may be represented by one selected from Formulae 1-1 and 1-2:

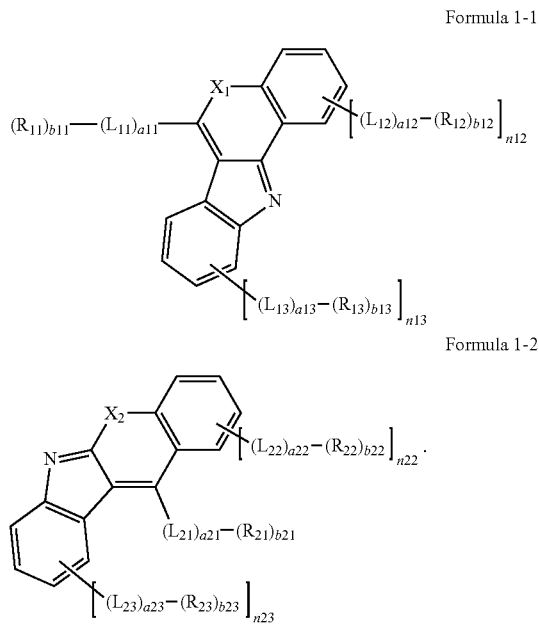

Formula 1-1

Formula 1-2

In Formulae 1-1 and 1-2, $X_1$ and $X_2$ may be each independently O or S.

$L_{11}$ to $L_{13}$ and $L_{21}$ to $L_{23}$ in Formulae 1-1 and 1-2 may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

For example, $L_{11}$ to $L_{13}$ and $L_{21}$ to $L_{23}$ in Formulae 1-1 and 1-2 may be each independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

In some embodiments, $L_{11}$ to $L_{13}$ and $L_{21}$ to $L_{23}$ in Formulae 1-1 and 1-2 may be each independently represented by one selected from Formulae 3-1 to 3-25, but $L_{11}$ to $L_{13}$ and $L_{21}$ to $L_{23}$ are not limited thereto:

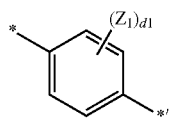

Formula 3-1

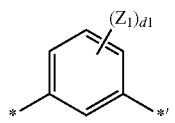

Formula 3-2

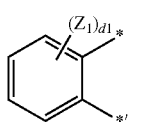

Formula 3-3

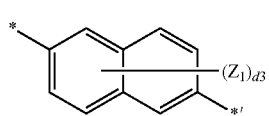

Formula 3-4

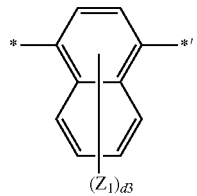

Formula 3-5

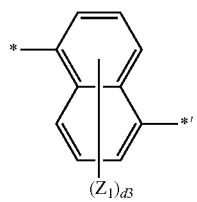

Formula 3-6

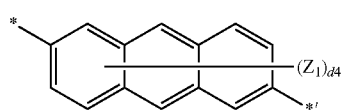

Formula 3-7

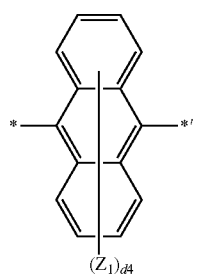

Formula 3-8

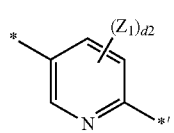

Formula 3-9

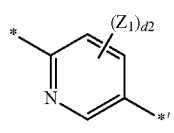

Formula 3-10

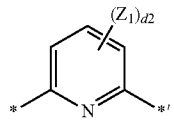

Formula 3-11

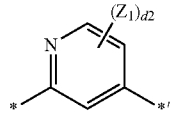

Formula 3-12

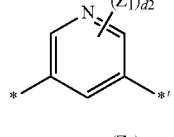

Formula 3-13

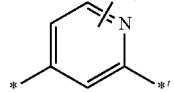

Formula 3-14

Formula 3-15
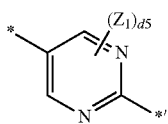

Formula 3-16
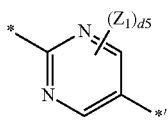

Formula 3-17
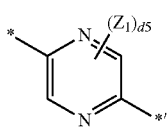

Formula 3-18
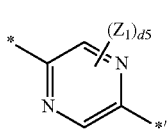

Formula 3-19
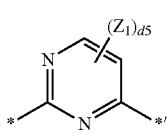

Formula 3-20
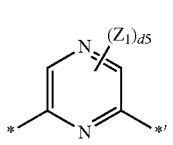

Formula 3-21
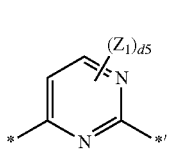

Formula 3-22
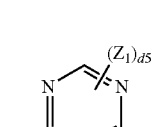

Formula 3-23
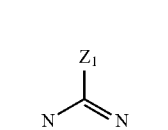

Formula 3-24
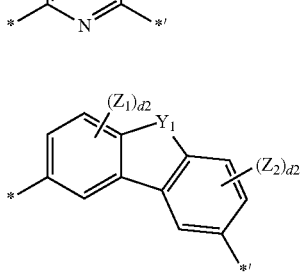

Formula 3-25
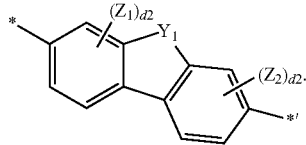

In Formulae 3-1 to 3-25, $Y_1$ may be selected from O, S, $C(Z_3)(Z_4)$ and $N(Z_5)$;

$Z_1$ to $Z_5$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, d1 may be an integer selected from 1 to 4, d2 may be an integer selected from 1 to 3, d3 may be an integer selected from 1 to 6, d4 may be an integer selected from 1 to 8, d5 may be an integer selected from 1 or 2, and * and *' may each be a binding site to a neighboring atom.

In some embodiments, $L_{11}$ to $L_{13}$ and $L_{21}$ to $L_{23}$ in Formulae 1-1 and 1-2 may be each independently represented by one selected from Formulae 4-1 to 4-8, but are not limited thereto:

Formula 4-1
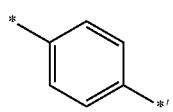

Formula 4-2
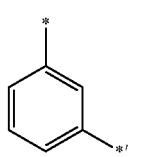

Formula 4-3
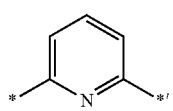

Formula 4-4
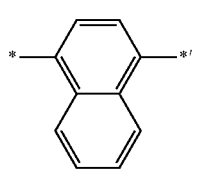

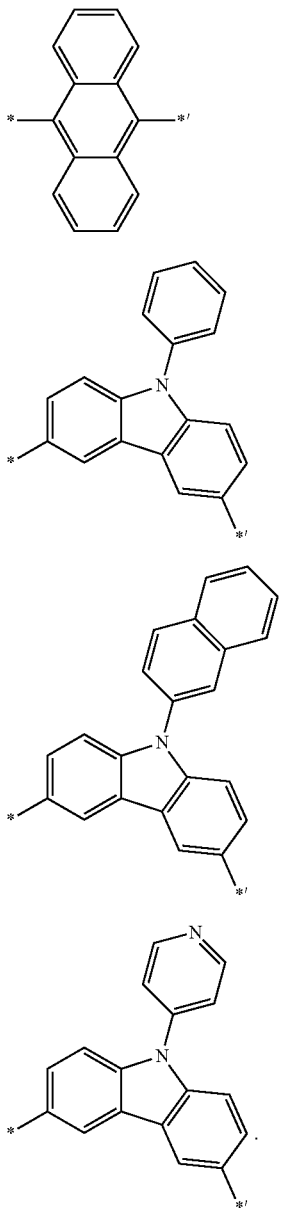

Formula 4-5

Formula 4-6

Formula 4-7

Formula 4-8

* and *' in Formulae 4-1 and 4-8 may each be a binding site to a neighboring atom.

In some embodiments, a11 in Formulae 1-1 and 1-2 indicates the number of $L_{11}$(s), and may be selected from 0, 1, 2, and 3. When a11 is 0, *-$(L_{11})_{a11}$-*' is a single bond. When a11 is 2 or more, 2 or more $L_{11}$(s) may be identical to or different from each other. Descriptions of a11, a12, a13, and a21 to a23 in Formulae 1-1 and 1-2 may be understood by referring to the description of a11 and the structures of Formulae 1-1 and 1-2.

In some embodiments, a11 and a21 in Formulae 1-1 and 1-2 may be each independently selected from 0, 1, and 2, and a12, a13, a22, and a23 may be each independently 0 or 1, but embodiments of the present disclosure are not limited thereto.

In some embodiments, a11 and a21 in Formulae 1-1 and 1-2 may be each independently selected from 0, 1, and 2, and a12, a13, a22, and a23 may each be 0, but embodiments of the present disclosure are not limited thereto.

$R_{11}$ to $R_{13}$ and $R_{21}$ to $R_{23}$ in Formulae 1-1 and 1-2 may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —P(=O)($Q_4$)($Q_5$), —S(=O)($Q_6$), and —S(=O)$_2$($Q_7$).

In some embodiments, $R_{11}$ to $R_{13}$ and $R_{21}$ to $R_{23}$ in Formulae 1-1 and 1-2 may be each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthrolinyl group, a phenanthridinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dinaphthofuranyl group, a dinaphthothiophenyl group, a benzocarbazolyl group, a dibenzocarbazolyl group, an imidazopyridinyl group and an imidazopyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthrolinyl group, a phenanthridinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dinaphthofuranyl group, a dinaphthothiophenyl group, a benzocarbazolyl group, a dibenzocarbazolyl group, an imidazopyridinyl group and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthrolinyl group, a phenanthridinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dinaphthofuranyl group, a dinaphthothiophenyl group, a benzocarbazolyl group, a dibenzocarbazolyl group, an imidazopyridinyl group, an imidazopyrimidinyl group, and —Si($Q_{31}$)($Q_{32}$)($Q_{33}$); and —Si($Q_1$)($Q_2$)($Q_3$), —P(=O)($Q_4$)($Q_5$), —S(=O)($Q_6$) and —S(=O)$_2$($Q_7$), where $Q_1$ to $Q_7$ and $Q_{31}$ to $Q_{33}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a carbazolyl group.

In some embodiments, $R_{11}$ and $R_{21}$ in Formulae 1-1 and 1-2 may be each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a phenanthrolinyl group, a phenanthridinyl group, a benzofuranyl group, a benzothiophenyl group, a dibenzofuranyl group, a dibenzothiophenyl group, a dinaphthofuranyl group, a dinaphthothiophenyl group, a triazinyl group, a benzocarbazolyl group, and a dibenzocarbazolyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a phenanthrolinyl group, a phenanthridinyl group, a benzofuranyl group, a benzothiophenyl group, a dibenzofuranyl group, a dibenzothiophenyl group, a dinaphthofuranyl group, a dinaphthothiophenyl group, a triazinyl group, a benzocarbazolyl group, and a dibenzocarbazolyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a benzofuranyl group, a benzothiophenyl group, a triazinyl group, a benzocarbazolyl group, a dibenzocarbazolyl group, and —Si($Q_{31}$)($Q_{32}$)($Q_{33}$); and —Si($Q_1$)($Q_2$)($Q_3$), —P(=O)($Q_4$)($Q_5$), —S(=O)($Q_6$), and —S(=O)$_2$($Q_7$), where $Q_1$ to $Q_7$ and $Q_{31}$ to $Q_{33}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

In some embodiments, $R_{11}$ and $R_{21}$ in Formulae 1-1 and 1-2 may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, and groups represented by one selected from Formulae 5-1 to 5-44, but embodiments of the present disclosure are not limited thereto:

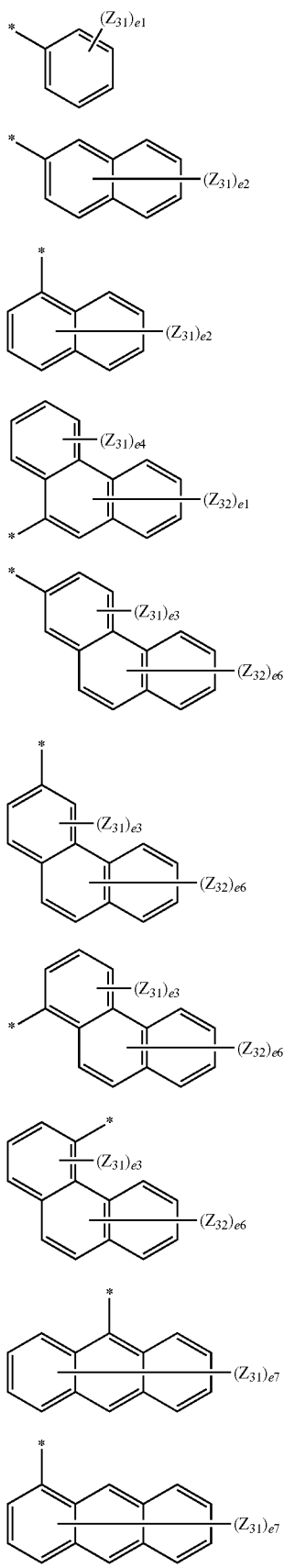
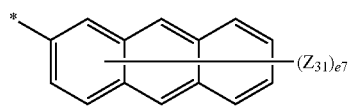
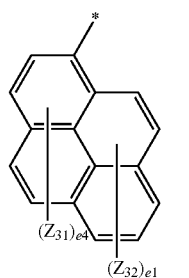
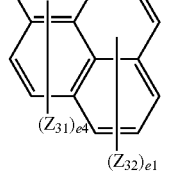
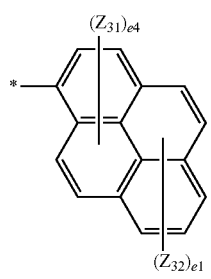
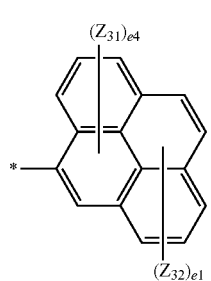
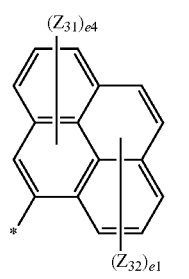
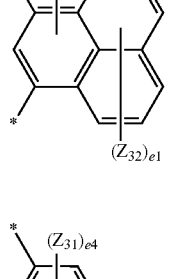
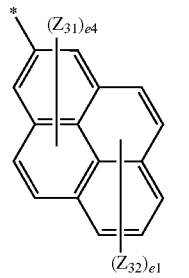

-continued
Formula 5-17
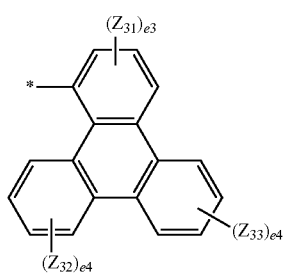
Formula 5-18
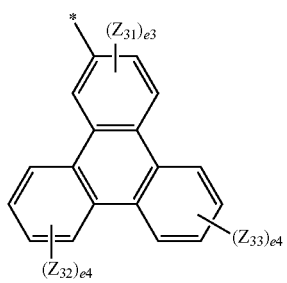
Formula 5-19
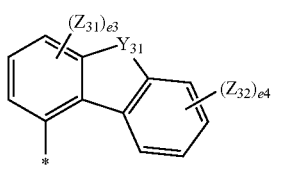
Formula 5-20
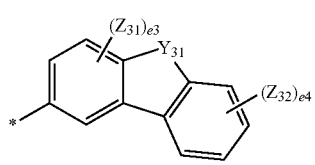
Formula 5-21
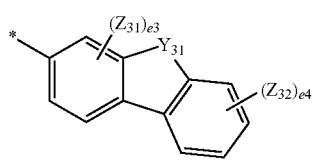
Formula 5-22
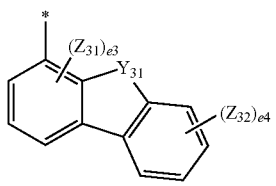
Formula 5-23
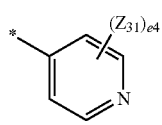
Formula 5-24
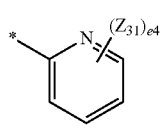
Formula 5-25
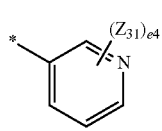
-continued
Formula 5-26
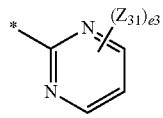
Formula 5-27
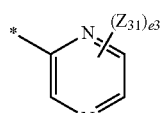
Formula 5-28
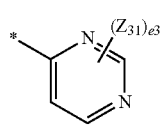
Formula 5-29
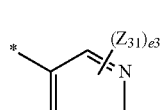
Formula 5-30
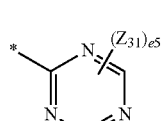
Formula 5-31
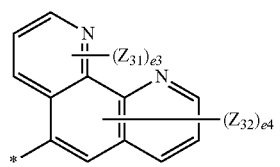
Formula 5-32
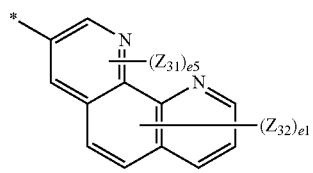
Formula 5-33
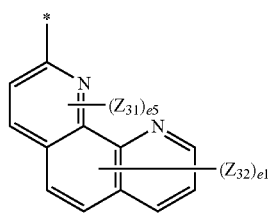
Formula 5-34
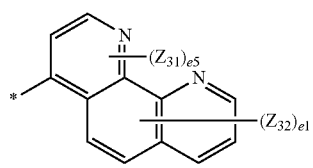
Formula 5-35
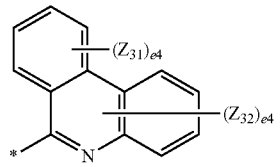

-continued

Formula 5-36

Formula 5-37

Formula 5-38

Formula 5-39

Formula 5-40

Formula 5-41

Formula 5-42

Formula 5-43

Formula 5-44

In Formulae 5-1 to 5-44, $Y_{31}$ is selected from O, S, $C(Z_{34})(Z_{35})$, and $N(Z_{36})$;

$Z_{31}$ to $Z_{36}$ may be each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, a dibenzocarbazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, a dibenzocarbazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group and a naphthyl group; and —Si($Q_{31}$)($Q_{32}$)($Q_{33}$), where $Q_4$ to $Q_7$ and $Q_{31}$ to $Q_{33}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a carbazolyl group;

e1 may be an integer selected from 1 to 5, e2 may be an integer selected from 1 to 7, e3 may be an integer selected from 1 to 3, e4 may be an integer selected from 1 to 4, e5 may be an integer selected from 1 and 2, e6 may be an integer selected from 1 to 6, e7 may be an integer selected from 1 to 9, and * may be a binding site to a neighboring atom.

For example, $Z_{31}$ to $Z_{36}$ in Formulae 5-1 to 5-44 may be each independently selected from hydrogen, deuterium, —F, —Cl, —Br, —I, a hydroxyl group, a cyano group, a nitro group, an amino group, an amidino group, a hydrazine group, a hydrazone group, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, a dibenzocarbazolyl group, a pyridinyl group, a pyrazinyl group, a pyrimidinyl group, and a pyridazinyl group.

In some embodiments, $R_{11}$ and $R_{21}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, and a group represented by one selected from Formulae 6-1 to 6-42, but embodiments of the present disclosure are not limited thereto:

Formula 6-1

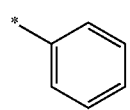

Formula 6-2

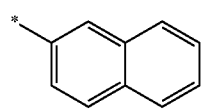

Formula 6-3

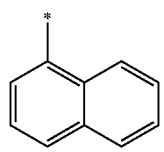

Formula 6-4

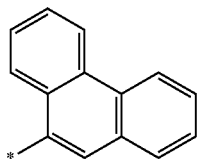

Formula 6-5

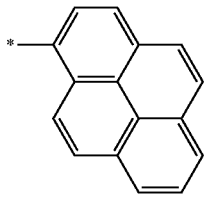

Formula 6-6

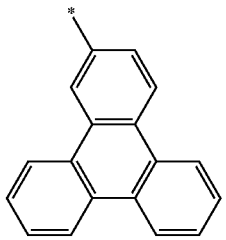

Formula 6-7

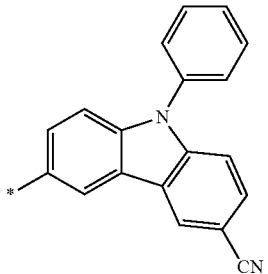

Formula 6-8

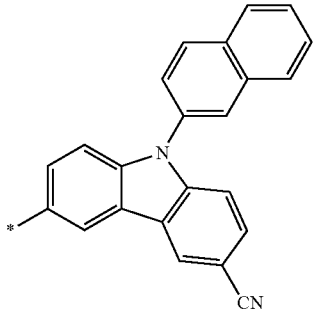

Formula 6-9

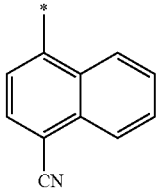

Formula 6-10

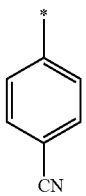

Formula 6-11
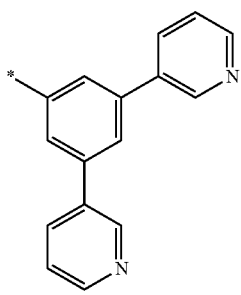
Formula 6-12
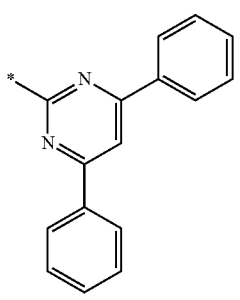
Formula 6-13
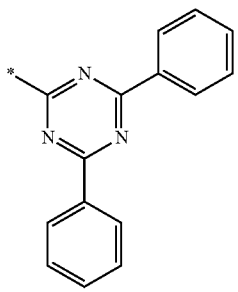
Formula 6-14
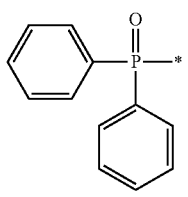
Formula 6-15
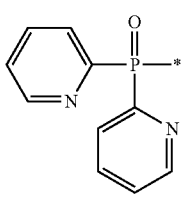
Formula 6-16
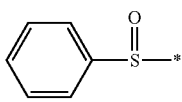
Formula 6-17
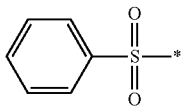
Formula 6-18
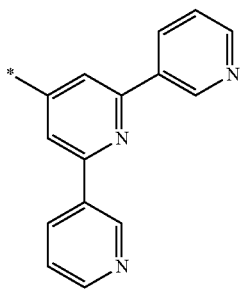
Formula 6-19
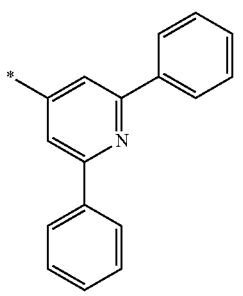
Formula 6-20
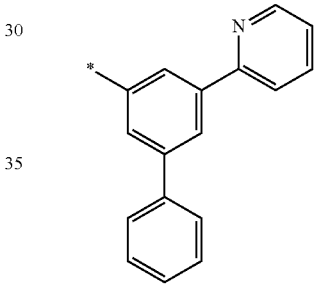
Formula 6-21
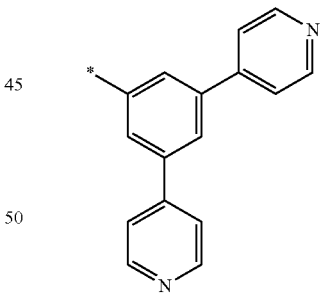
Formula 6-22
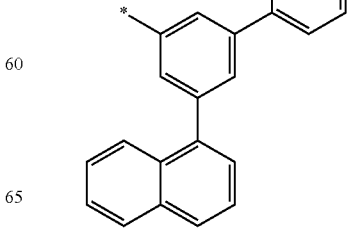

-continued
Formula 6-23
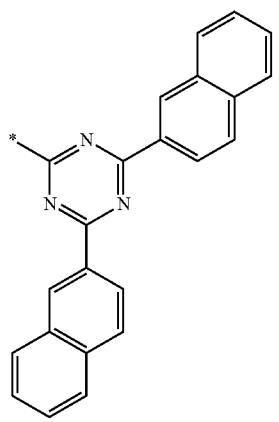
Formula 6-24
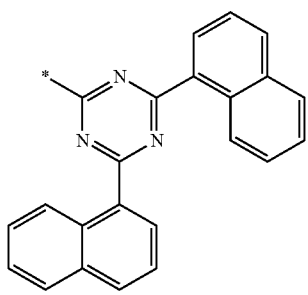
Formula 6-25
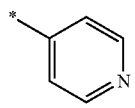
Formula 6-26
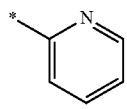
Formula 6-27
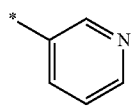
Formula 6-28
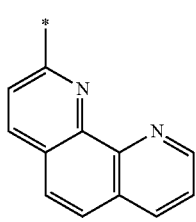
Formula 6-29
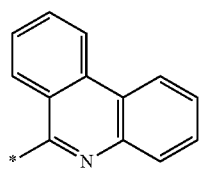
Formula 6-30
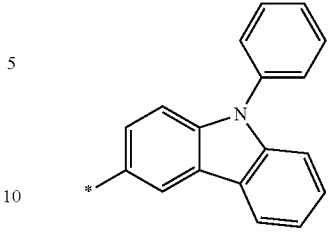
Formula 6-31
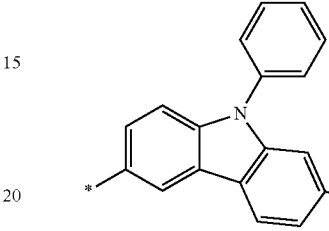
Formula 6-32
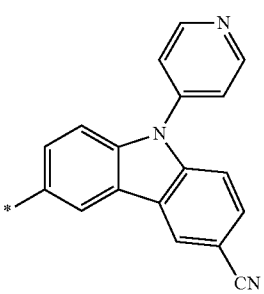
Formula 6-33
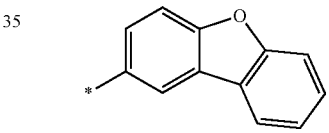
Formula 6-34
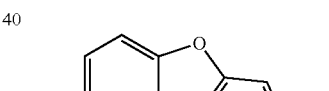
Formula 6-35
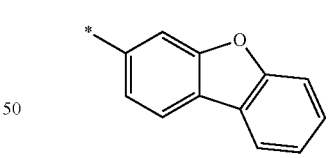
Formula 6-36
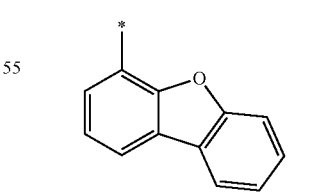
Formula 6-37
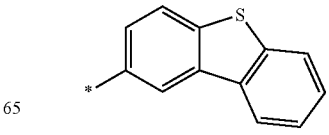

-continued

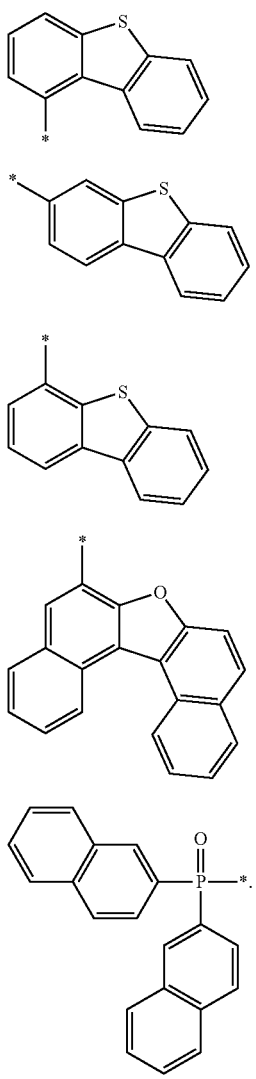

Formula 6-38

Formula 6-39

Formula 6-40

Formula 6-41

Formula 6-42

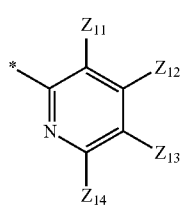

In Formulae 6-1 to 6-42, * may be a binding site to a neighboring atom.

In Formulae 1-1 and 1-2, $R_{12}$, $R_{13}$, $R_{22}$, and $R_{23}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, and groups represented by Formulae 7-1 to 7-44, but embodiments of the present disclosure are not limited thereto:

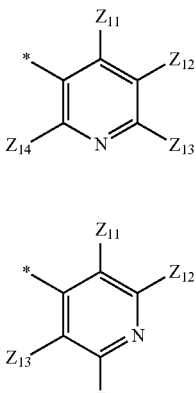

Formula 7-1

Formula 7-2

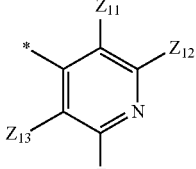

Formula 7-3

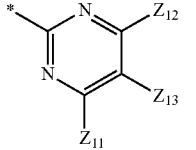

Formula 7-4

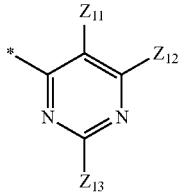

Formula 7-5

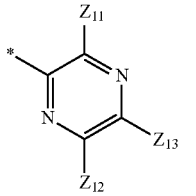

Formula 7-6

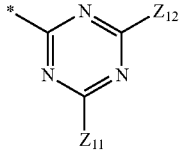

Formula 7-7

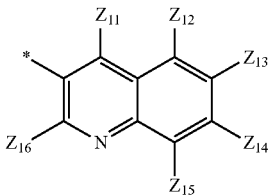

Formula 7-8

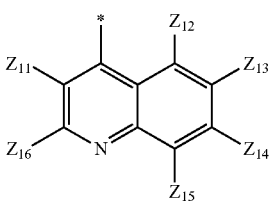

Formula 7-9

-continued
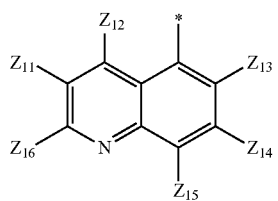
Formula 7-10
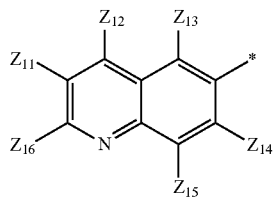
Formula 7-11
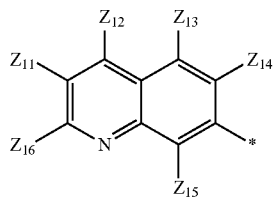
Formula 7-12
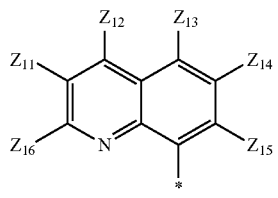
Formula 7-13
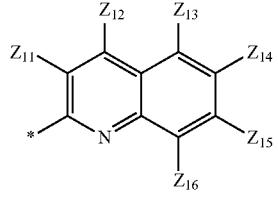
Formula 7-14
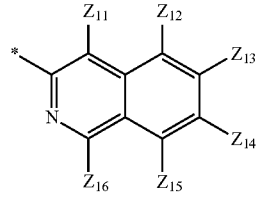
Formula 7-15
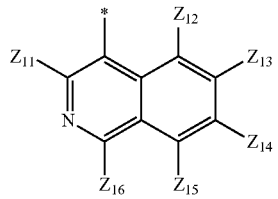
Formula 7-16
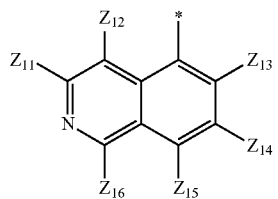
Formula 7-17
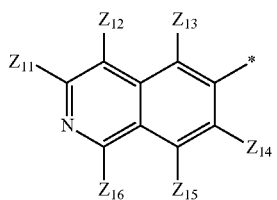
Formula 7-18
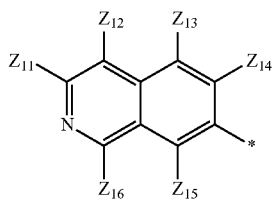
Formula 7-19
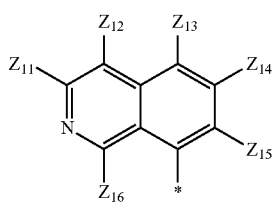
Formula 7-20
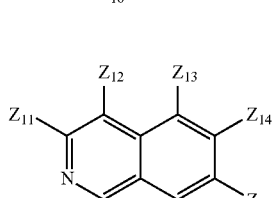
Formula 7-21
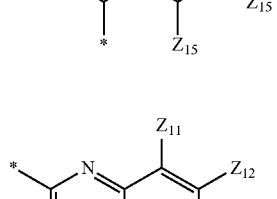
Formula 7-22
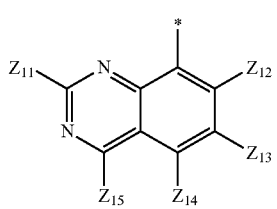
Formula 7-23
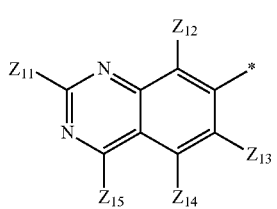
Formula 7-24

-continued
Formula 7-25
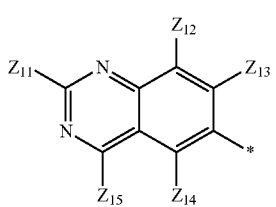
Formula 7-26
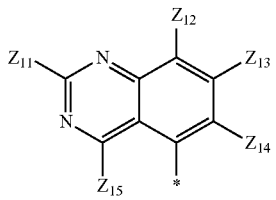
Formula 7-27
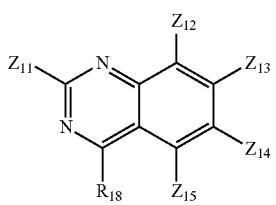
Formula 7-28
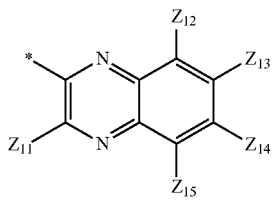
Formula 7-29
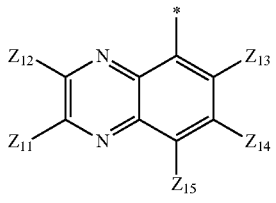
Formula 7-30
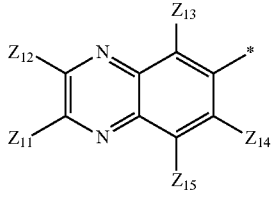
Formula 7-31
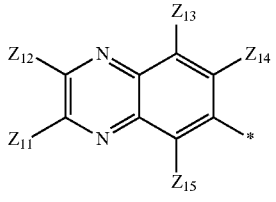
Formula 7-32
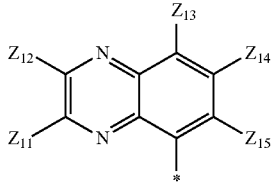
Formula 7-33
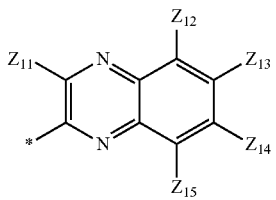
Formula 7-34
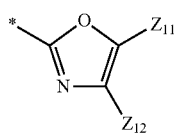
Formula 7-35
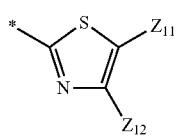
Formula 7-36
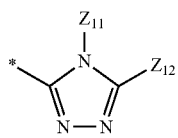
Formula 7-37
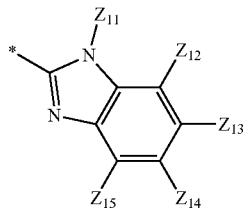
Formula 7-38
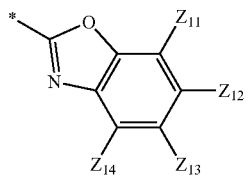
Formula 7-39
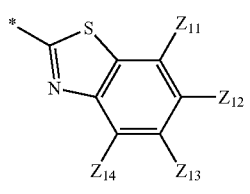
Formula 7-40
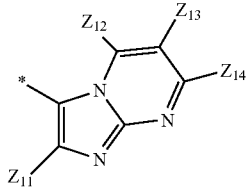
Formula 7-41
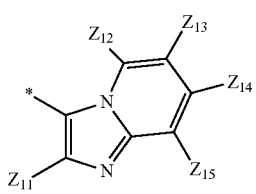

Formula 7-42

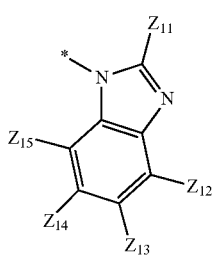

Formula 7-43

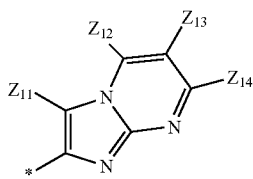

Formula 7-44

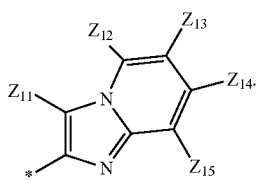

$Z_{11}$ to $Z_{16}$ in Formulae 7-1 to 7-44 may be each independently selected from hydrogen, deuterium, —F, —Cl, —Br, —I, a hydroxyl group, a cyano group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, phenanthridinyl, acridinyl, phenanthrolinyl, phenazinyl, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group and an imidazopyrimidinyl group, and * may be a binding site to a neighboring atom.

For example, $R_{12}$, $R_{13}$, $R_{22}$, and $R_{23}$ in Formulae 1-1 and 1-2 may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a triazolyl group, and a triazinyl group.

In some embodiments, b11 in Formulae 1-1 and 1-2 indicates the number of $R_{11}$(s), and may be 0, 1, 2, and 3. For example, b11 may be 0, 1, and 2. In some embodiments, b1 may be 0 or 1. When b11 is 2 or more, 2 or more $R_{11}$(s) may be identical to or different from each other. Descriptions of b12, b13, and b21 to b23 may be understood by referring to the description of b11 and the structures of Formulae 1-1 and 1-2.

In some embodiments, n12 in Formula 1-1 indicates the number of *-[$(L_{12})_{a12}$-$(R_{12})_{b12}$] and may be selected from 0, 1, 2, and 3. For example, n12 may be 0 or 1. In some embodiments, n12 may be 1. When n12 is 2 or more, 2 or more *-[$(L_{12})_{a12}$-$(R_{12})_{b12}$](s) may be identical to or different from each other.

n13 in Formula 1-1 indicates the number of *-[$(L_{13})_{a13}$-$(R_{13})_{b13}$], and may be selected from 0, 1, 2, and 3. For example, n13 may be 0 or 1. In some embodiments, n13 may be 1. When n13 is 2 or more, 2 or more *-[$(L_{13})_{a13}$-$(R_{13})_{b13}$](s) may be identical to or different from each other.

n22 in Formula 1-2 indicates the number of *-[$(L_{22})_{a22}$-$(R_{22})_{b22}$] and may be selected from 0, 1, 2, and 3. For example, n22 may be 0 or 1. In some embodiments, n22 may be 1. When n22 is 2 or more, 2 or more *-[$(L_{22})_{a22}$-$(R_{22})_{b22}$](s) may be identical to or different from each other.

n23 in Formula 1-2 indicates the number of *-[$(L_{23})_{a23}$-$(R_{23})_{b23}$] and may be selected from 0, 1, 2, and 3. For example, n23 may be 0 or 1. In some embodiments, n23 may be 1. When n23 is 2 or more, 2 or more *-[$(L_{23})_{a23}$-$(R_{23})_{b23}$](s) may be identical to or different from each other.

In some embodiments, the condensed cyclic compound of embodiments of the present disclosure may be represented by one selected from Formulae 1-1A and 1-1B, but the structure thereof is not limited thereto:

Formula 1-1A

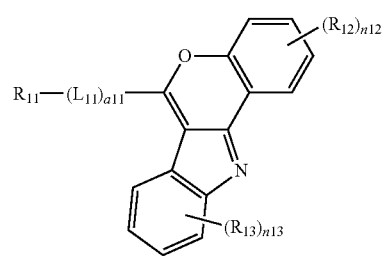

Formula 1-1B

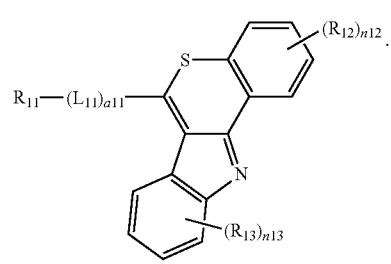

Descriptions of $L_{11}$, a11, $R_{11}$ to $R_{13}$, n12 and n13 in Formulae 1-1A and 1-1B are the same as described herein.

In some embodiments, the condensed cyclic compound may be represented by one selected from Formulae 1-1C and 1-1D, but the structure thereof is not limited thereto:

Formula 1-1C

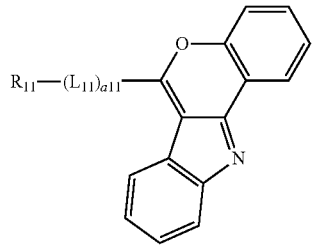

Formula 1-1D

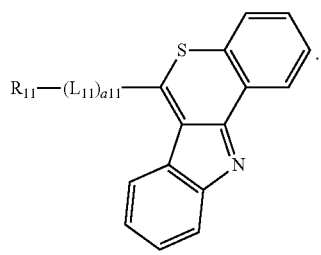

In Formulae 1-1C and 1-1D, $L_{11}$ may be represented by one selected from Formulae 4-1 to 4-8:

Formula 4-1

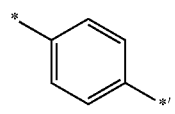

Formula 4-2

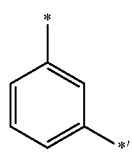

Formula 4-3

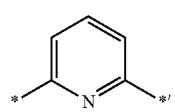

Formula 4-4

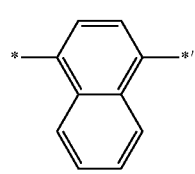

Formula 4-5

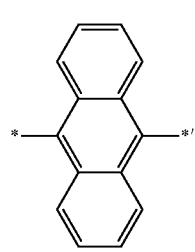

Formula 4-6

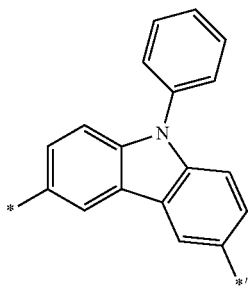

Formula 4-7

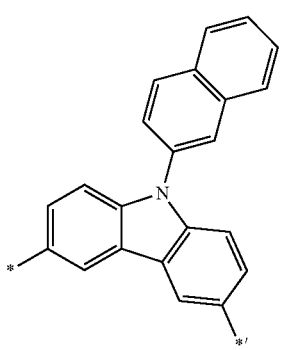

Formula 4-8

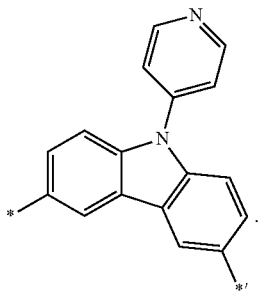

a11 may be selected from 0, 1, and 2, and when a11 is 2, 2 $L_{11}$(s) may be identical to or different from each other; and $R_{11}$ may be represented by one selected from Formulae 6-1 to 6-42:

Formula 6-1

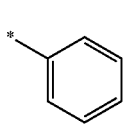

Formula 6-2

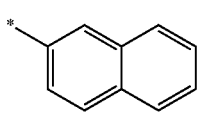

Formula 6-3

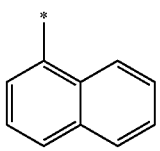

-continued
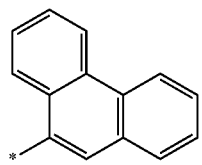
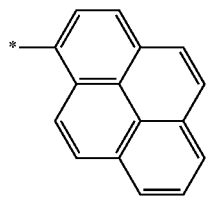
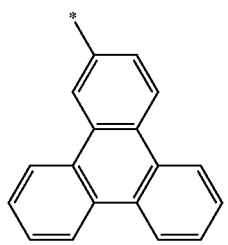
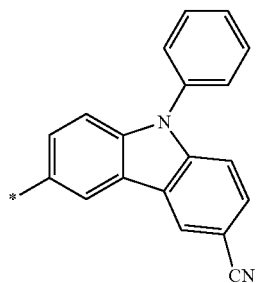
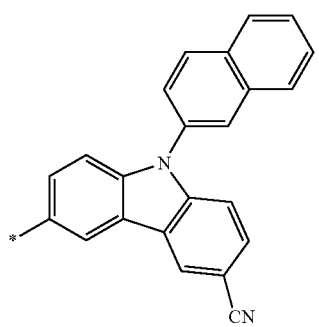
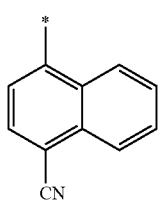
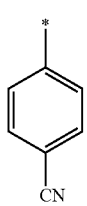
-continued
Formula 6-11
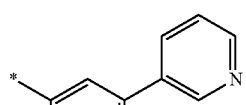
Formula 6-12
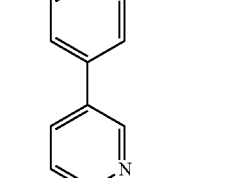
Formula 6-13
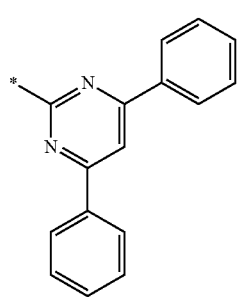
Formula 6-14
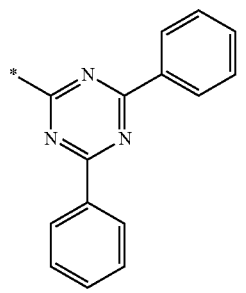
Formula 6-15
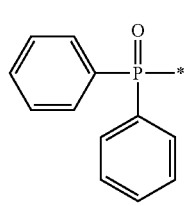
Formula 6-16
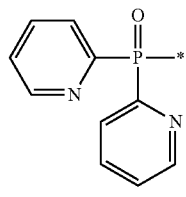
Formula 6-17
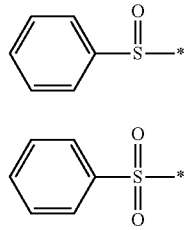
Formula 6-4
Formula 6-5
Formula 6-6
Formula 6-7
Formula 6-8
Formula 6-9
Formula 6-10

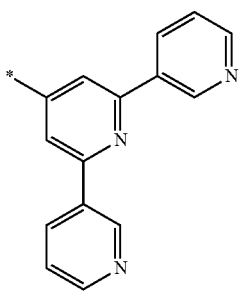
Formula 6-18
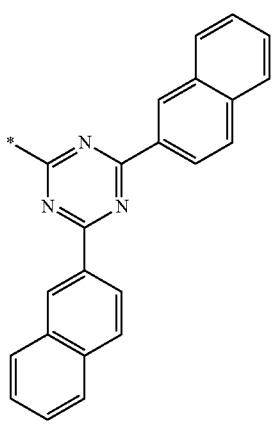
Formula 6-23
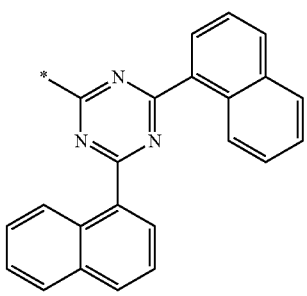
Formula 6-24
Formula 6-19
Formula 6-20
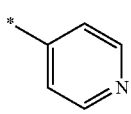
Formula 6-25
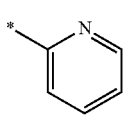
Formula 6-26
Formula 6-21
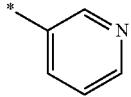
Formula 6-27
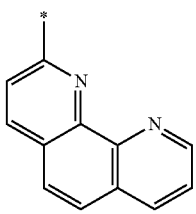
Formula 6-28
Formula 6-22
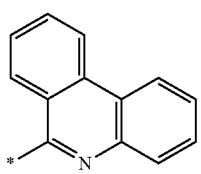
Formula 6-29

-continued
Formula 6-30
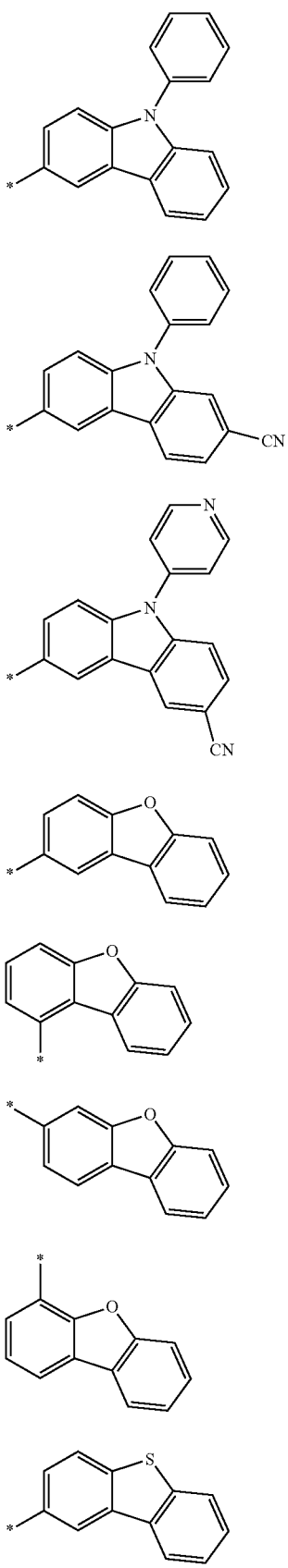
Formula 6-31
Formula 6-32
Formula 6-33
Formula 6-34
Formula 6-35
Formula 6-36
Formula 6-37
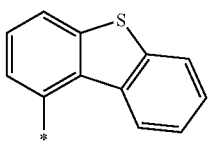
Formula 6-38
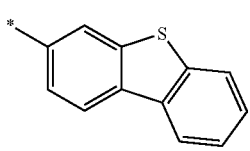
Formula 6-39
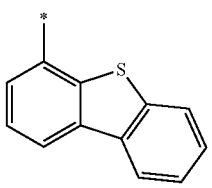
Formula 6-40
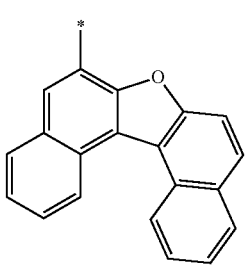
Formula 6-41
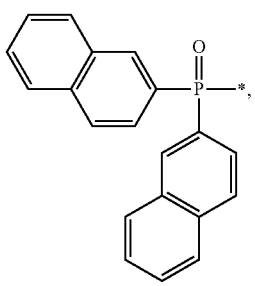
Formula 6-42
where * and *' in Formulae 4-1 to 4-8 and Formulae 6-1 to 6-42 may each be a binding site to a neighboring atom.
The condensed cyclic compound represented by one selected from Formulae 1-1 and 1-2 may be one selected from Compounds 1 to 110:
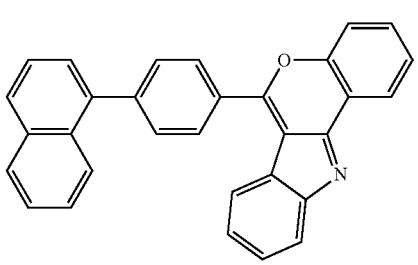
1

2
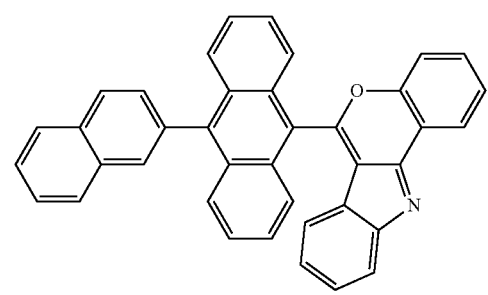
3
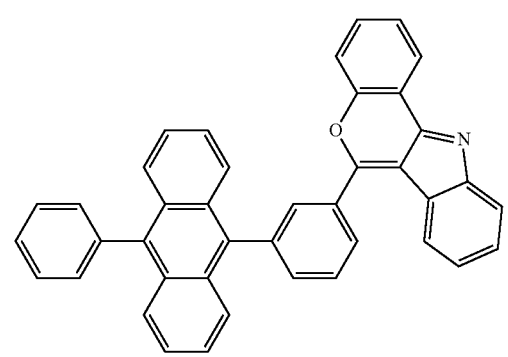
4
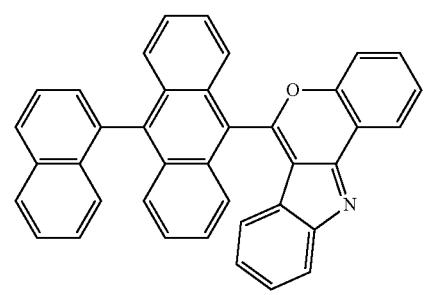
5
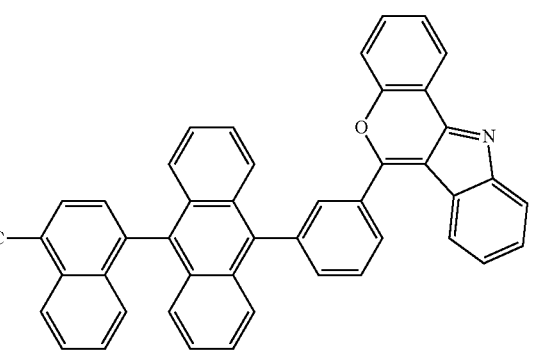
6
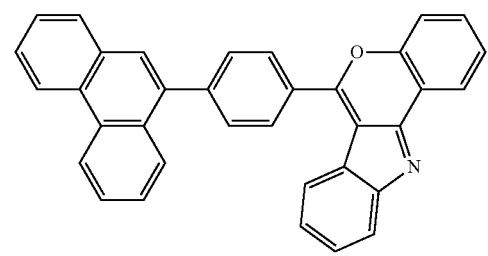
7
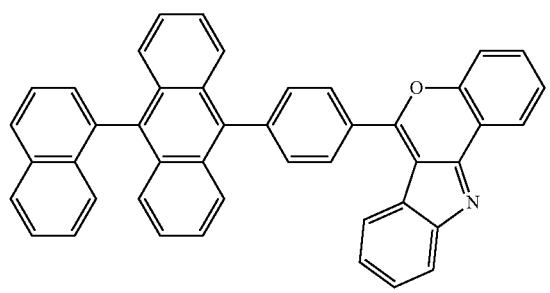
8
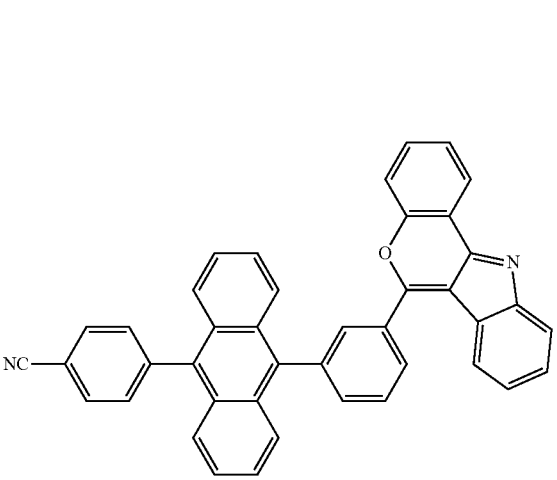
9
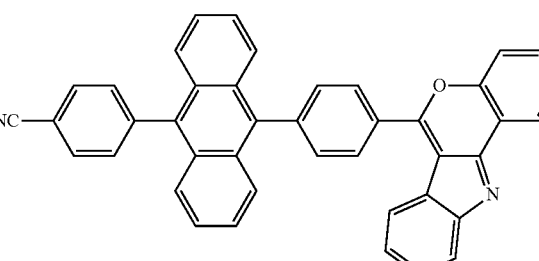
10
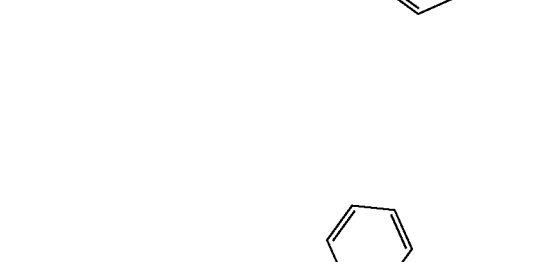

8
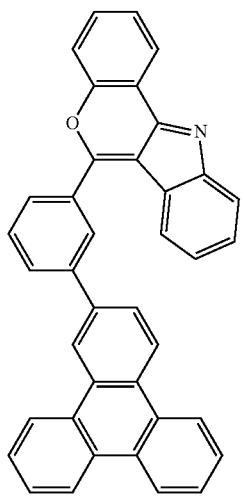
9
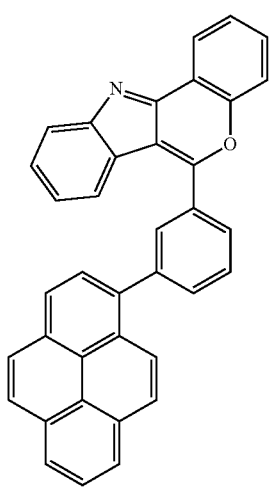
10
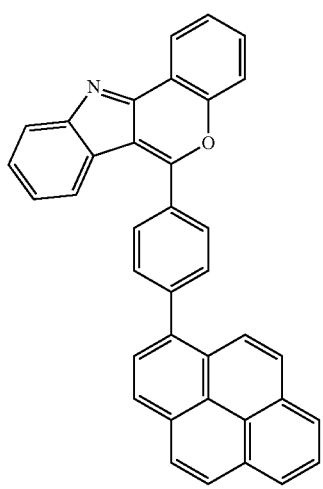
11
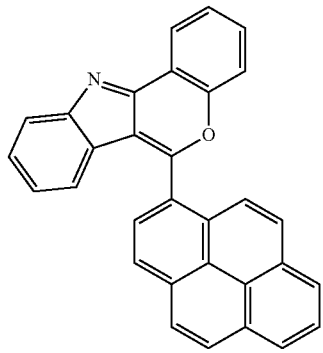
12
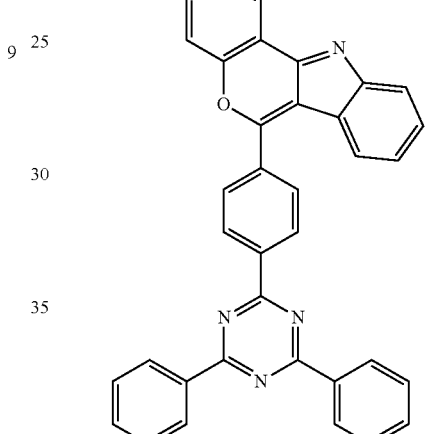
13
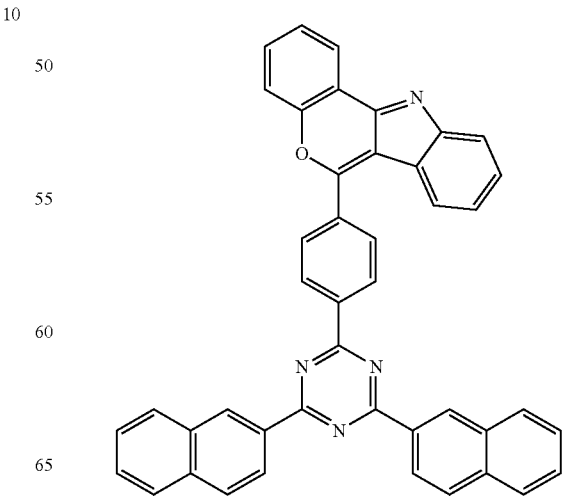

14
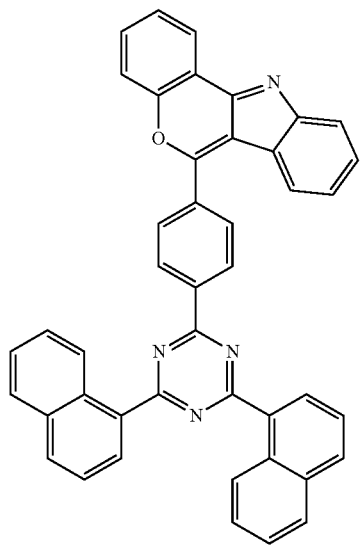
15
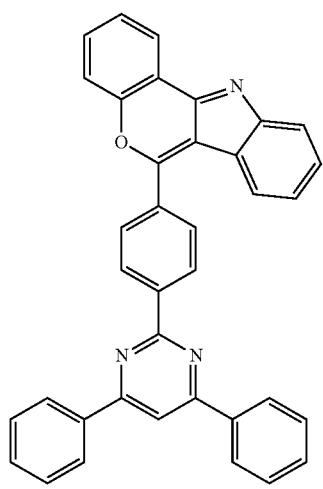
16
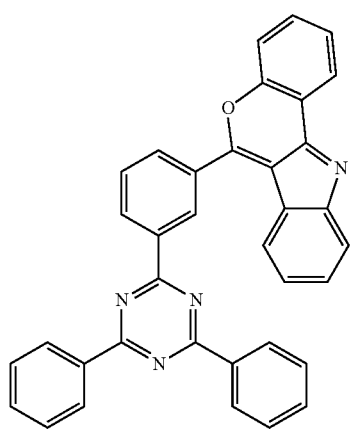
17
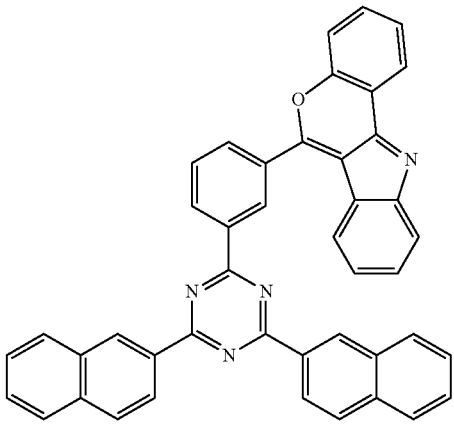
18
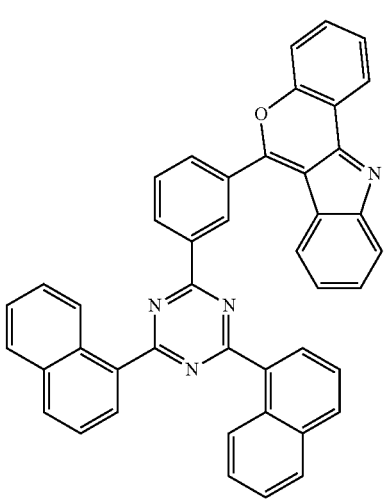
19
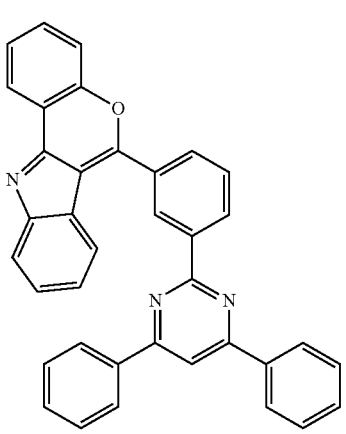

49
-continued
20
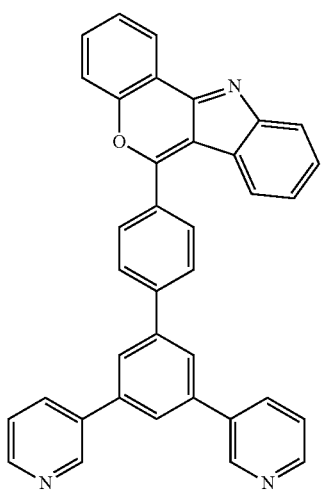
21
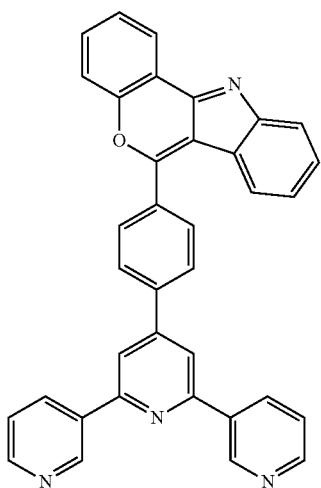
22
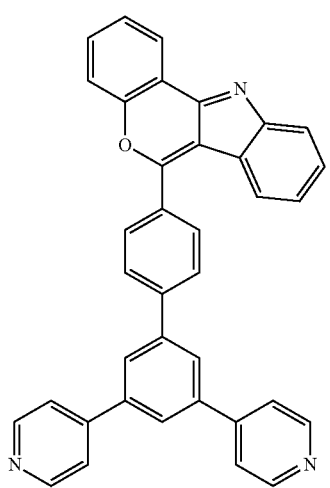
50
-continued
23
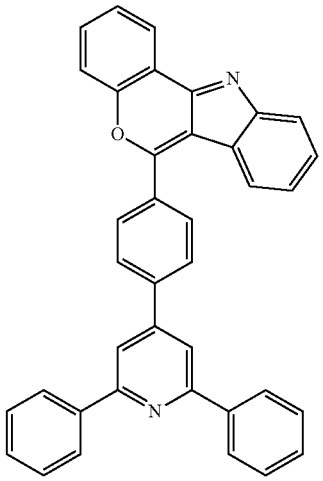
24
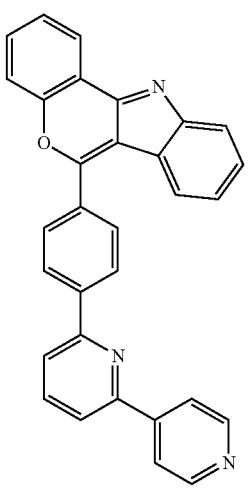
25
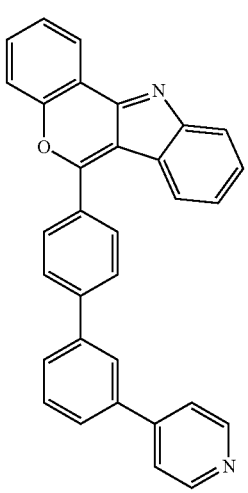

26
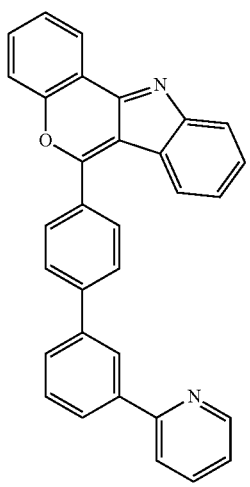
27
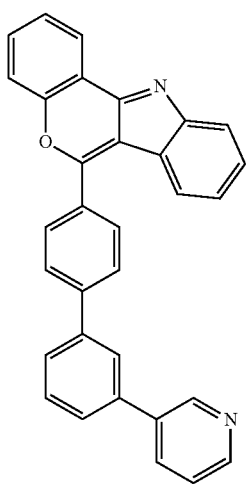
28
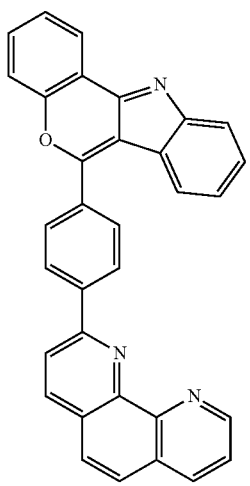
29
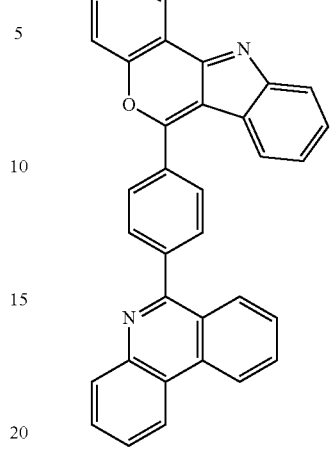
30
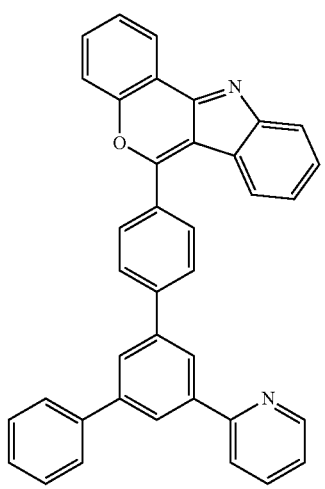
31
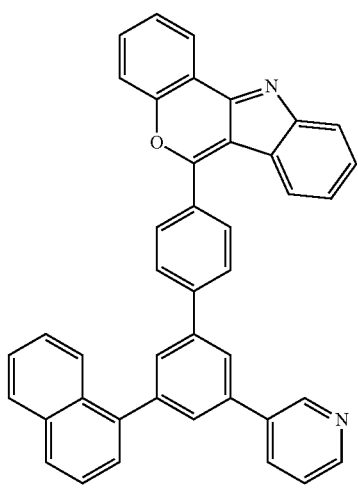

32
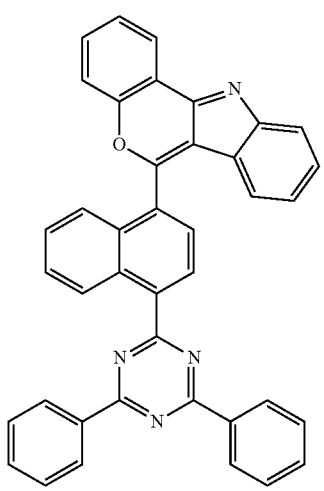
33
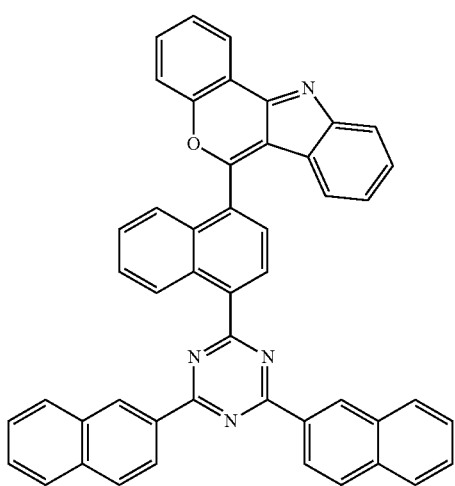
34
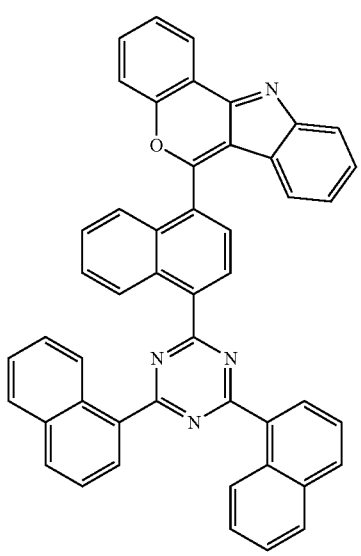
35
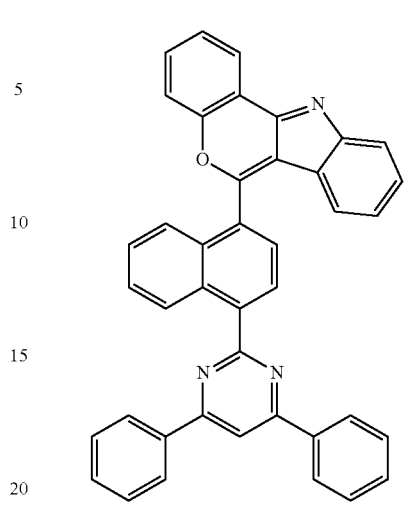
36
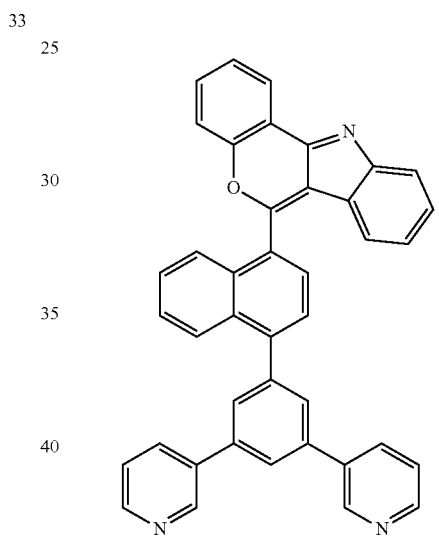
37
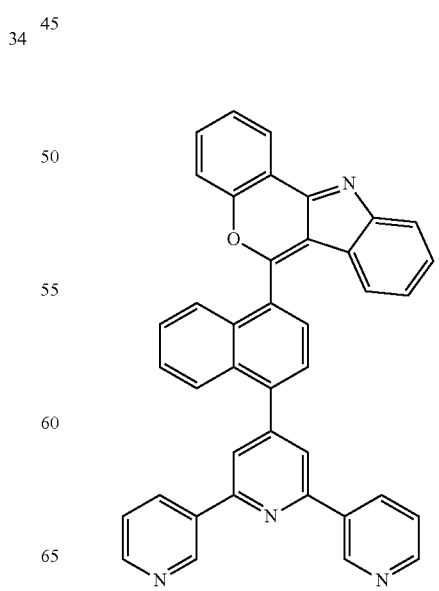

38
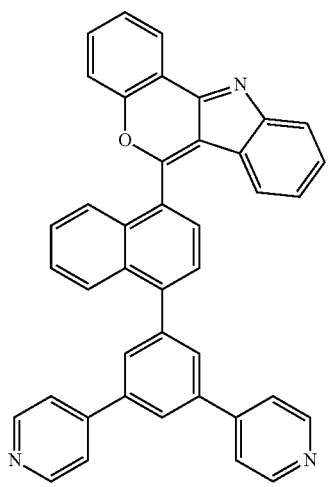
39
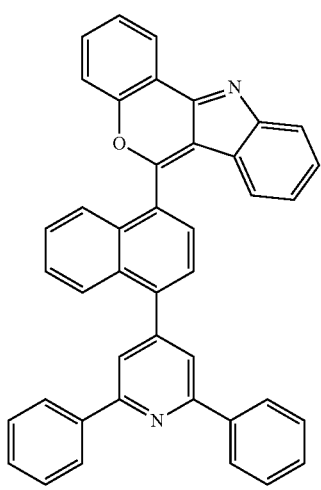
40
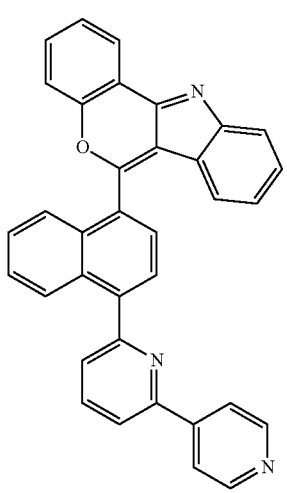
41
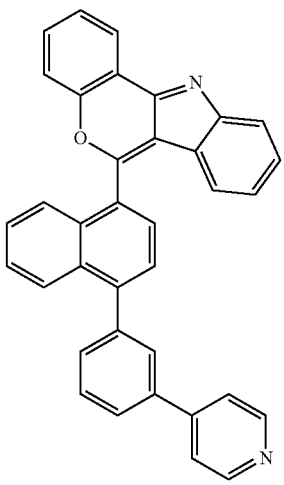
42
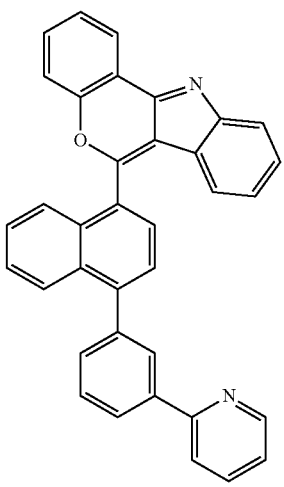
43
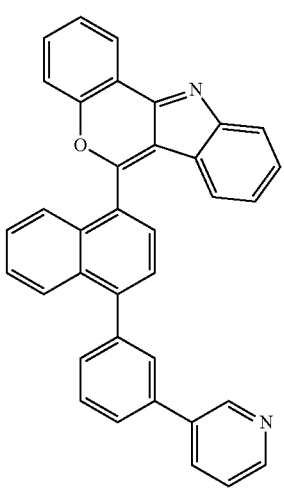

44
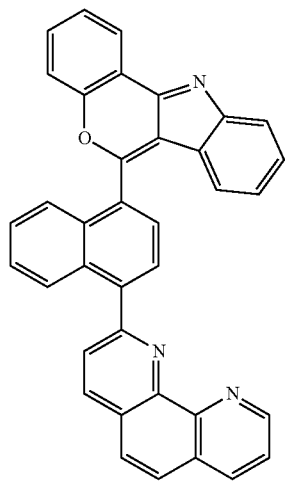
45
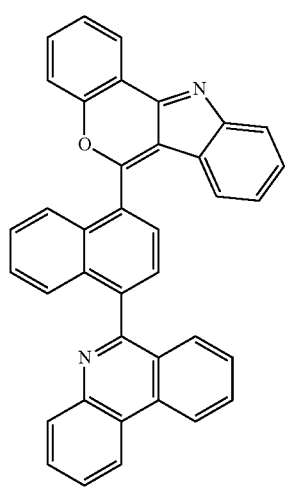
46
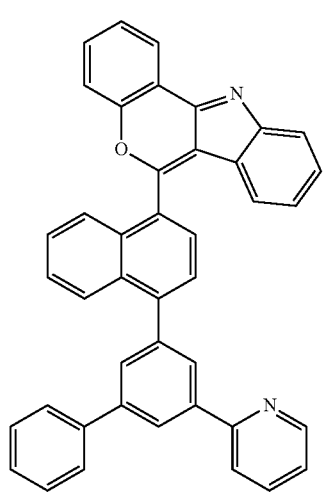
47
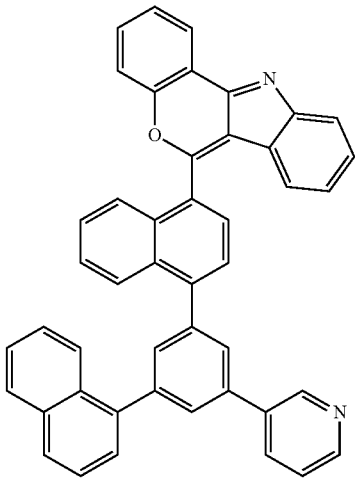
48
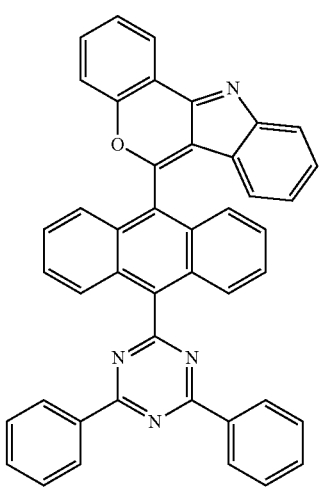
49
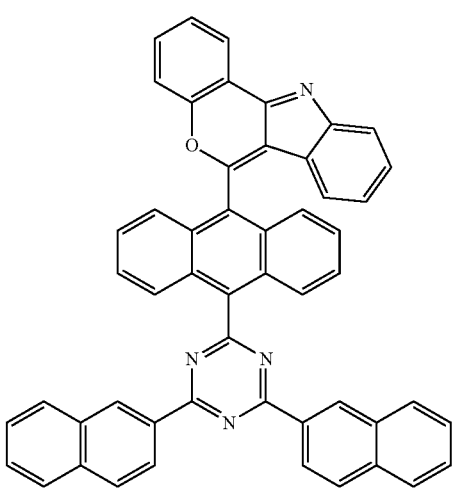

50
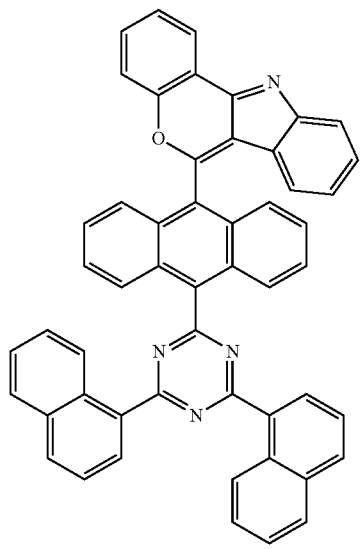
51
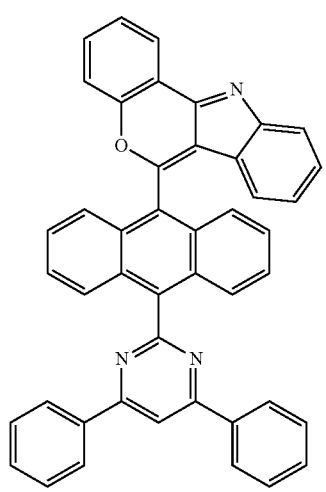
52
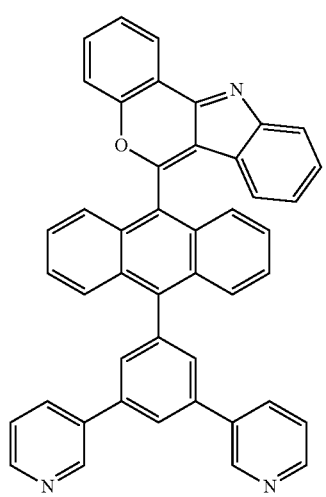
53
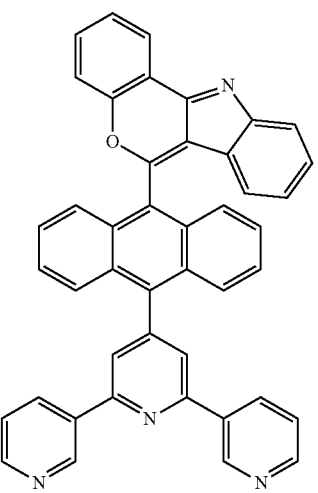
54
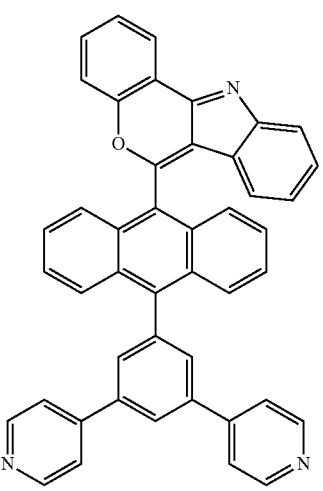
55
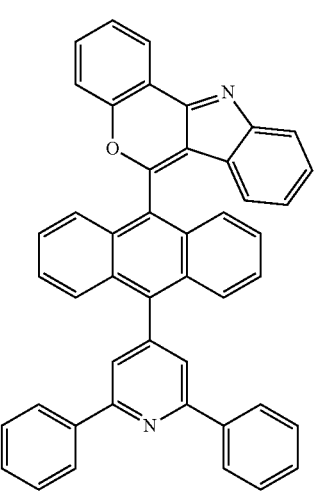

61
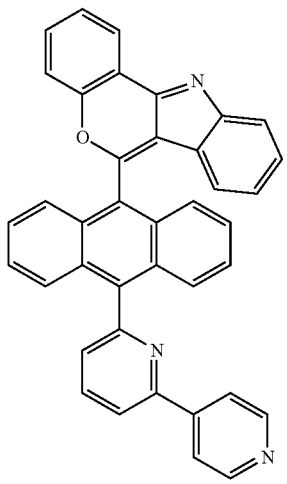
56
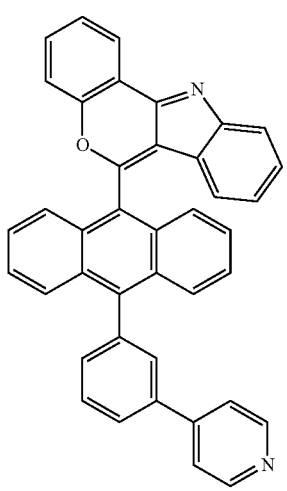
57
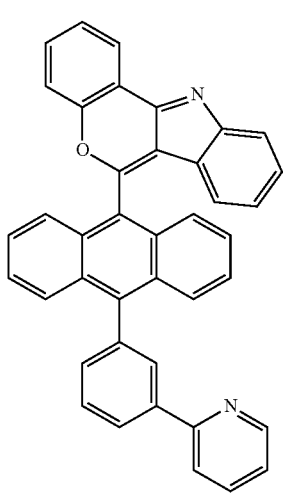
58
62
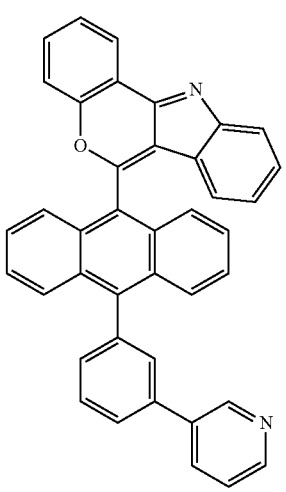
59
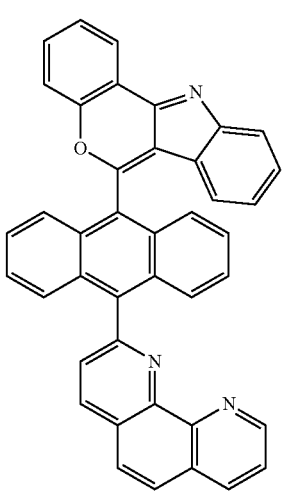
60
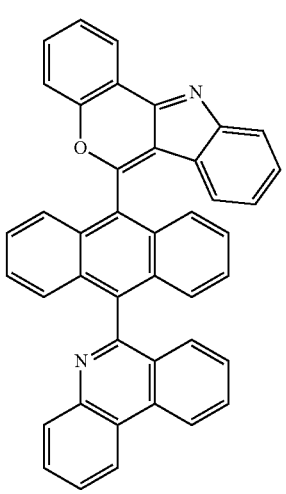
61

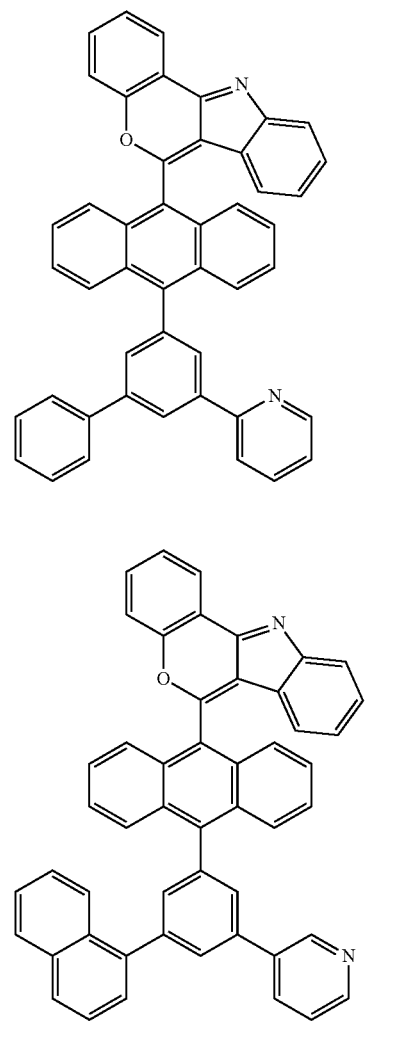
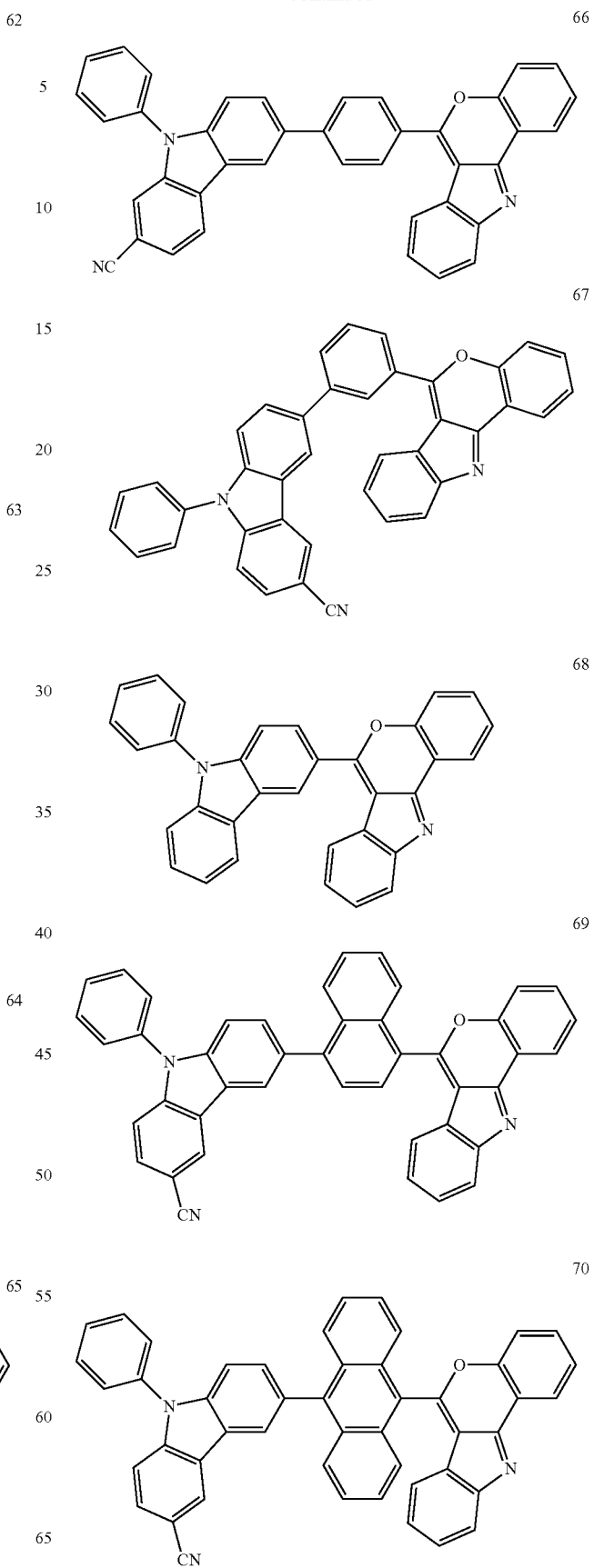

71
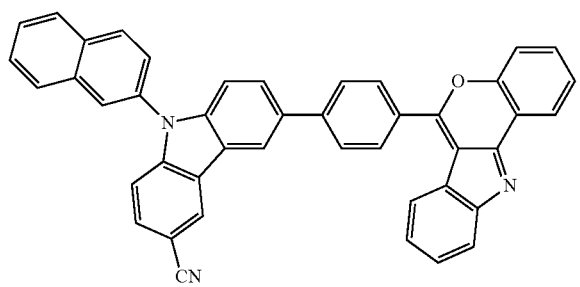
72
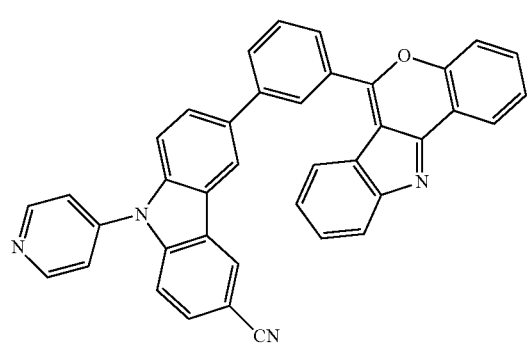
73
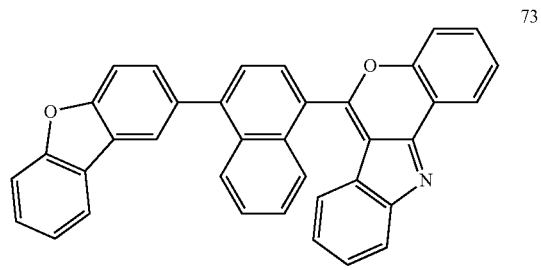
74
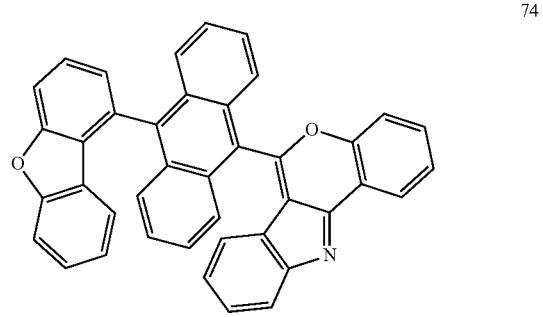
75
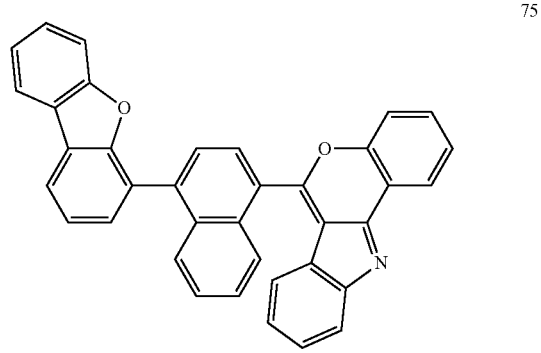
76
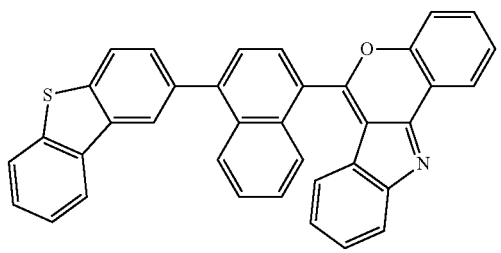
77
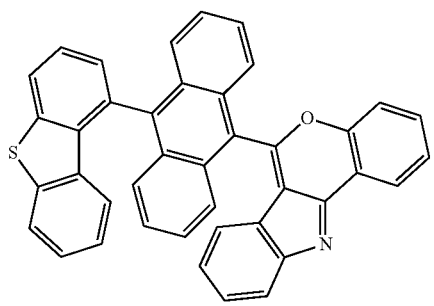
78
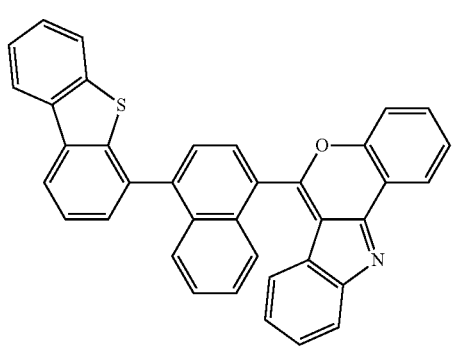
79
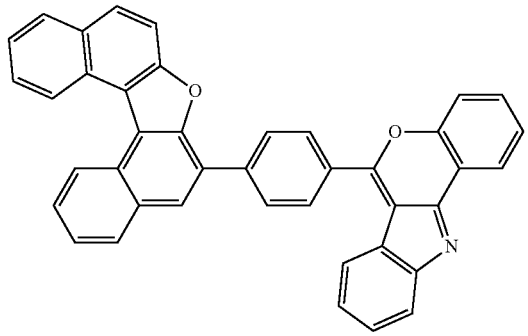
80
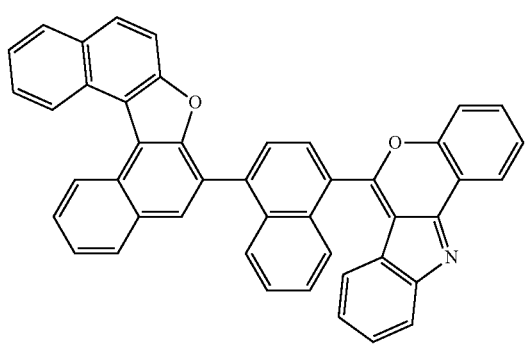

81
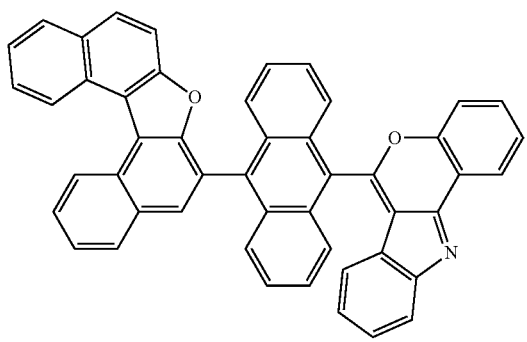
82
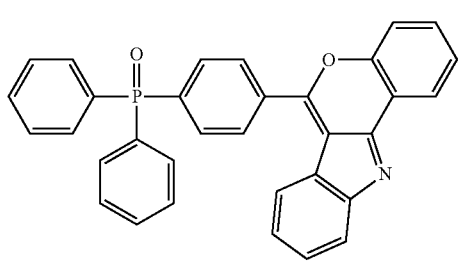
83
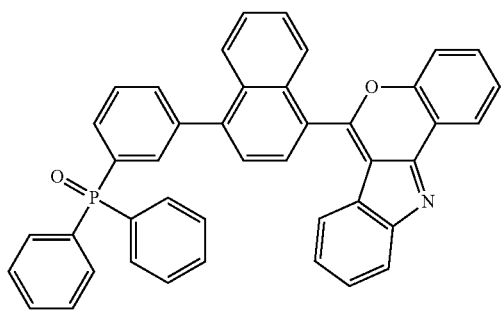
84
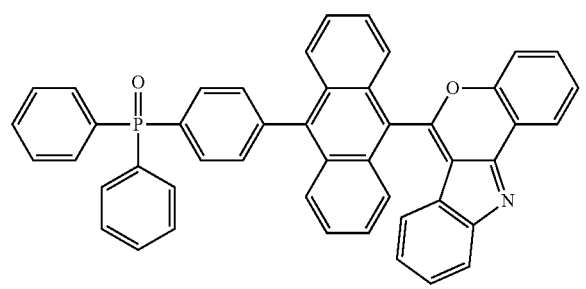
85
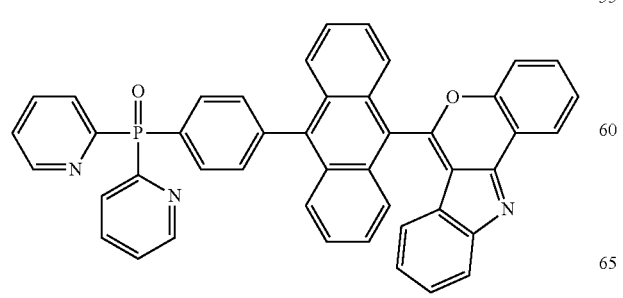
86
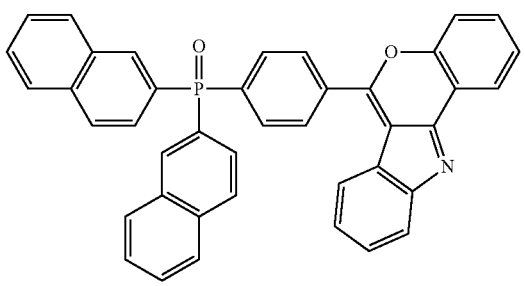
87
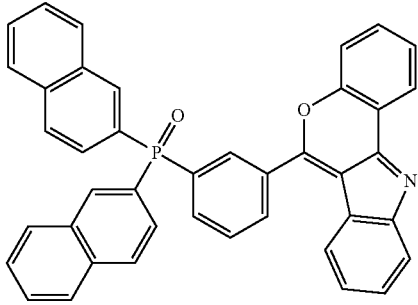
88
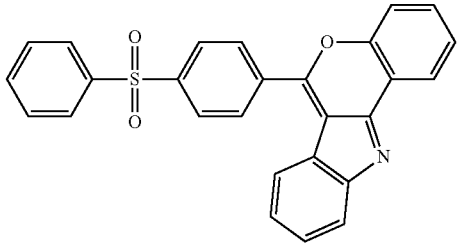
89
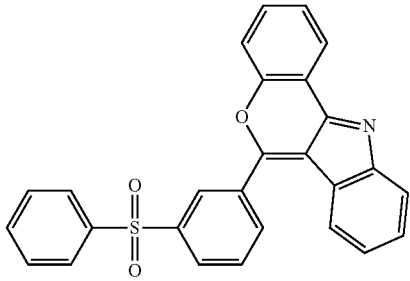
90
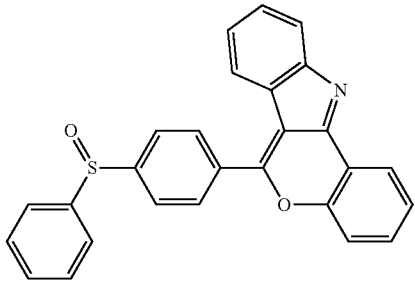

91
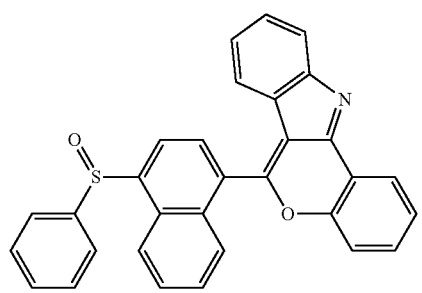
92
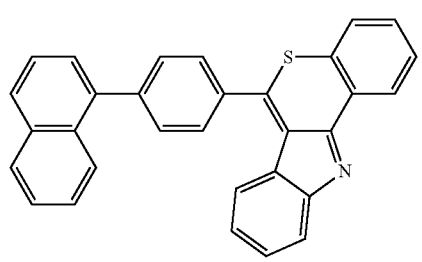
93
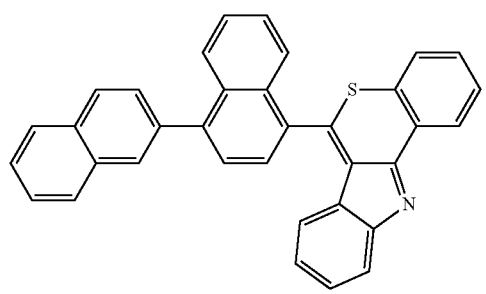
94
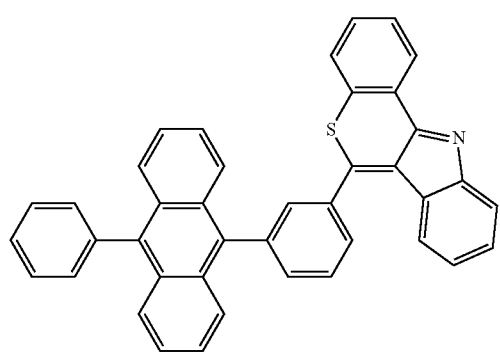
95
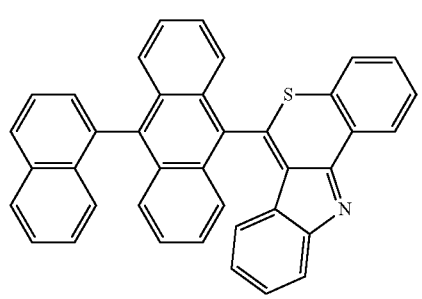
96
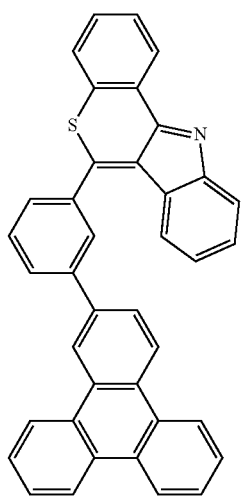
97
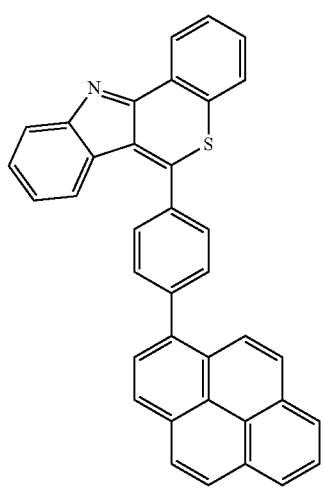
98
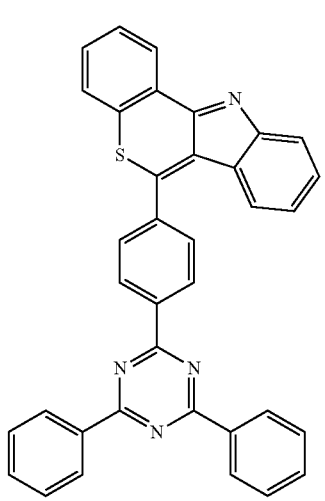

99
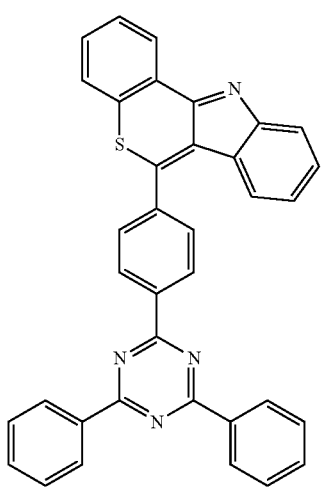
102
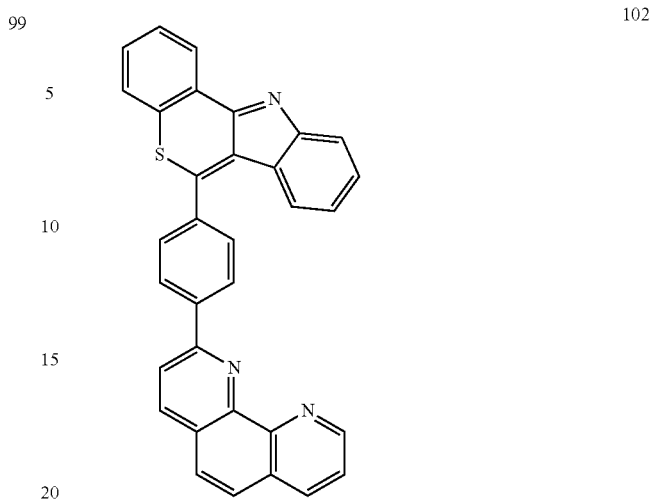
100
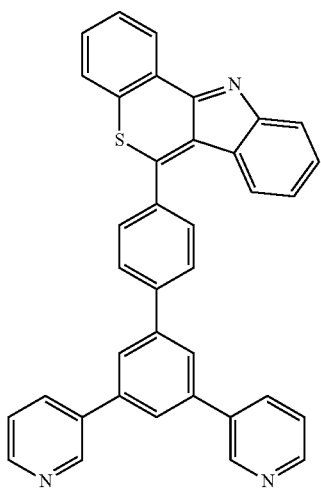
103
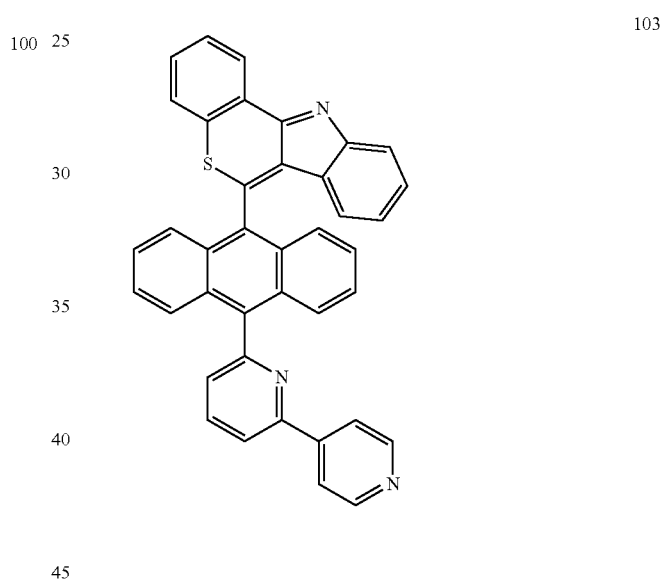
101
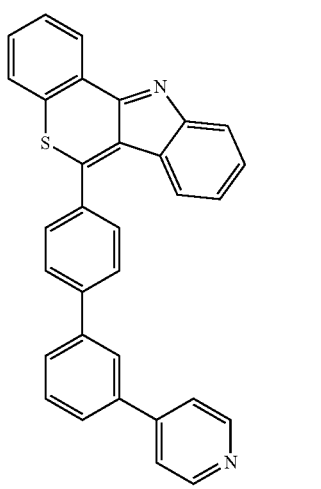
104
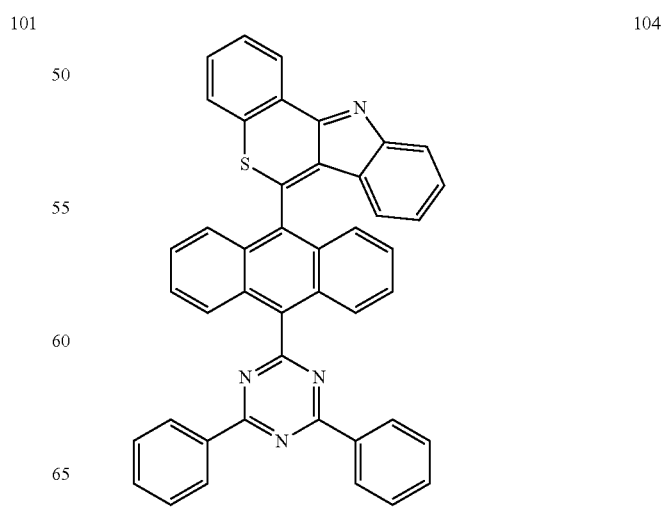

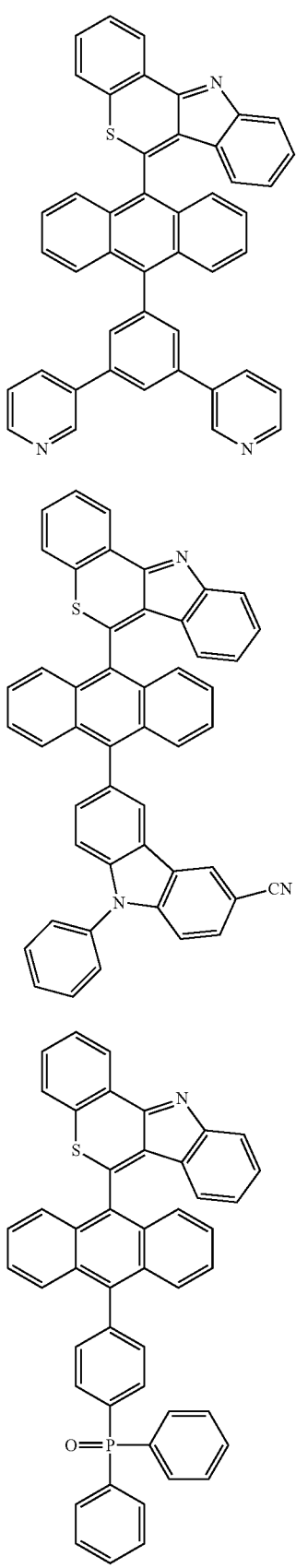
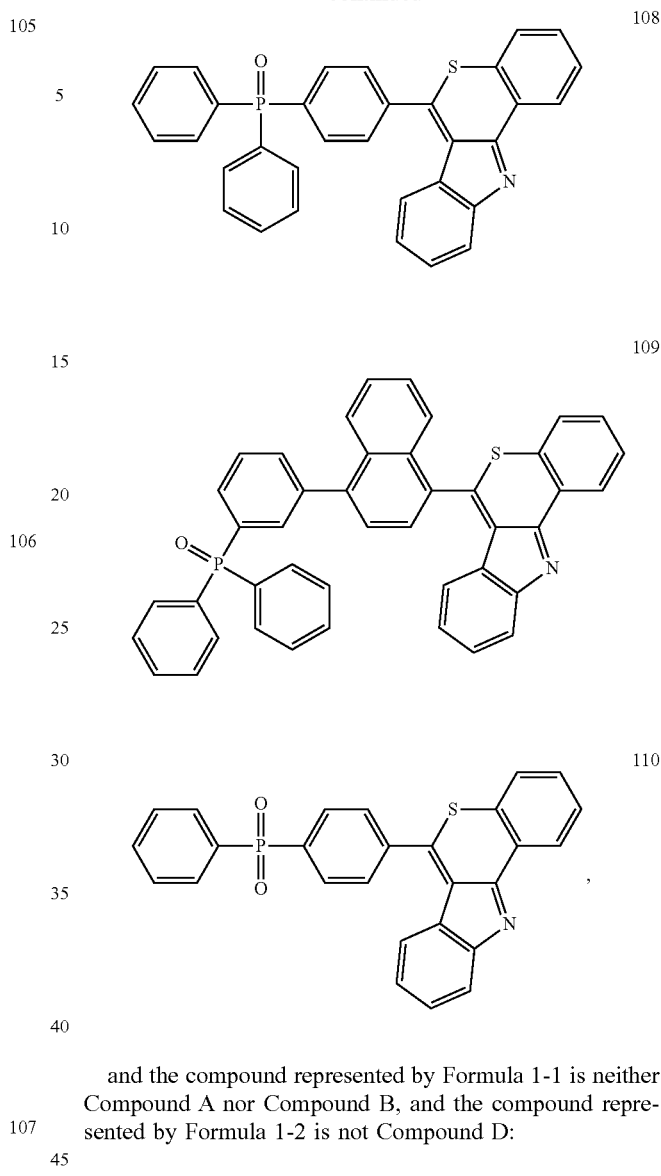
and the compound represented by Formula 1-1 is neither Compound A nor Compound B, and the compound represented by Formula 1-2 is not Compound D:
Compound A
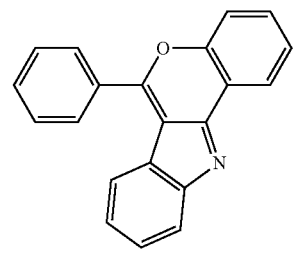
Compound B
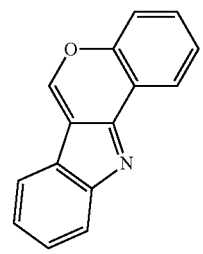

-continued

Compound D

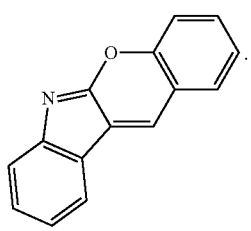

The condensed cyclic compound represented by Formula 1-1 may have a core

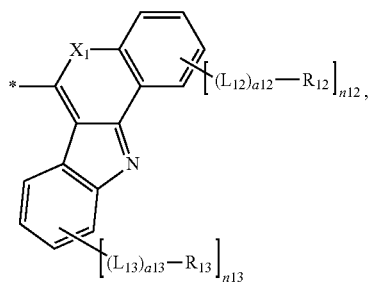

and the condensed cyclic compound represented by Formula 1-2 may include a core

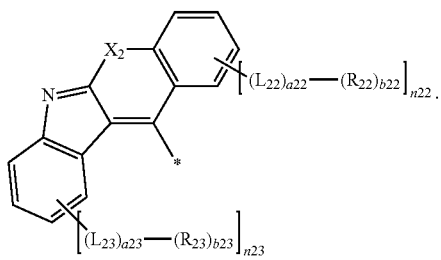

In each of these cores, for example when $X_1$ and $X_2$ are each —O—, benzopyran and indole are condensed (e.g., linked and/or fused) to each other, thereby resulting in a delocalized structure of 17 π-electrons capable of improving electron transport characteristics.

$X_1$ and $X_2$ in the cores of Formulae 1-1 and 1-2 may each independently be selected from —O— and —S—, each having two unshared electron pairs. Accordingly, the cores of Formulae 1-1 and 1-2 may each independently receive excess electrons from the unshared electron pairs of $X_1$ and/or $X_2$. Thus, the center of the compound represented by any one selected from Formulae 1-1 and 1-2 may be enriched with π-electrons, and thus, π→π* transition and n>π* transitions may be more likely to occur, thus increasing luminescent efficiency of the condensed cyclic compound.

In some embodiments, the compound represented by Formula 1-1 is neither Compound A nor Compound B, and the compound represented by Formula 1-2 is not Compound D. Accordingly, electron transport characteristics of the condensed cyclic compound represented by one selected from Formulae 1-1 and 1-2 may be improved, and the organic light-emitting device including the condensed cyclic compound represented by one selected from Formulae 1-1 and 1-2 may have higher efficiency and longer lifespan.

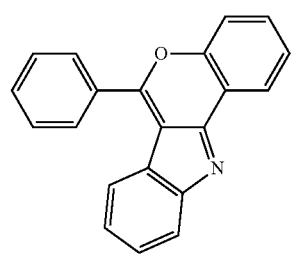

Compound A

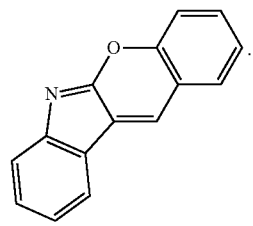

Compound B

Compound D

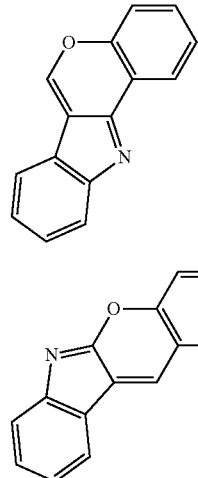

The condensed cyclic compound represented by one selected from Formulae 1-1 and 1-2 may be synthesized by using (utilizing) any suitable organic synthesis method generally available in the art of organic light-emitting devices, and such synthesis methods should be apparent to those of ordinary skill in the art in view of the embodiments described herein.

At least one selected from the condensed cyclic compounds represented by one selected from Formulae 1-1 and 1-2 may be used between a pair of electrodes of an organic light-emitting device. In some embodiments, the condensed cyclic compound may be included in an electron transport region, for example, an electron transport layer. Accordingly, an organic light-emitting device according to one or more embodiments of the present disclosure may include: a first electrode; a second electrode facing the first electrode; and an organic layer between the first electrode and the second electrode, the organic layer including an emission layer and at least one selected from the condensed cyclic compounds represented by one selected from Formulae 1-1 and 1-2.

The expression "(an organic layer) includes at least one selected from the condensed cyclic compounds" used herein may refer to a case in which (an organic layer) includes one or more identical condensed cyclic compounds represented by one selected from Formulae 1-1 and 1-2 and/or a case in which (an organic layer) includes two or more different condensed cyclic compounds represented by one selected from Formulae 1-1 and 1-2.

For example, the organic layer may include, as the condensed cyclic compound represented by one selected from Formulae 1-1 and 1-2, only Compound 1. For example, Compound 1 may be present in an electron transport layer of an organic light-emitting device. In some embodiments, the organic layer may include, as the condensed cyclic compound represented by one selected from Formulae 1-1 and 1-2, Compound 1 and Compound 2. For example, Compound 1 and Compound 2 may both be present in the same layer (for example, Compound 1 and Compound 2 may both be present in an electron transport layer), or may be present in different layers (for example, Compound 1 may be present in an emission layer and Compound 2 may be present in an electron transport layer).

In some embodiments, the organic layer includes i) a hole transport region between the first electrode (e.g., an anode) and the emission layer, the hole transport region including at least one selected from a hole injection layer, a hole transport layer, a buffer layer, and an electron blocking layer, and ii) an electron transport region between the emission layer and the second electrode (e.g., a cathode), the electron transport region including at least one selected from a hole blocking layer, an electron transport layer, and an electron injection layer. The electron transport region may include at least one selected from the condensed cyclic compounds represented by any one selected from Formulae 1-1 and 1-2. For example, the electron transport region may include the electron transport layer, wherein the electron transport layer may include at least one selected from the condensed cyclic compounds represented by one selected from Formulae 1-1 and 1-2.

The term "organic layer" used herein may refer to a single layer and/or a plurality of layers positioned between the first electrode and the second electrode of an organic light-emitting device. A material included in the "organic layer" is not limited to an organic material.

The drawing is a schematic view of an organic light-emitting device 10 according to one or more embodiments of the present disclosure. The organic light-emitting device 10 includes a first electrode 110, an organic layer 150, and a second electrode 190.

Hereinafter, the structure of an organic light-emitting device according to one or more embodiments of the present disclosure and a method of manufacturing the organic light-emitting device according to one or more embodiments will be described in connection with the drawing.

In the drawing, a substrate may be additionally placed under the first electrode 110 or above the second electrode 190. The substrate may be a glass substrate or transparent plastic substrate, each with excellent mechanical strength, thermal stability, transparency, surface smoothness, ease of handling, and/or water-resistance.

The first electrode 110 may be formed by depositing or sputtering a material for forming the first electrode on the substrate. When the first electrode 110 is an anode, the material for forming the first electrode 110 may be selected from materials with a high work function so as to facilitate hole injection (e.g., make holes be easily injected). The first electrode 110 may be a reflective electrode or a transmissive electrode. The material for forming the first electrode 110 may be a transparent and/or highly conductive material, and non-limiting examples of such material include indium tin oxide (ITO), indium zinc oxide (IZO), tin oxide (SnO$_2$), and zinc oxide (ZnO). When the first electrode 110 is a semi-transmissive electrode or a reflective electrode, as a material for forming the first electrode, at least one selected from magnesium (Mg), aluminum (Al), aluminum-lithium (Al—Li), calcium (Ca), magnesium-indium (Mg—In), magnesium-silver (Mg—Ag) may be used.

The first electrode 110 may have a single-layer structure, or a multi-layer structure including two or more layers. For example, the first electrode 110 may have a three-layered structure of ITO/Ag/ITO, but the structure of the first electrode 110 is not limited thereto.

The organic layer 150 may be positioned on the first electrode 110. The organic layer 150 may include an emission layer.

The organic layer 150 may further include a hole transport region between the first electrode and the emission layer, and an electron transport region between the emission layer and the second electrode.

The hole transport region may include at least one selected from a hole injection layer (HIL), a hole transport layer (HTL), a buffer layer, and an electron blocking layer (EBL), and the electron transport region may include at least one selected from a hole blocking layer (HBL), an electron transport layer (ETL), and an electron injection layer (EIL), but the structures of the hole transport region and the electron transport region are not limited thereto.

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, wherein the layers of each structure are sequentially stacked from the first electrode 110 in this stated order, but the structure of the hole transport region is not limited thereto.

When the hole transport region includes a hole injection layer, the hole injection layer may be formed on the first electrode 110 by using one or more suitable methods, such as vacuum deposition, spin coating casting, a Langmuir-Blodgett (LB) method, ink-jet printing, laser-printing, and/or laser-induced thermal imaging.

When the hole injection layer is formed by vacuum deposition, for example, the vacuum deposition may be performed at a deposition temperature of about 100° C. to about 500° C., at a vacuum degree of about $10^{-8}$ to about $10^{-3}$ torr, and at a deposition rate of about 0.01 to about 100 Å/sec, depending on the compound for forming the hole injection layer to be deposited, and the structure of the hole injection layer to be formed.

When the hole injection layer is formed by spin coating, for example, the spin coating may be performed at a coating rate of about 2000 rpm to about 5000 rpm, and at a temperature of about 80° C. to 200° C., depending on the compound for forming the hole injection layer to be deposited, and the structure of the hole injection layer to be formed.

When the hole transport region includes a hole transport layer, the hole transport layer may be formed on the first electrode 110 or the hole injection layer by using one or more suitable methods, such as vacuum deposition, spin coating, casting, a LB method, ink-jet printing, laser-printing, and/or laser-induced thermal imaging. When the hole transport layer is formed by vacuum deposition and/or spin coating, deposition and coating conditions for the hole transport layer may be similar to the deposition and coating conditions for the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4''-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), (polyaniline)/poly(4-styrenesulfonate) (PANI/PSS), a compound represented by Formula 201, and a compound represented by Formula 202:

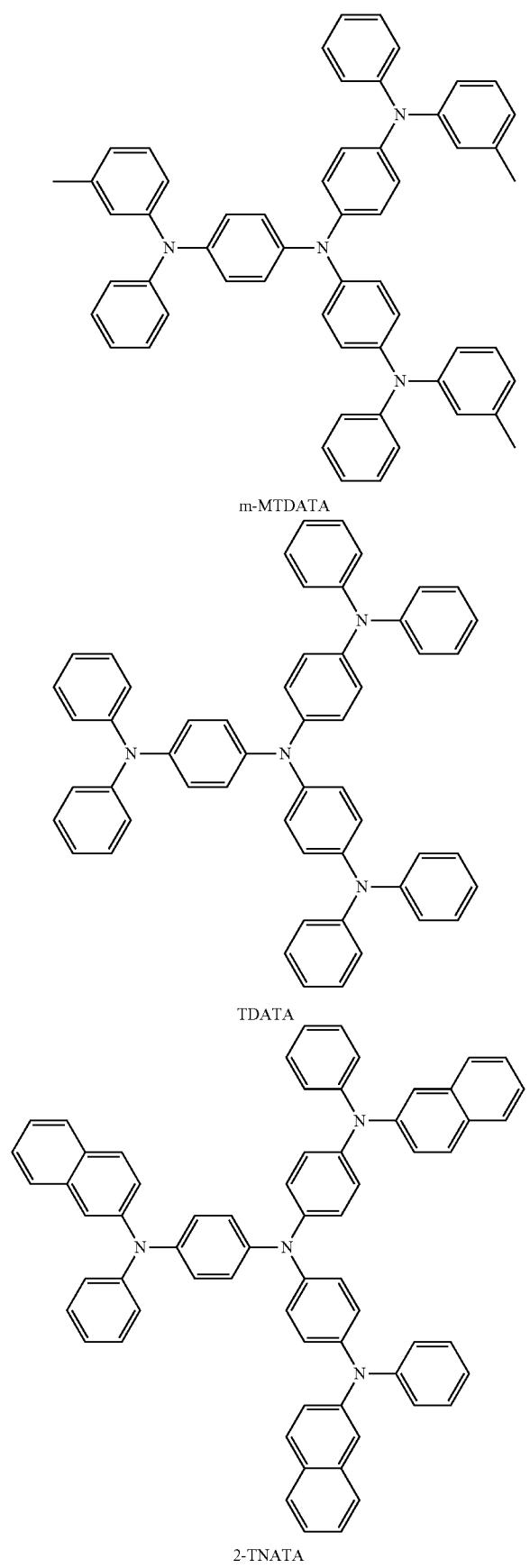
m-MTDATA
TDATA
2-TNATA
-continued
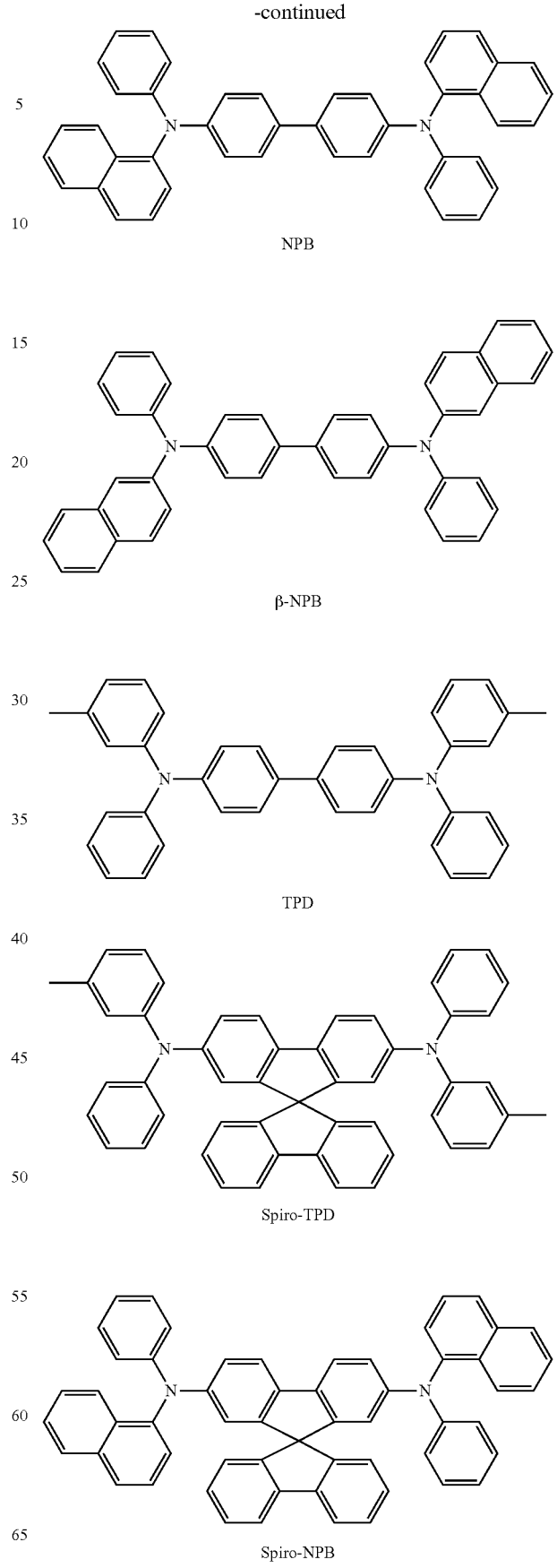
NPB
β-NPB
TPD
Spiro-TPD
Spiro-NPB -continued

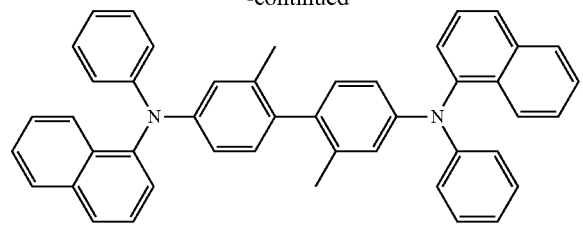

methylated NPB

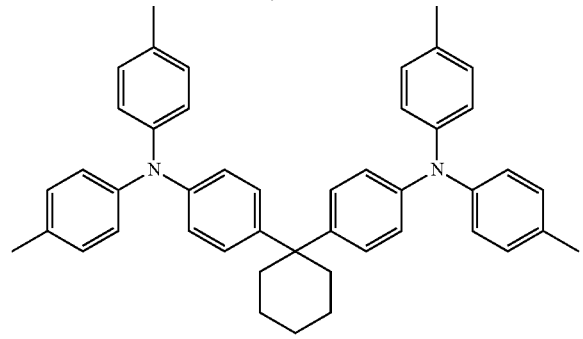

TAPC

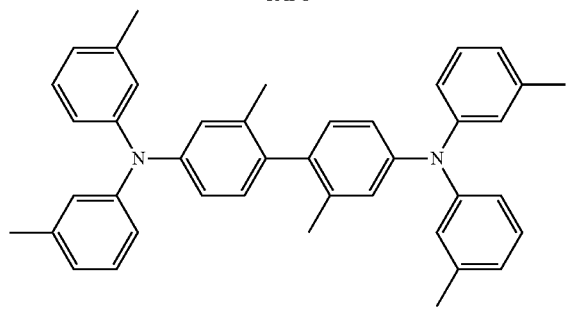

HMTPD

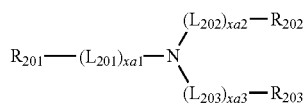

Formula 201

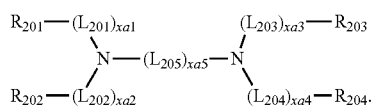

Formula 202

In Formulae 201 and 202, $L_{201}$ to $L_{205}$ may be each independently the same (or substantially the same) as explained herein in connection with $L_1$ to $L_3$;

xa1 to xa4 may be each independently selected from 0, 1, 2, and 3;

xa5 may be selected from 1, 2, 3, 4, and 5; and $R_{201}$ to $R_{204}$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formulae 201 and 202, $L_{201}$ to $L_{205}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently selected from 0, 1, and 2;

xa5 may be selected from 1, 2, and 3;

$R_{201}$ to $R_{204}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments of the present disclosure are not limited thereto.

The compound represented by Formula 201 may be represented by Formula 201A, but is not limited thereto:

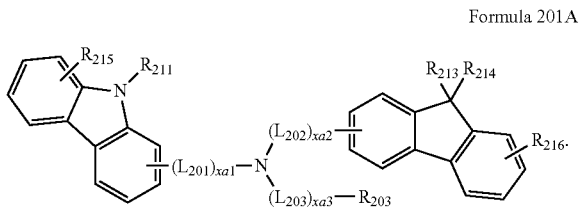

Formula 201A

For example, the compound represented by Formula 201 may be represented by Formula 201A-1, but is not limited thereto:

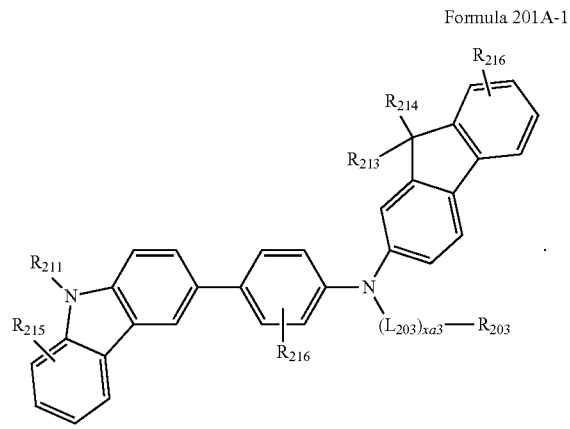

Formula 201A-1

For example, the compound represented by Formula 202 may be represented by Formula 202A, but is not limited thereto:

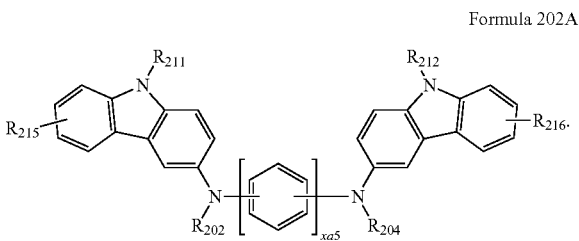

Formula 202A

Regarding Formulae 201A, 201A-1, and 202A, descriptions of $L_{201}$ to $L_{203}$, xa1 to xa3, xa5, and $R_{202}$ to $R_{204}$ are as described above, descriptions of $R_{211}$ and $R_{212}$ may each independently be the same (or substantially the same) as the description of $R_{203}$, and $R_{213}$ to $R_{216}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

For example, in Formulae 201A, 201A-1, and 202A, $L_{201}$ to $L_{203}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may be each independently 0 or 1;

$R_{203}$, $R_{204}$, $R_{211}$, and $R_{212}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may be each independently selected from:
a $C_1$-$C_{20}$ alkyl group and a $C_1$-$C_{20}$ alkoxy group;
a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ may be each independently selected from:
hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 may be 1 or 2.

In some embodiments, $R_{213}$ and $R_{214}$ in Formulae 201A, and 201A-1 may bind to each other (e.g., may be coupled to each other) to form a saturated or unsaturated ring.

The compound represented by Formula 201 and the compound represented by Formula 202 may each independently include at least one selected from compounds HT1 to HT20 illustrated below, but are not limited thereto.

HT1

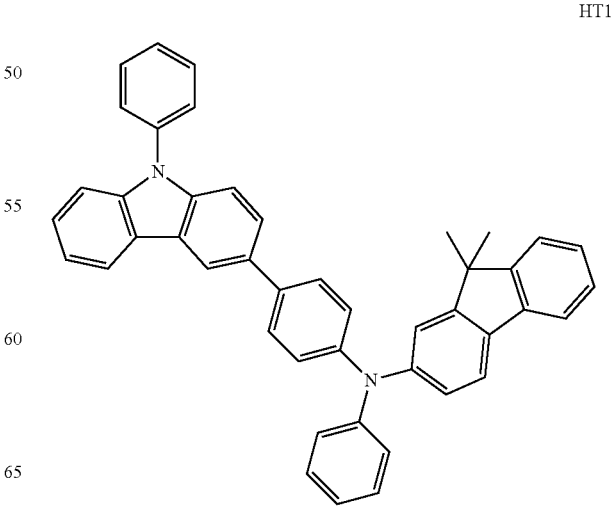

HT2
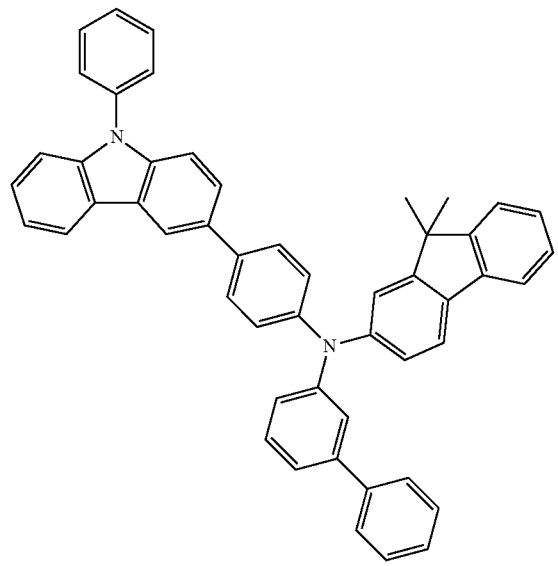
HT3
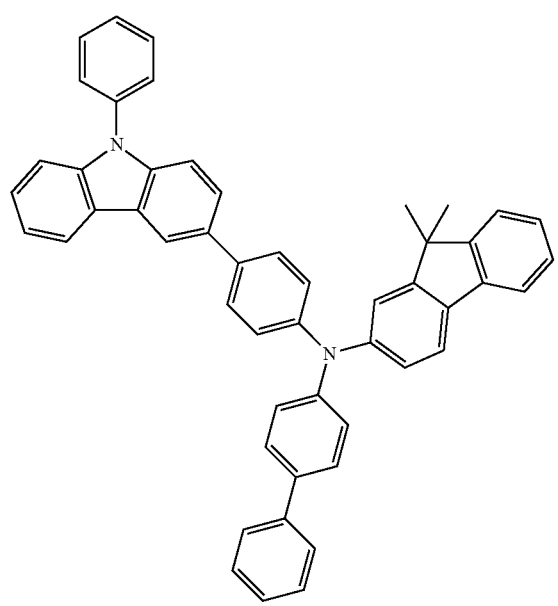
HT4
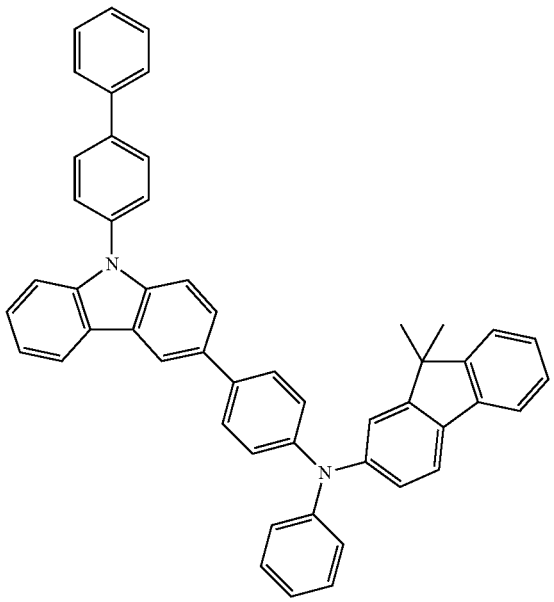
HT5
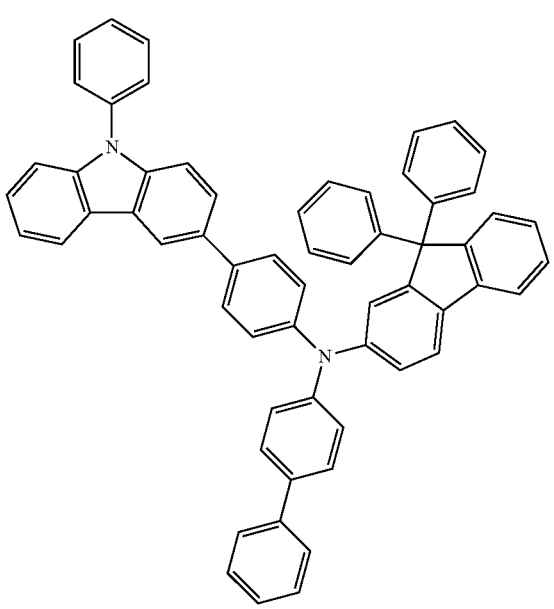

-continued
HT6
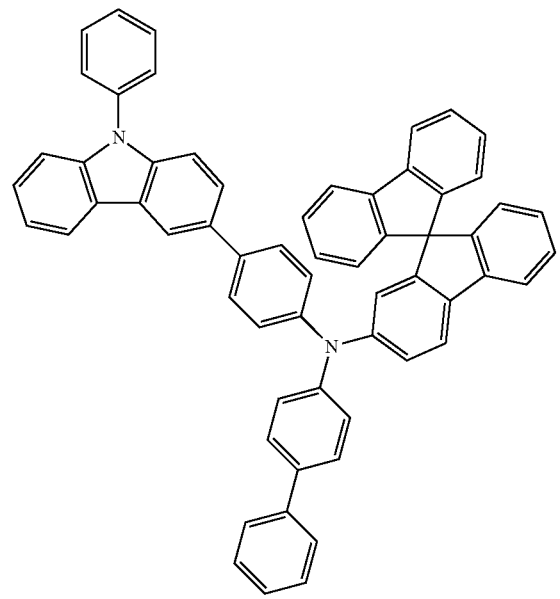
HT7
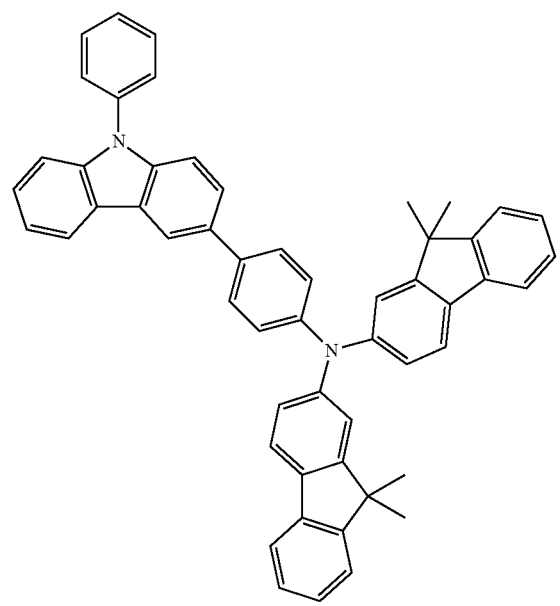
HT8
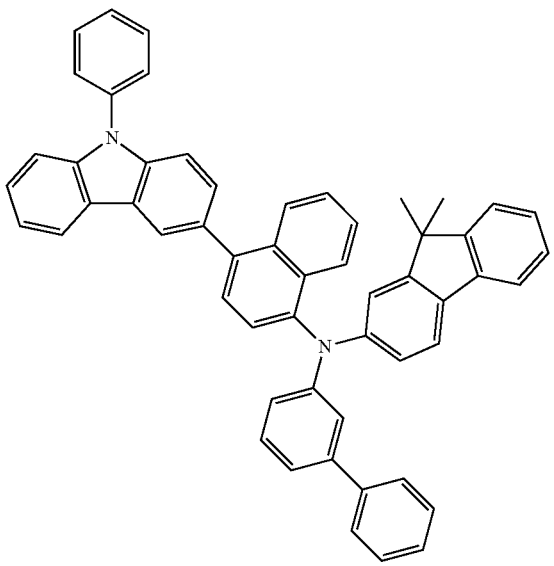
HT9
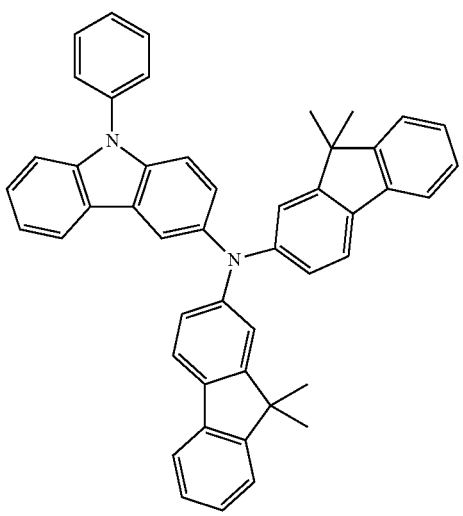

HT10
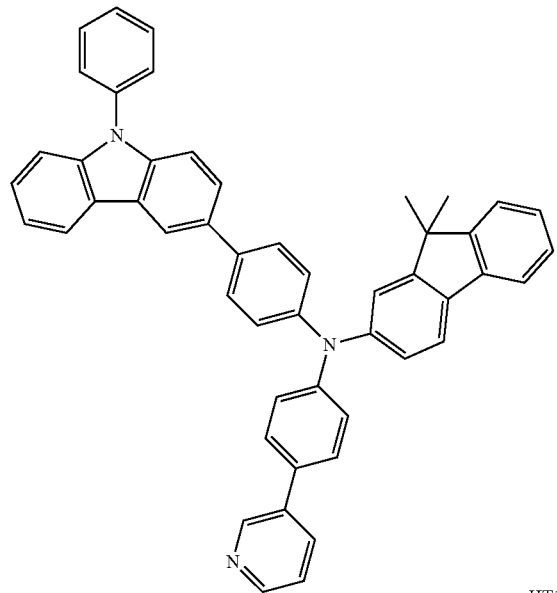
HT11
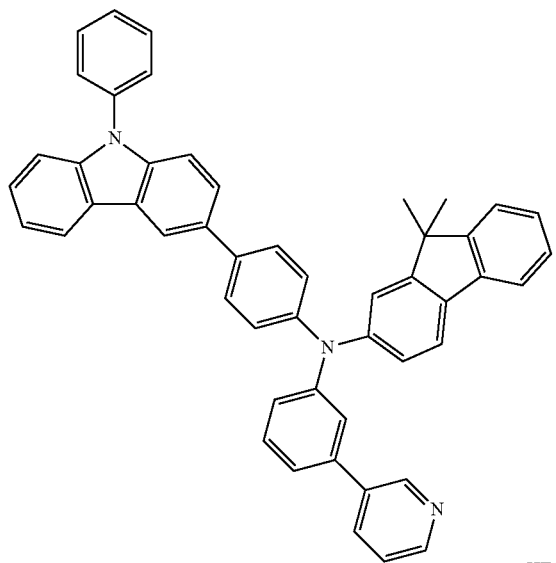
HT12
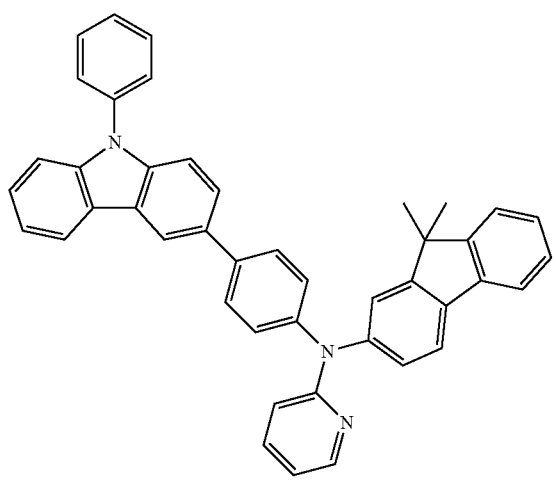
HT13
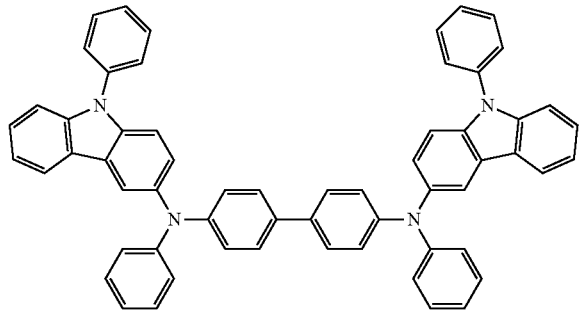
HT14
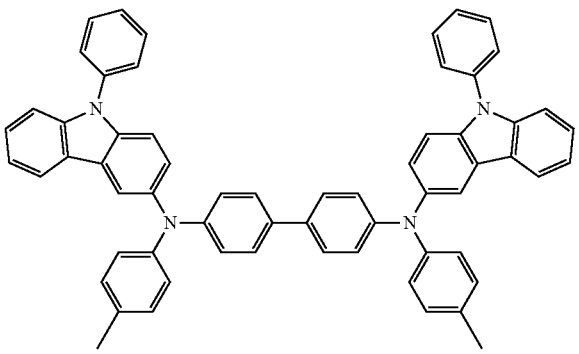
HT15
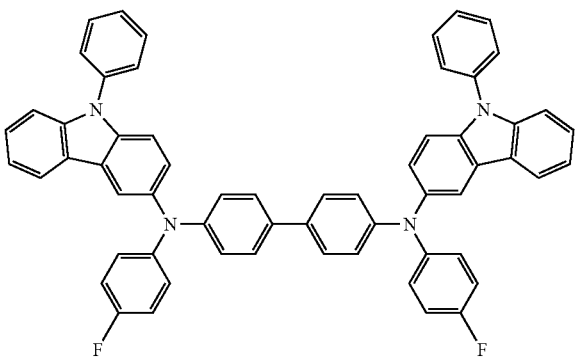
HT16
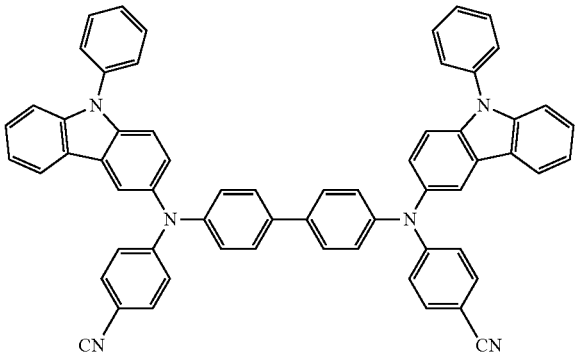

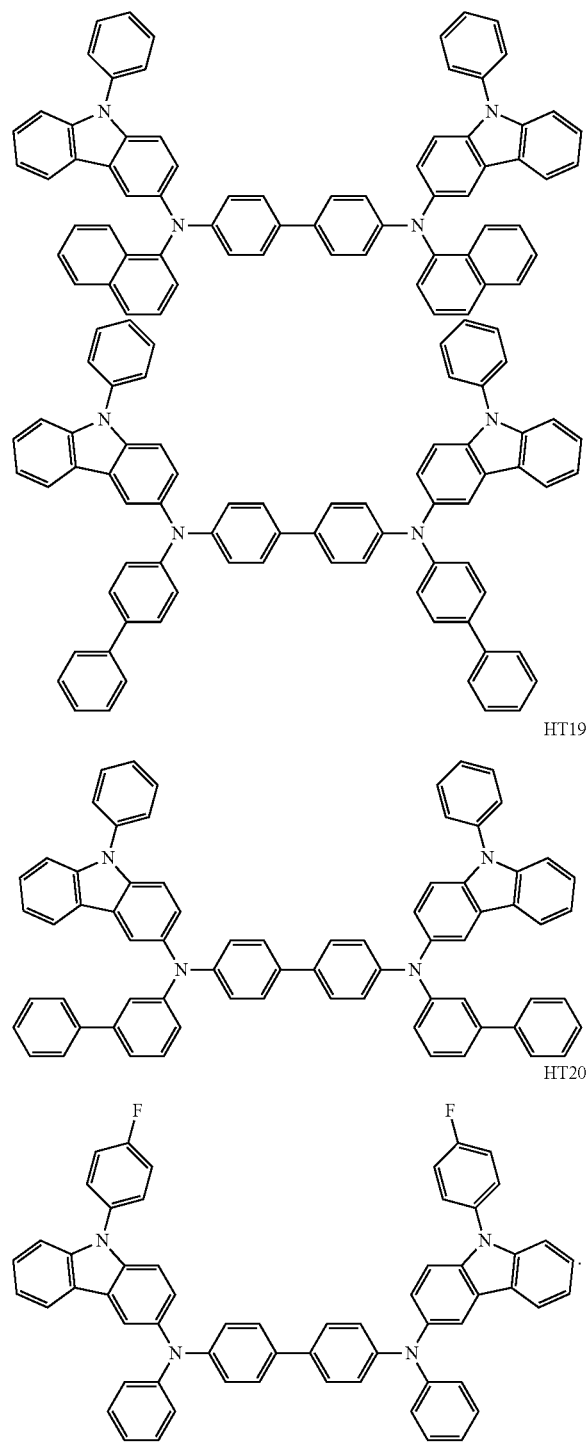

HT17

HT19

HT20

A thickness of the hole transport region may be in a range of about 100 Å to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. When the thicknesses of the hole transport region, the hole injection layer, and the hole transport layer are within any of these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or unhomogeneously dispersed in the hole transport region.

The charge-generation material may be, for example, a p-dopant. The p-dopant may be one selected from a quinone derivative, a metal oxide, and a cyano group-containing compound, but embodiments of the present disclosure are not limited thereto. Non-limiting examples of the p-dopant include quinone derivatives, such as tetracyanoquinonedimethane (TCNQ) and/or 2,3,5,6-tetrafluoro-tetracyano-1,4-benzoquinonedimethane (F4-TCNQ); metal oxides, such as tungsten oxide and/or molybdenum oxide; and Compound HT-D1 illustrated below.

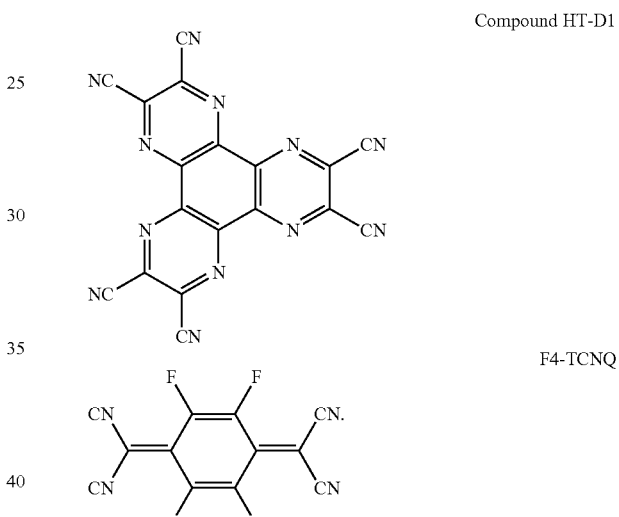

Compound HT-D1

F4-TCNQ

The hole transport region may further include, in addition to the hole injection layer and the hole transport layer, at least one selected from a buffer layer and an electron blocking layer. Since the buffer layer may compensate for an optical resonance distance according to a wavelength of light emitted from the emission layer, light-emission efficiency of the formed organic light-emitting device may be improved. For use as a material included in the buffer layer, materials that are included in the hole transport region may be used. The electron blocking layer may prevent injection of electrons from the electron transport region.

In some embodiments, an emission layer is formed on the first electrode 110 or the hole transport region by using one or more suitable methods, such as vacuum deposition, spin coating, casting, a LB method, ink-jet printing, laser-printing, and/or laser-induced thermal imaging. When the emission layer is formed by vacuum deposition and/or spin coating, deposition and coating conditions for the emission layer may be similar to the deposition and coating conditions for the hole injection layer.

When the organic light-emitting device 10 is a full color organic light-emitting device, the emission layer may be patterned into a red emission layer, a green emission layer, and/or a blue emission layer, according to a sub pixel. In some embodiments, the emission layer may have a stacked structure of a red emission layer, a green emission layer, and a blue emission layer, or may include a red-light emission material, a green-light emission material, and a blue-light emission material, which are mixed with each other in a single layer, to emit white light.

The emission layer may include a host and a dopant. The host may include the condensed cyclic compound represented by one selected from Formulae 1-1 and 1-2.

The dopant may be at least one selected from a phosphorescent dopant and a fluorescent dopant.

For example, the phosphorescent dopant may include an organometallic compound including one selected from iridium (Ir), platinum (Pt), osmium (Os), titanium (Ti), zirconium (Zr), hafnium (Hf), europium (Eu), terbium (Tb), thulium (Tm), rhodium (Rh), and copper (Cu);

For example, the phosphorescent dopant may include an organometallic complex represented by Formula 401:

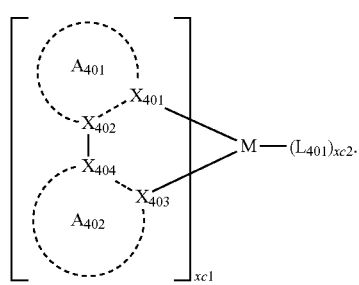

Formula 401

In Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may be each independently nitrogen (—N—) or carbon (—C—);

$A_{401}$ and $A_{402}$ rings may be each independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene; and at least one substituent of the substituted benzene, substituted naphthalene, substituted fluorene, substituted spirofluorene, substituted indene, substituted pyrrole, substituted thiophene, substituted furan, substituted imidazole, substituted pyrazole, substituted thiazole, substituted isothiazole, substituted oxazole, substituted isoxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazole, substituted benzoimidazole, substituted benzofuran, substituted benzothiophene, substituted isobenzothiophene, substituted benzoxazole, substituted isobenzoxazole, substituted triazole, substituted oxadiazole, substituted triazine, substituted dibenzofuran, and substituted dibenzothiophene may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_1$-$C_{60}$ alkenyl group, a $C_1$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), or —B($Q_{406}$)($Q_{407}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic heterocondensed polycyclic group, —N($Q_{411}$)($Q_{412}$), —Si($Q_{413}$)($Q_{414}$)($Q_{415}$), and —B($Q_{416}$)($Q_{417}$); and —N(Q$_{421}$)(Q$_{422}$), —Si(Q$_{423}$)(Q$_{424}$)(Q$_{425}$), and —B(Q$_{426}$)(Q$_{427}$);

L$_{401}$ may be an organic ligand;

xc1 may be 1, 2, or 3; and xc2 may be 0, 1, 2, or 3.

Descriptions of Q$_{401}$ to Q$_{407}$, Q$_{411}$ to Q$_{417}$, and Q$_{421}$ to Q$_{427}$ may be understood by referring to the description provided herein in connection with Q$_1$.

L$_{401}$ may be a monovalent, divalent, or trivalent organic ligand. For example, L$_{401}$ may be selected from a halogen ligand (for example, Cl and/or F), a diketone ligand (for example, acetylacetonate, 1,3-diphenyl-1,3-propanedionate, 2,2,6,6-tetramethyl-3,5-heptanedionate, and/or hexafluoroacetonate), a carboxylic acid ligand (for example, picolinate, dimethyl-3-pyrazolecarboxylate, and/or benzoate), a carbon monooxide ligand, an isonitrile ligand, a cyano ligand, and a phosphorous ligand (for example, phosphine and/or phosphite), but is not limited thereto.

When A$_{401}$ in Formula 401 has two or more substituents, the substituents of A$_{401}$ may bind to each other to form a saturated or unsaturated ring.

When A$_{402}$ in Formula 401 has two or more substituents, the substituents of A$_{402}$ may bind to each other to form a saturated or unsaturated ring.

When xc1 in Formula 401 is two or more, a plurality of ligands

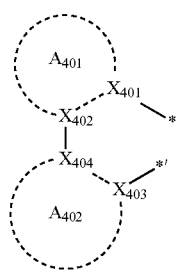

in Formula 401 may be identical to or different from each other. When xc1 in Formula 401 is two or more, A$_{401}$ and/or A$_{402}$ of one ligand may be respectively connected to A$_{401}$ and/or A$_{402}$ of other neighboring ligands, either directly (e.g., via a chemical bond) or via a linker (for example, a C$_1$-C$_5$ alkylene group, —N(R')— (where R' may be a C$_1$-C$_{10}$ alkyl group or a C$_6$-C$_{20}$ aryl group), and/or —C(═O)—) therebetween.

The phosphorescent dopant may include at least one selected from Compounds PD1 to PD74 below, but is not limited thereto:

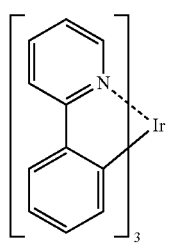

PD1

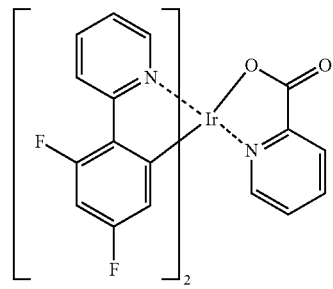

PD2

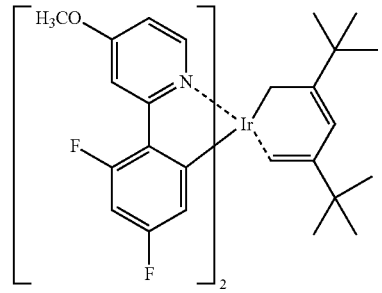

PD3

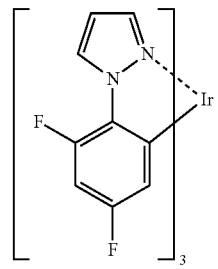

PD4

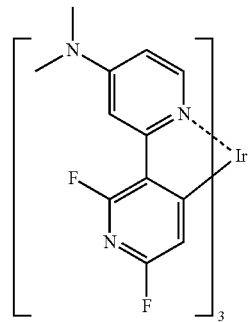

PD5

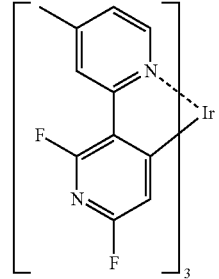

PD6

PD7 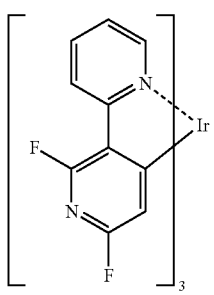
PD8 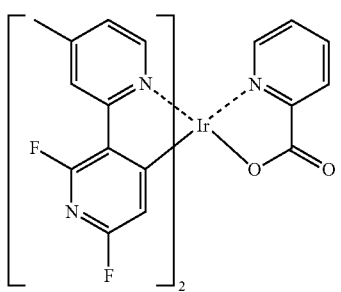
PD9 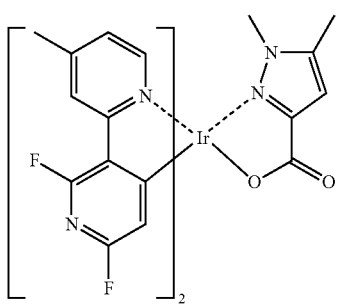
PD10 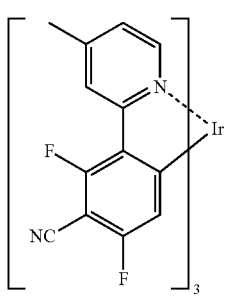
PD11 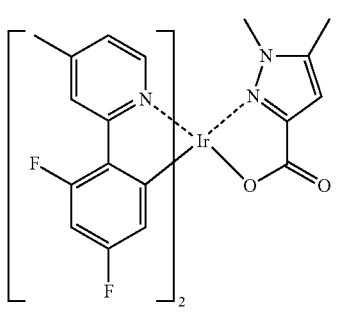
PD12 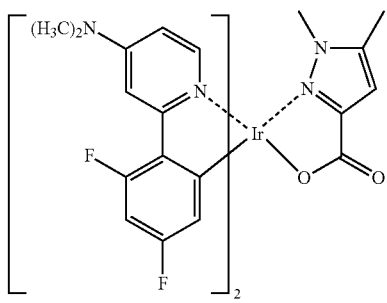
PD13 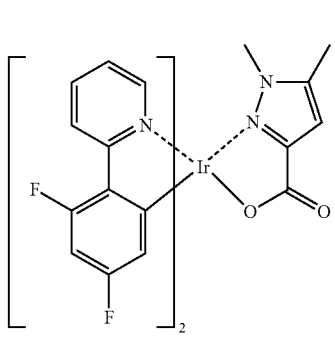
PD14 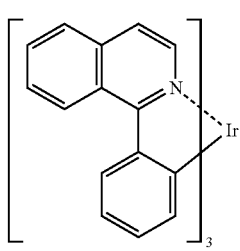
PD15 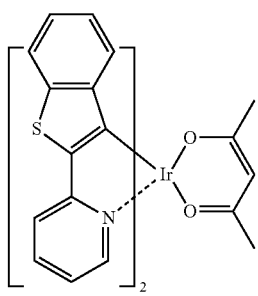
PD16 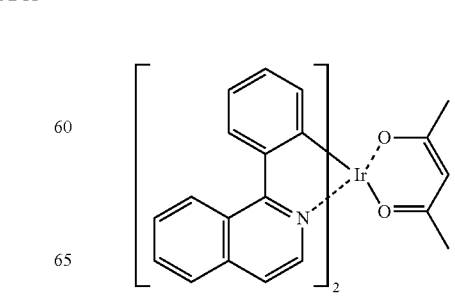

PD17
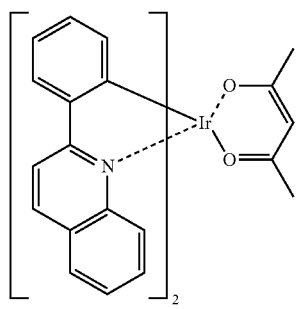
PD18
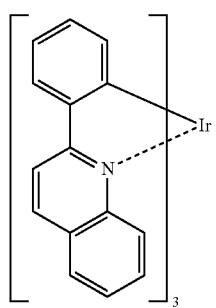
PD19
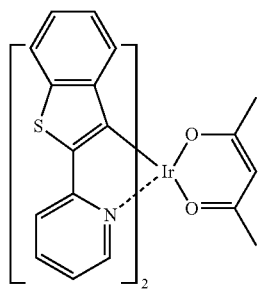
PD20
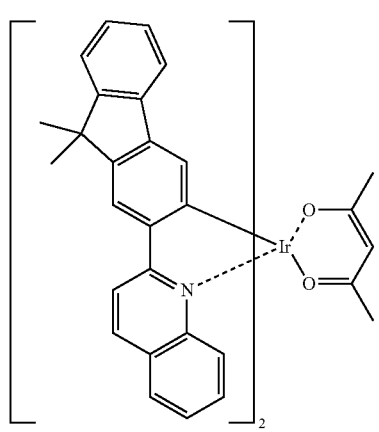
PD21
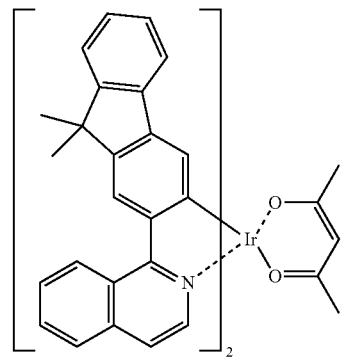
PD22
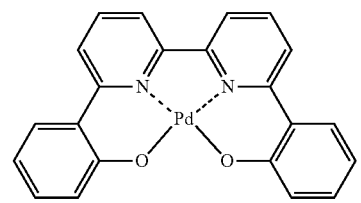
PD23
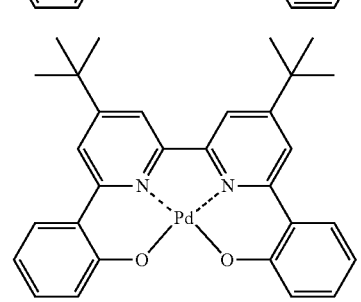
PD24
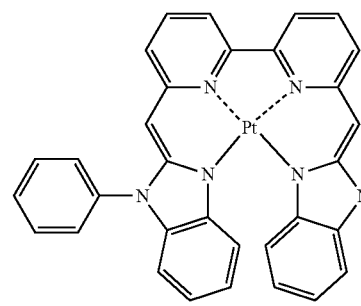
PD25
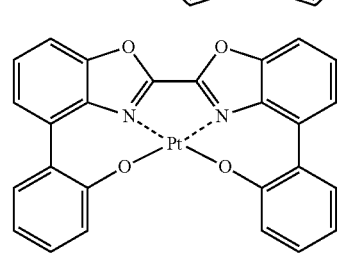
PD26
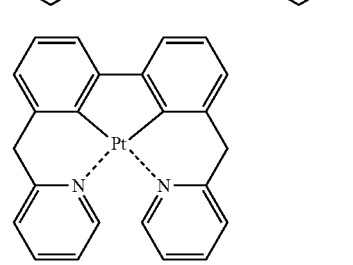

103
-continued
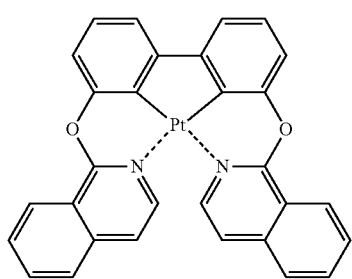
PD27
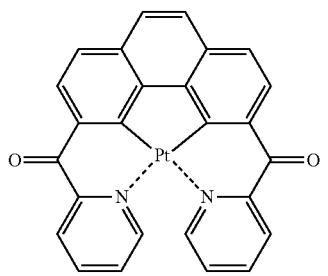
PD28
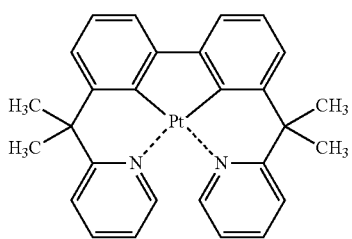
PD29
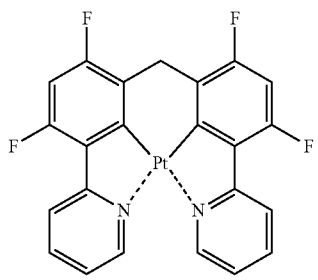
PD30
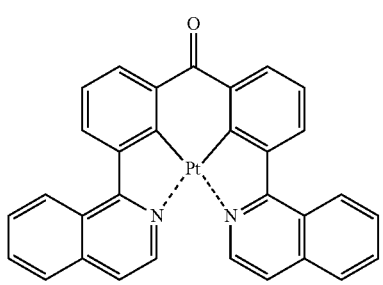
PD31
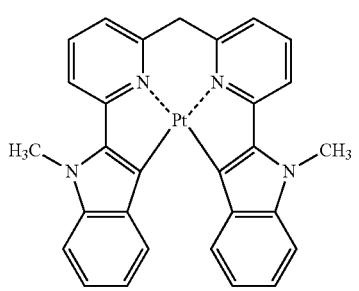
PD32
104
-continued
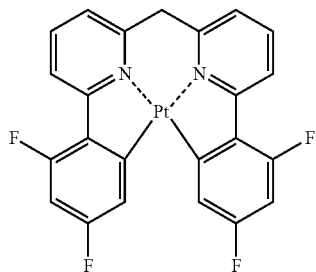
PD33
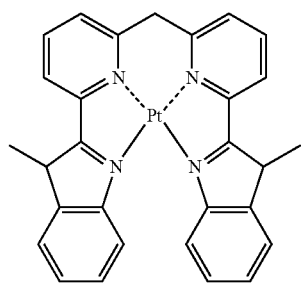
PD34
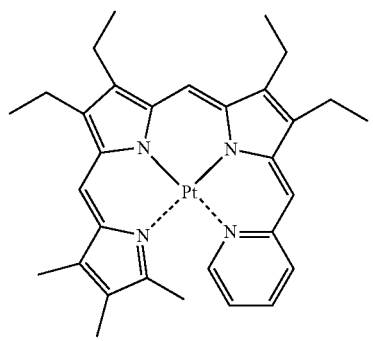
PD35
PD36
PD37

PD38 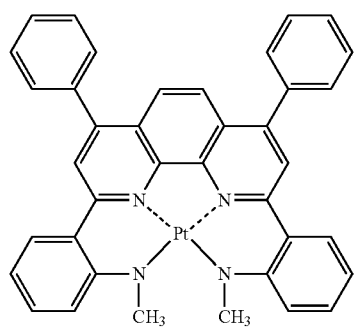
PD39 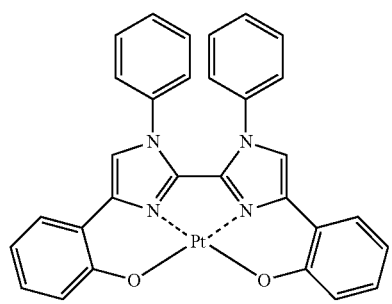
PD40 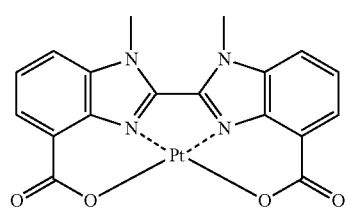
PD41 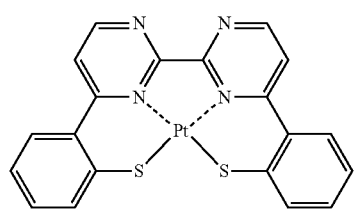
PD42 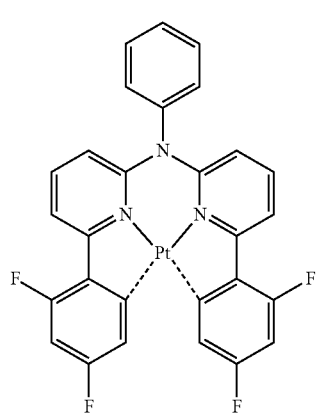
PD43 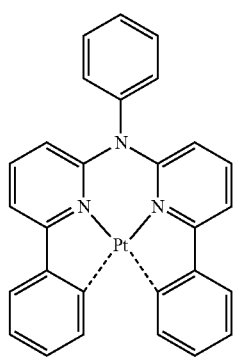
PD44 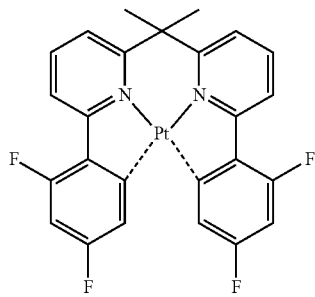
PD45 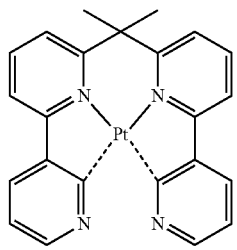
PD46 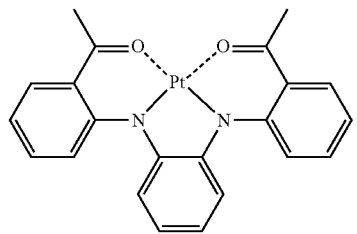
PD47 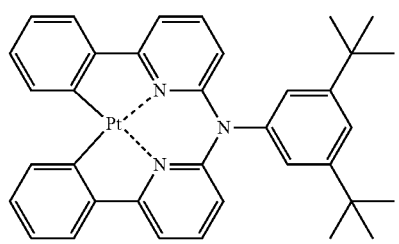
PD48 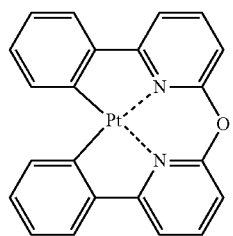

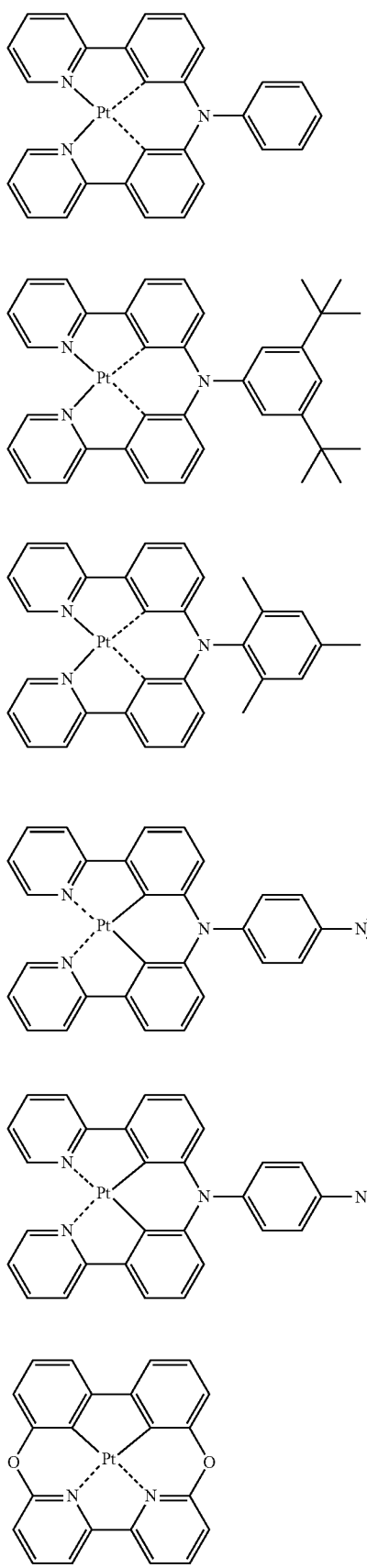
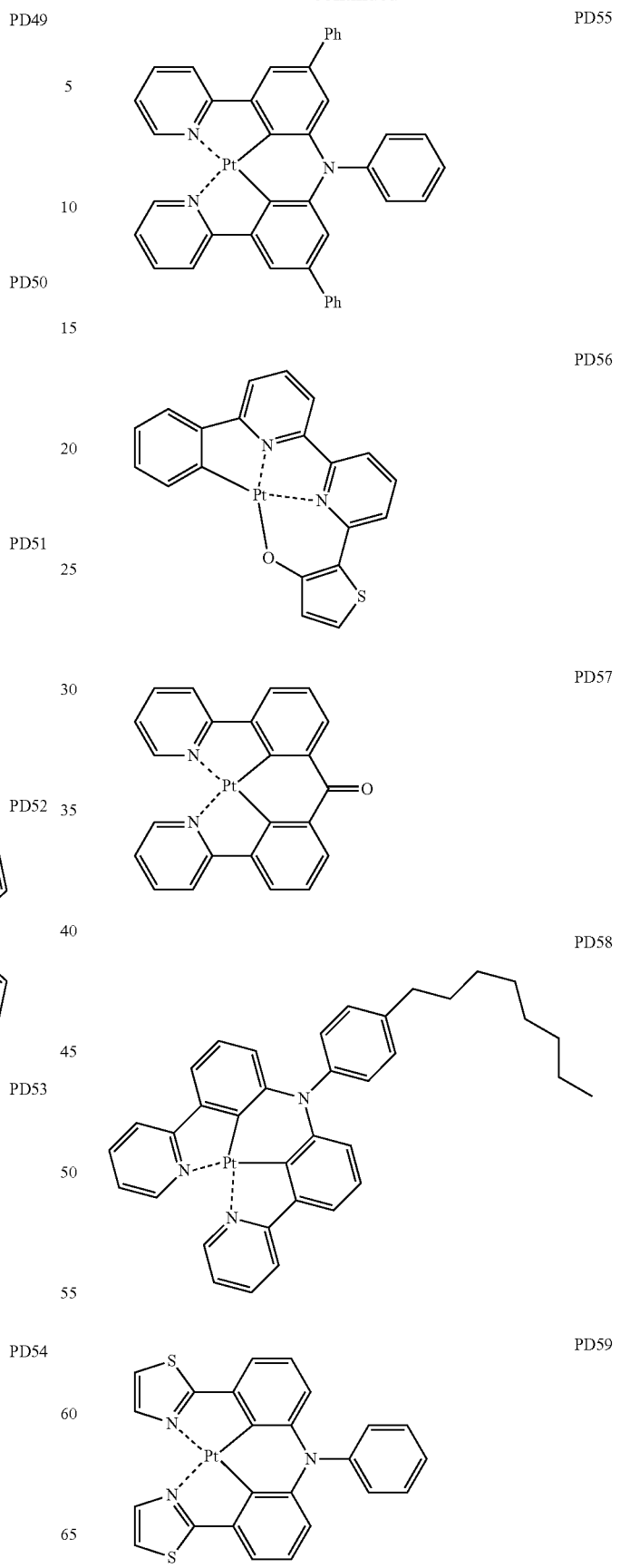

PD60 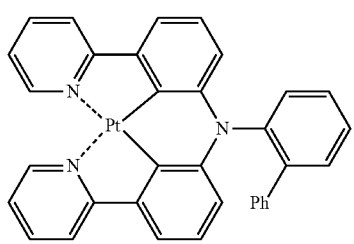
PD61 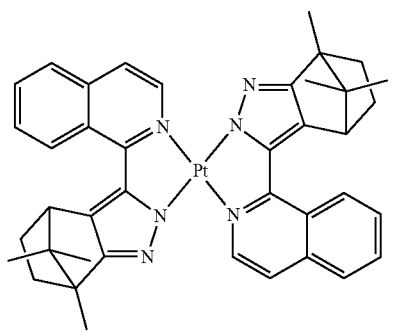
PD62 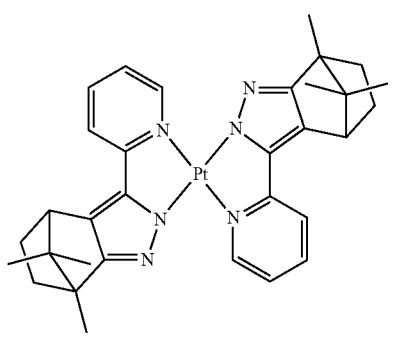
PD63 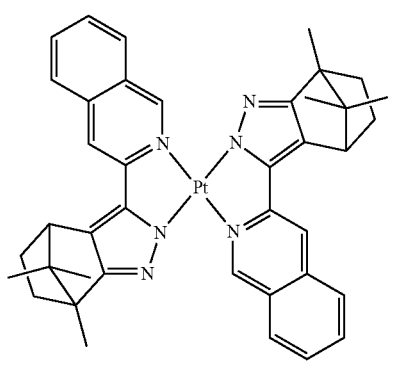
PD64 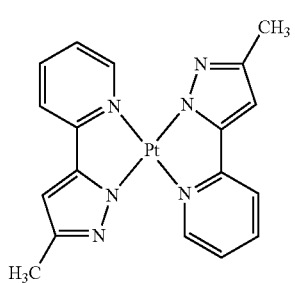
PD65 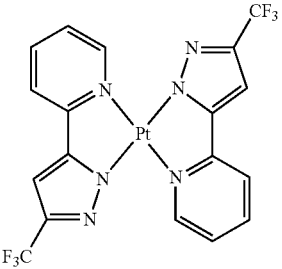
PD66 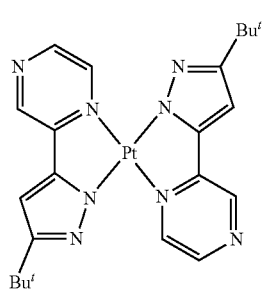
PD67 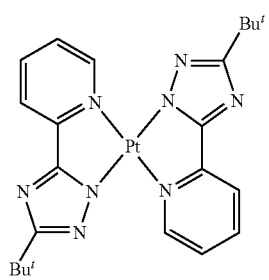
PD68 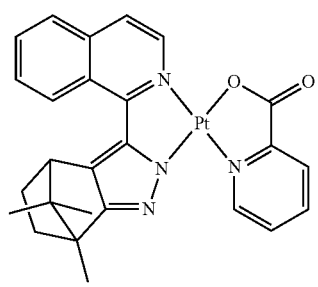
PD69 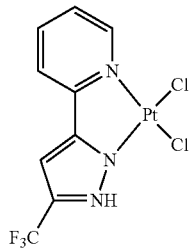

-continued
PD70
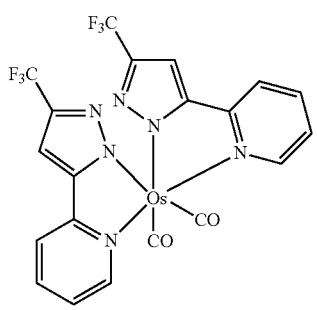
PD71
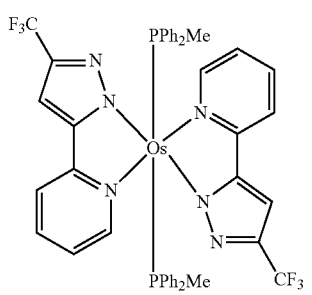
PD72
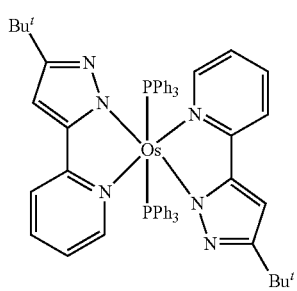
-continued
PD73
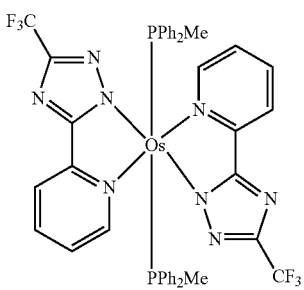
PD74
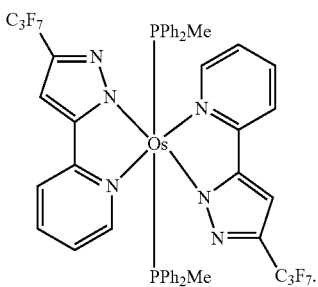
In some embodiments, the phosphorescent dopant may include PtOEP:
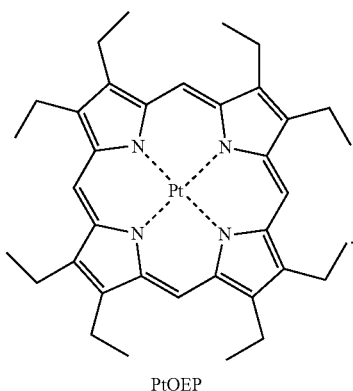
PtOEP
The fluorescent dopant may include at least one selected from DPVBi, DPAVBi, TBPe, DCM, DCJTB, Coumarin 6, and C545T.
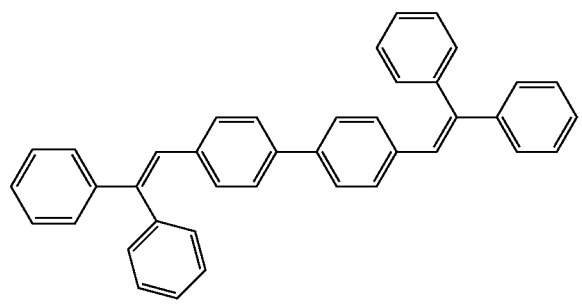
DPVBi

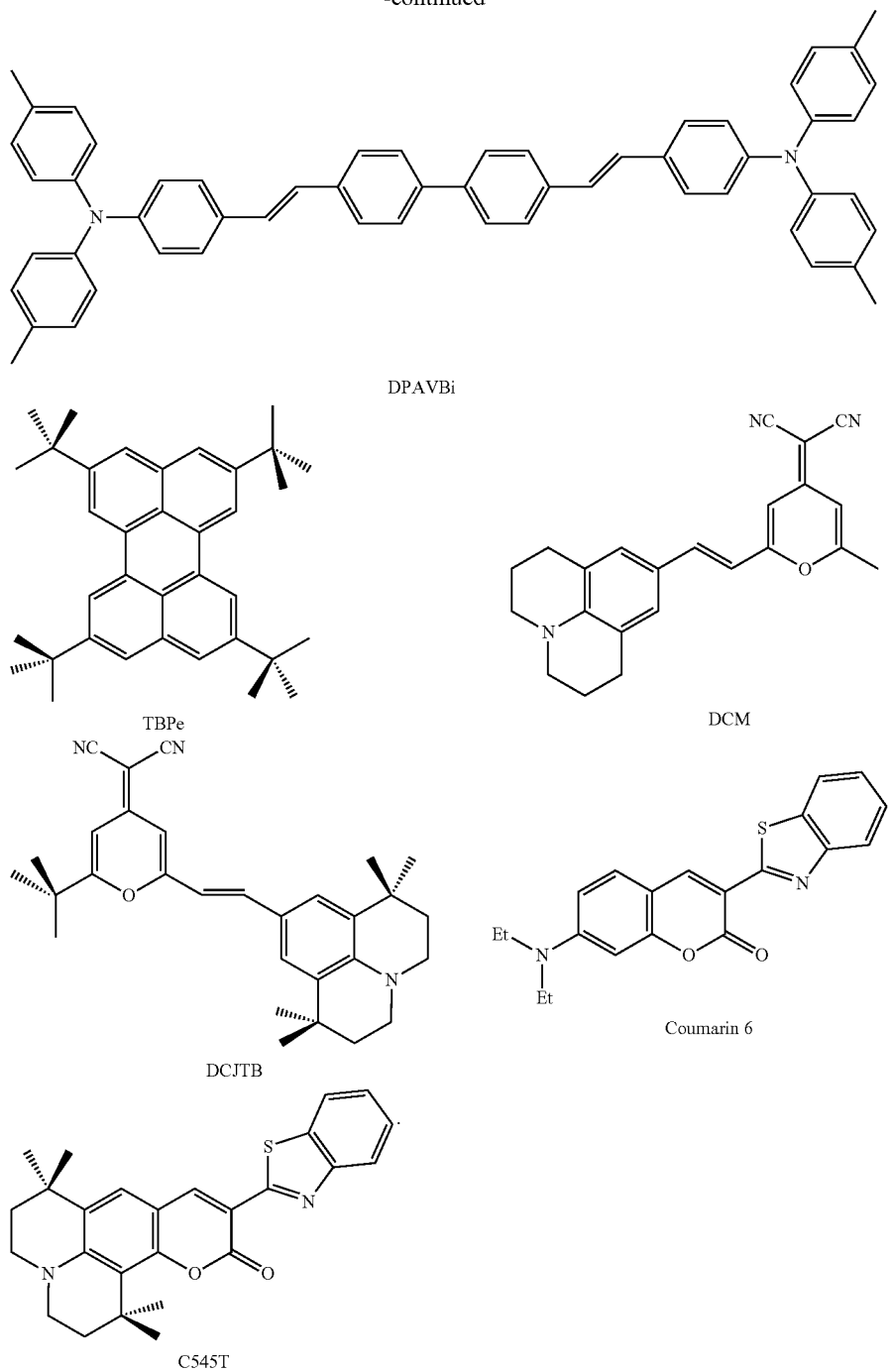

DPAVBi

TBPe

DCM

DCJTB

Coumarin 6

C545T

In some embodiments, the fluorescent dopant may include a compound represented by Formula 501 below.

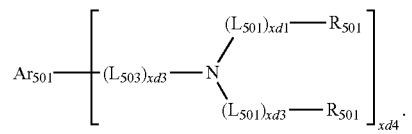

Formula 501

In Formula 501, $Ar_{501}$ may be selected from a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) (where $Q_{501}$ to $Q_{503}$ are each independently selected from hydrogen, a $C_1$-$C_{60}$ alkyl group, a $C_2$-$C_{60}$ alkenyl group, a $C_1$-$C_{60}$ aryl group, and a $C_1$-$C_{60}$ heteroaryl group);

$L_{501}$ to $L_{503}$ may be the same (or substantially the same) as defined in connection with $L_{201}$;

$R_{501}$ and $R_{502}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

xd1 to xd3 may be each independently selected from 0, 1, 2, and 3; and xd4 may be selected from 1, 2, 3, and 4.

The fluorescent dopant may include at least one selected from Compounds FD1 to FD9:

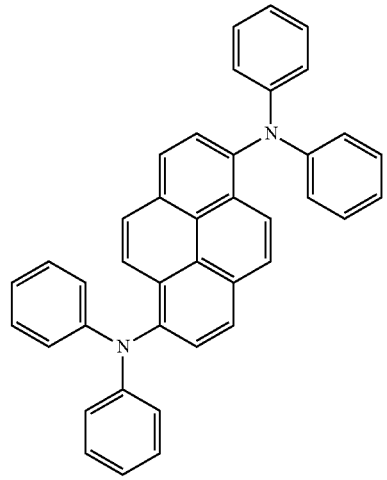
FD1

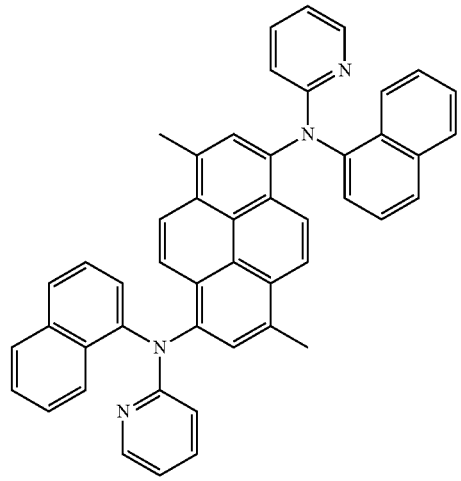
FD2

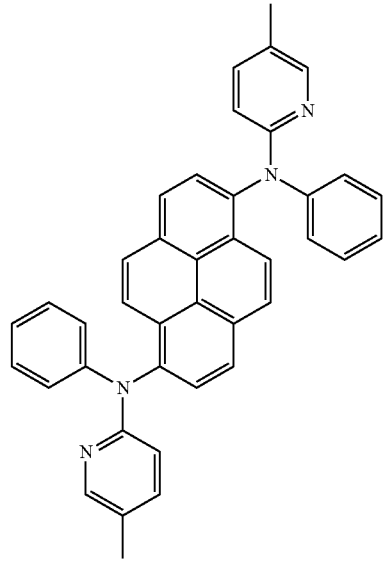
FD3

-continued
FD4
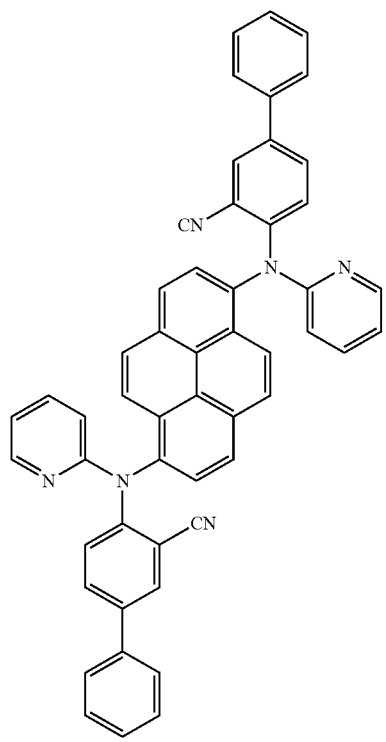
FD6
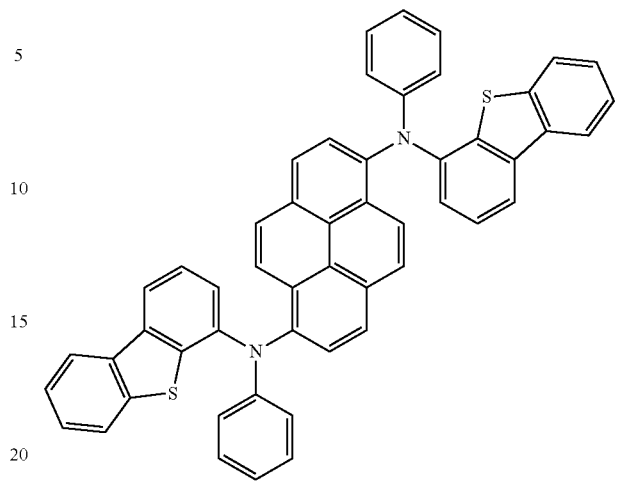
FD7
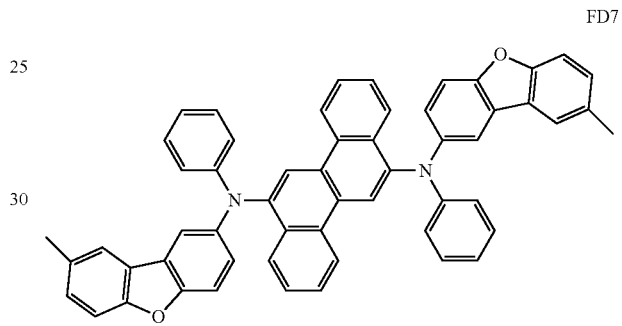
FD8
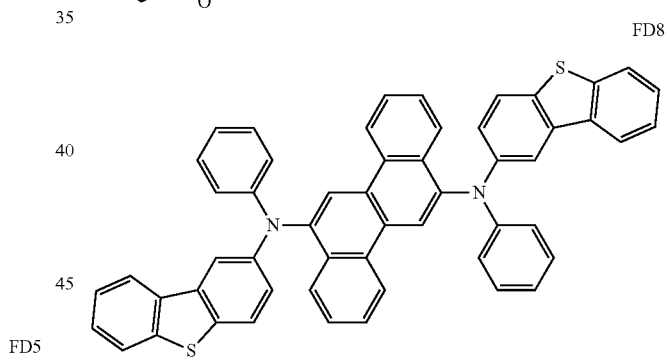
FD5
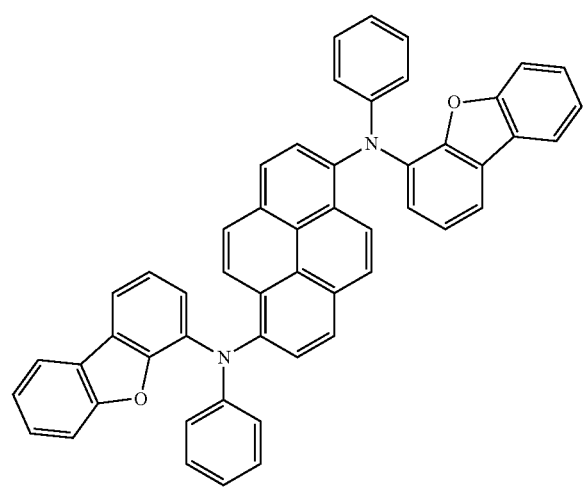
Compound FD9
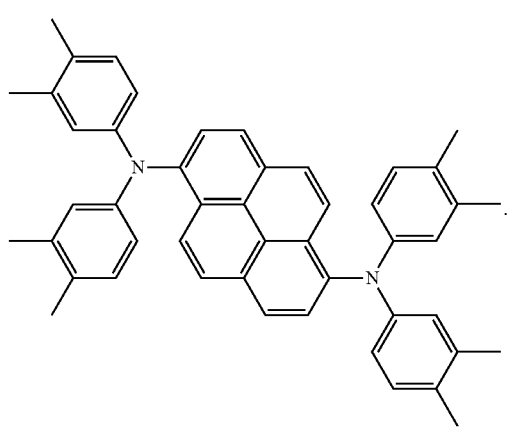

An amount of the dopant in the emission layer may be, in general, in a range of about 0.01 to about 15 parts by weight based on 100 parts by weight of the host, but is not limited thereto.

A thickness of the emission layer may be in a range of about 100 Å to about 1000 Å, for example, about 200 Å to about 600 Å. When the thickness of the emission layer is within this range, excellent light-emission characteristics may be obtained without a substantial increase in driving voltage.

An electron transport region may be positioned on the emission layer.

The electron transport region may include at least one selected from a hole blocking layer, an electron transport layer (ETL), and an electron injection layer, but is not limited thereto.

For example, the electron transport region may include an electron transport layer alone, or may have a structure of electron transport layer/electron injection layer or a structure of hole blocking layer/electron transport layer/electron injection layer, wherein the layers of each structure are sequentially stacked from the emission layer in the stated order, but the structure of the electron transport region is not limited thereto.

According to one or more embodiments, the organic layer 150 of the organic light-emitting device includes an electron transport region between the emission layer and the second electrode 190, wherein the electron transport region may include at least one selected from the condensed cyclic compounds represented by one selected from Formulae 1-1 or 1-2.

The electron transport region may include a hole blocking layer. When the emission layer includes a phosphorescent dopant, the hole blocking layer may be formed to prevent or reduce the diffusion of excitons or holes into an electron transport layer.

When the electron transport region includes a hole blocking layer, the hole blocking layer may be formed on the emission layer by using one or more suitable methods, such as vacuum deposition, spin coating casting, a LB method, ink-jet printing, laser-printing, and/or laser-induced thermal imaging. When the hole blocking layer is formed by vacuum deposition and/or spin coating, deposition and coating conditions for the hole blocking layer may be similar to the deposition and coating conditions for the hole injection layer.

The hole blocking layer may include, for example, at least one selected from BCP and Bphen, but is not limited thereto.

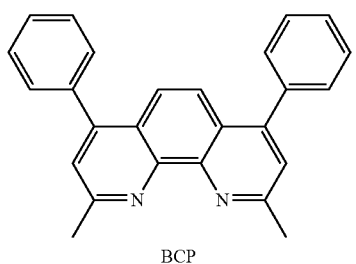

BCP

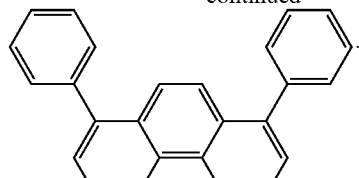

Bphen

A thickness of the hole blocking layer may be in a range of about 20 Å to about 1000 Å, for example, about 30 Å to about 300 Å. When the thickness of the hole blocking layer is within these ranges, the hole blocking layer may have improved hole blocking ability without a substantial increase in driving voltage.

The electron transport region may include an electron transport layer. The electron transport layer may be formed on the emission layer or the hole blocking layer by using one or more suitable methods, such as vacuum deposition, spin coating casting, a LB method, ink-jet printing, laser-printing, and/or laser-induced thermal imaging. When an electron transport layer is formed by vacuum deposition or spin coating, deposition and coating conditions for the electron transport layer may be similar to the deposition and coating conditions for the hole injection layer.

The electron transport layer may further include at least one selected from BCP, Bphen, Alq$_3$, Balq, TAZ, and NTAZ.

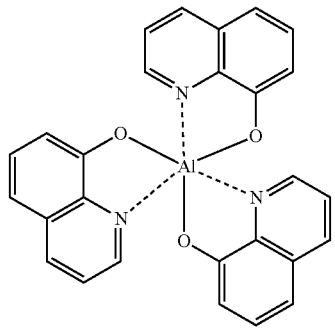

Alq$_3$

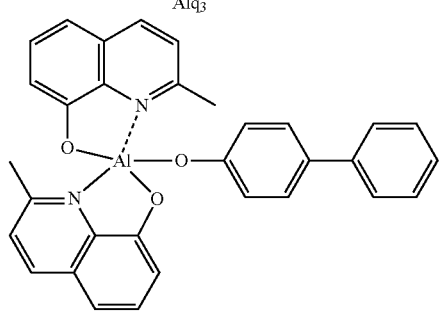

BAlq

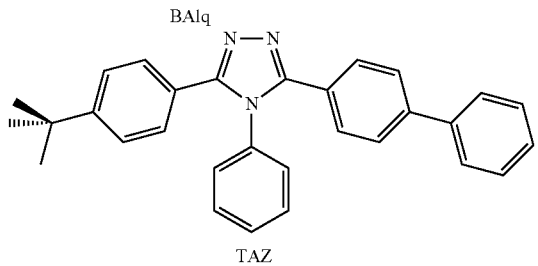

TAZ

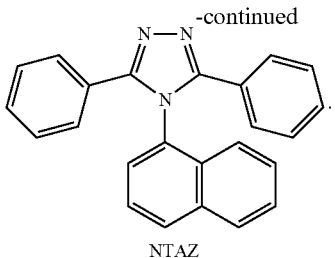

NTAZ

In some embodiments, the electron transport layer may include at least one compound selected from a compound represented by Formula 601 and a compound represented by Formula 602 illustrated below:

$$Ar_{601}\text{-}[(L_{601})_{xe1}\text{-}E_{601}]_{xe2} \quad \text{Formula 601}$$

In Formula 601, $Ar_{601}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene group, a heptalene group, a fluorene group, a spiro-fluorene group, a benzofluorene group, a dibenzofluorene group, a phenalene group, a phenanthrene group, a anthracene group, a fluoranthene group, a triphenylene group, a pyrene group, a chrysene group, a naphthacene group, a picene group, a perylene group, a pentaphene group, and an indenoanthracene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (where $Q_{301}$ to $Q_{303}$ are each independently selected from hydrogen, a $C_1$-$C_{60}$ alkyl group, a $C_2$-$C_{60}$ alkenyl group, a $C_1$-$C_{60}$ aryl group, and a $C_1$-$C_{60}$ heteroaryl group);

$L_{601}$ may be the same (or substantially the same) as described in connection with $L_{201}$;

$E_{601}$ may be selected from:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a furinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

xe1 may be selected from 0, 1, 2, and 3; and xe2 may be selected from 1, 2, 3, and 4.

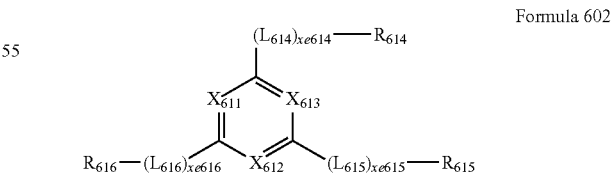

Formula 602

In Formula 602, $X_{611}$ may be N or C-$(L_{611})_{xe611}$-$R_{611}$; $X_{612}$ may be N or C-$(L_{612})_{xe612}$-$R_{612}$; $X_{613}$ may be N or C-$(L_{613})_{xe613}$-$R_{613}$, and at least one of $X_{611}$ to $X_{613}$ may be N;

$L_{611}$ to $L_{616}$ may be each independently the same (or substantially the same) as described in connection with $L_{201}$;

$R_{611}$ to $R_{616}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 may be each independently selected from 0, 1, 2, and 3.

The compound represented by Formula 601 and the compound represented by Formula 602 may each independently be selected from Compounds ET1 to ET15 illustrated below.

ET1

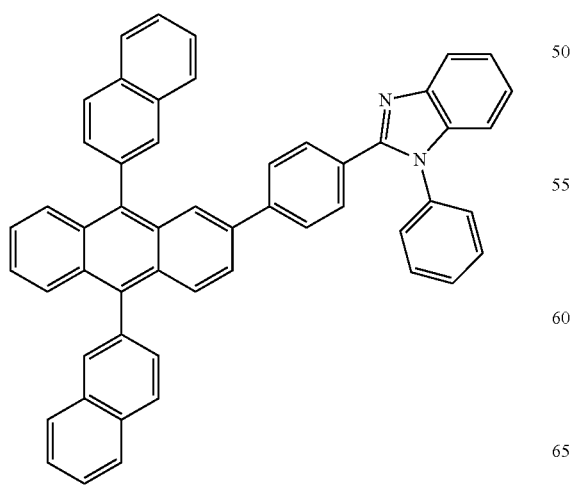

-continued

ET2

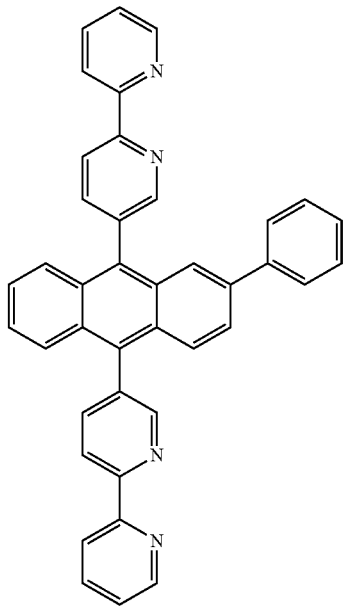

ET3

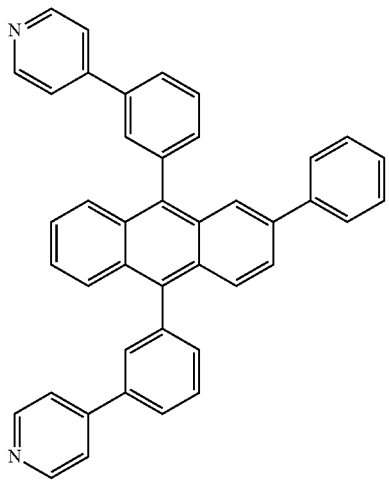

ET4

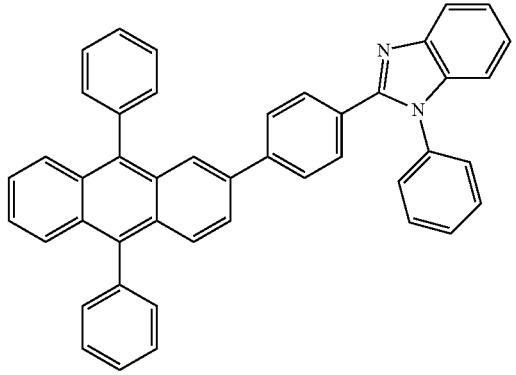

ET5
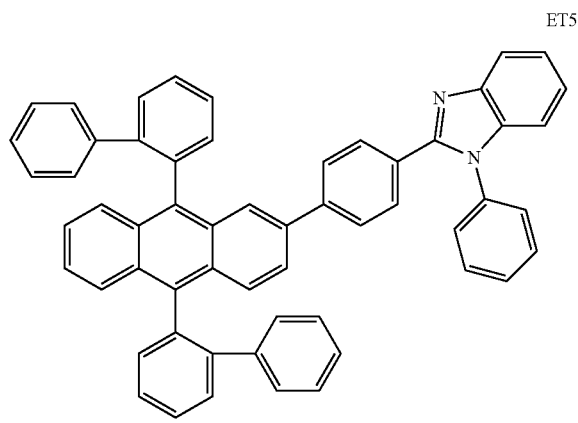
ET6
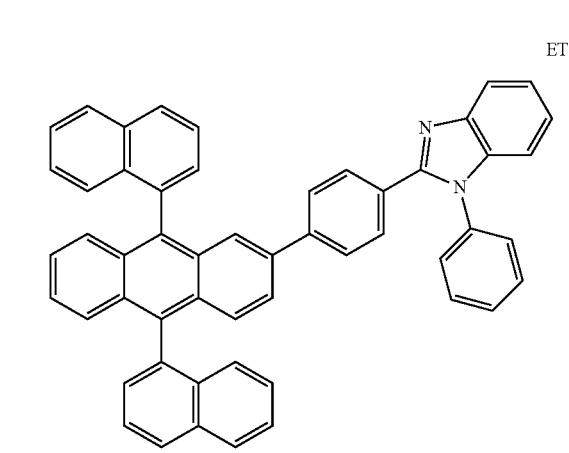
ET7
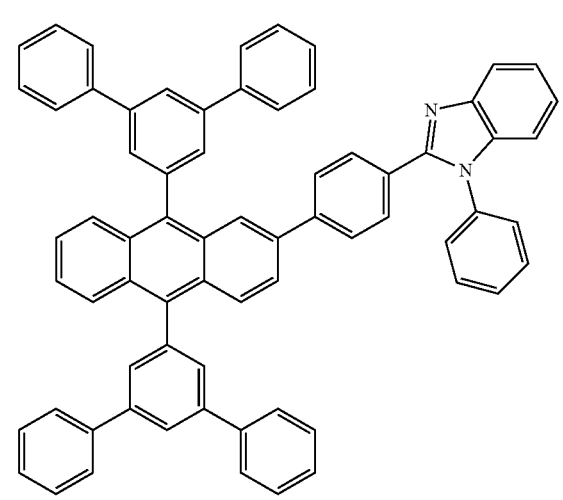
ET8
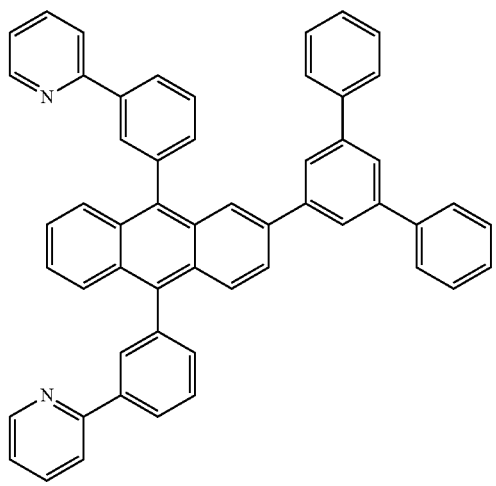
ET9
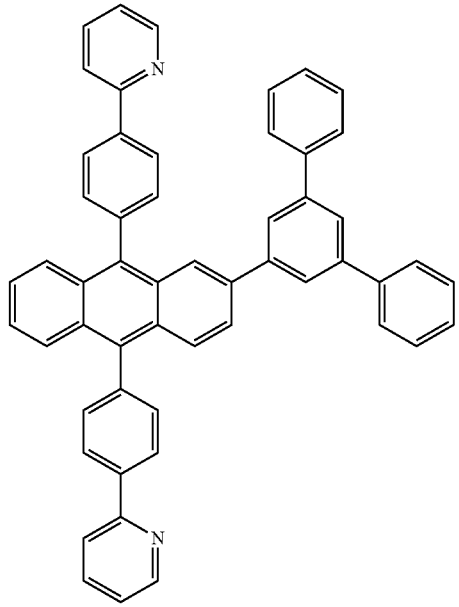
ET10
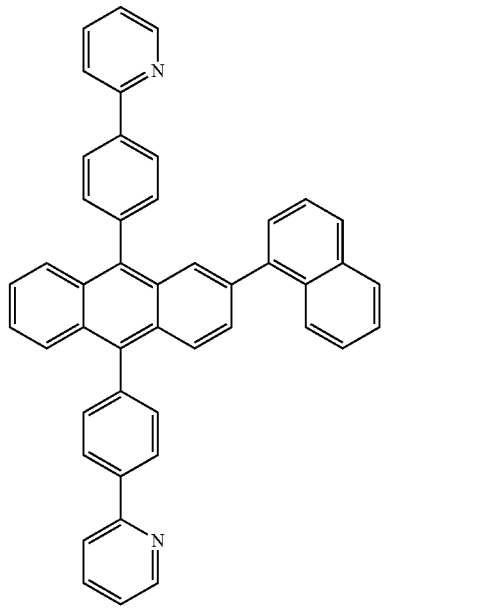

ET11

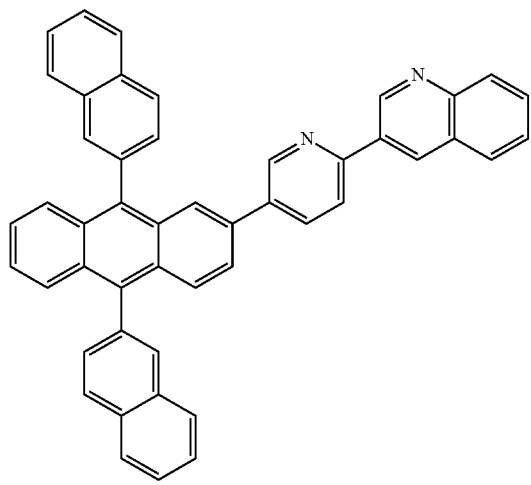

ET12

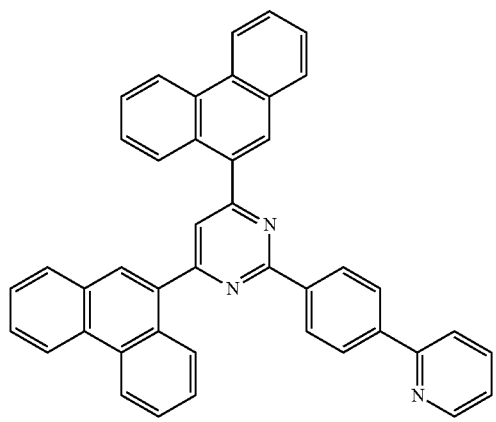

ET13

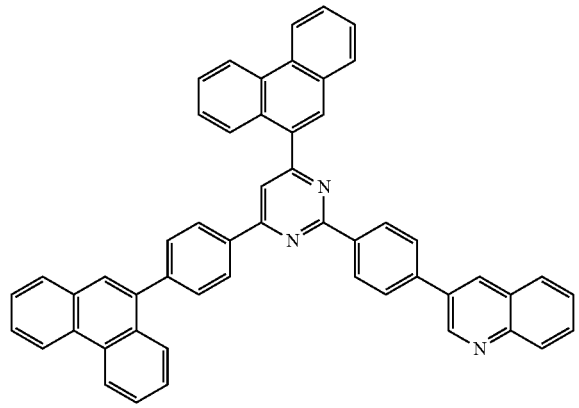

ET14

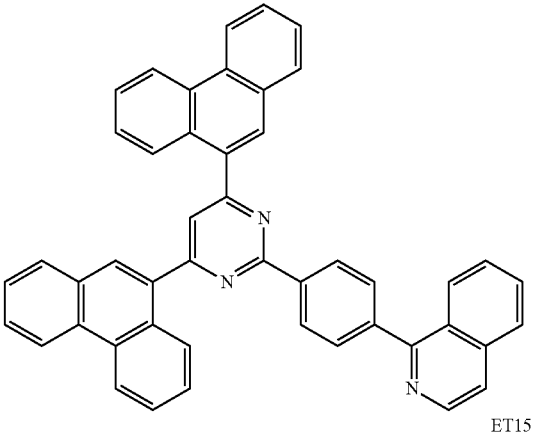

ET15

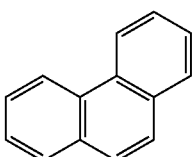

A thickness of the electron transport layer may be in a range of about 100 Å to about 1000 Å, for example, about 150 Å to about 500 Å. When the thickness of the electron transport layer is within these ranges, the electron transport layer may have satisfactory electron transport characteristics without a substantial increase in driving voltage.

In some embodiments, the electron transport layer may further include, in addition to the materials described above, a metal-containing material.

The metal-containing material may include a Li complex. The Li complex may include, for example, Compound ET-D1 (lithium quinolate, LiQ) and/or ET-D2.

ET-D1

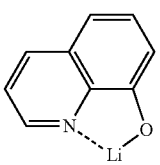

ET-D2

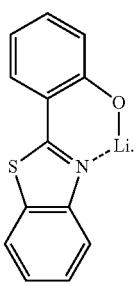

The electron transport region may include an electron injection layer that facilitates the injection of electrons from the second electrode 190.

The electron injection layer may be formed on the electron transport layer by using one or more suitable methods, such as vacuum deposition, spin coating casting, a LB method, ink-jet printing, laser-printing, and/or laser-induced thermal imaging. When the electron injection layer is formed by vacuum deposition and/or spin coating, deposition and coating conditions for the electron injection layer may be similar to the deposition and coating conditions for the hole injection layer.

The electron injection layer may include at least one selected from LiF, NaCl, CsF, $Li_2O$, BaO, and LiQ.

A thickness of the electron injection layer may be in a range of about 1 Å to about 100 Å, about 3 Å to about 90 Å. When the thickness of the electron injection layer is within these ranges, the electron injection layer may have satisfactory electron injection characteristics without a substantial increase in driving voltage.

The second electrode 190 may be positioned on the organic layer 150 having such the above-described structure. The second electrode 190 may be a cathode that is an electron injection electrode, and in this regard, a material for forming the second electrode 190 may be a material having a low work function, for example, a metal, an alloy, an electrically conductive compound, or a mixture thereof. Non-limiting examples of the material for forming the second electrode 190 include lithium (Li), magnesium (Mg), aluminum (Al), aluminum-lithium (Al—Li), calcium (Ca), magnesium-indium (Mg—In), and magnesium-silver (Mg—Ag). In some embodiments, the material for forming the second electrode 190 may be ITO and/or IZO. The second electrode 190 may be a reflective electrode, a semi-transmissive electrode, or a transmissive electrode.

Hereinbefore, the organic light-emitting device has been described with reference to the drawing, but embodiments of the present disclosure are not limited thereto.

A $C_1$-$C_{60}$ alkyl group used herein refers to a linear or branched aliphatic hydrocarbon monovalent group having 1 to 60 carbon atoms, and non-limiting examples thereof include a methyl group, an ethyl group, a propyl group, an isobutyl group, a sec-butyl group, a ter-butyl group, a pentyl group, an iso-amyl group, and a hexyl group. A $C_1$-$C_{60}$ alkylene group used herein refers to a divalent group having the same structure as the $C_1$-$C_{60}$ alkyl group.

A $C_1$-$C_{60}$ alkoxy group used herein refers to a monovalent group represented by —$OA_{101}$ (where $A_{101}$ is the $C_1$-$C_{60}$ alkyl group), and non-limiting examples thereof include a methoxy group, an ethoxy group, and an isopropyloxy group.

A $C_2$-$C_{60}$ alkenyl group used herein refers to a hydrocarbon group having at least one carbon-carbon double bond at one or more positions along a carbon chain of the $C_2$-$C_{60}$ alkyl group (e.g., in the middle or at either terminal end of the $C_2$-$C_{60}$ alkyl group), and non-limiting examples thereof include an ethenyl group, a propenyl group, and a butenyl group. A $C_2$-$C_{60}$ alkylene group used herein refers to a divalent group having the same structure as the $C_2$-$C_{60}$ alkyl group.

A $C_2$-$C_{60}$ alkynyl group used herein refers to a hydrocarbon group having at least one carbon-carbon triple bond at one or more positions along a carbon chain of the $C_2$-$C_{60}$ alkyl group (e.g., in the middle or at either terminal end of the $C_2$-$C_{60}$ alkyl group), and non-limiting examples thereof include an ethynyl group and a propynyl group. A $C_2$-$C_{60}$ alkylene group used herein refers to a divalent group having the same structure as the $C_2$-$C_{60}$ alkyl group.

A $C_3$-$C_{10}$ cycloalkyl group used herein refers to a monovalent hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_1$-$C_{10}$ heterocycloalkyl group used herein refers to a monovalent monocyclic group having at least one heteroatom selected from N, O, P, and S as a ring-forming atom and 1 to 10 carbon atoms, and non-limiting examples thereof include a tetrahydrofuranyl group and a tetrahydrothiophenyl group. A $C_1$-$C_{10}$ heterocycloalkylene group used herein refers to a divalent group having the same structure as the $C_1$-$C_{10}$ heterocycloalkyl group.

A $C_3$-$C_{10}$ cycloalkenyl group used herein refers to a monovalent monocyclic group that has 3 to 10 carbon atoms, at least one double bond in the ring thereof, and does not have aromaticity, and non-limiting examples thereof include a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_1$-$C_{10}$ heterocycloalkenyl group used herein refers to a monovalent monocyclic group that has at least one heteroatom selected from N, O, P, and S as a ring-forming atom, 1 to 10 carbon atoms, and at least one double bond in its ring. Non-limiting examples of the $C_1$-$C_{10}$ heterocycloalkenyl group include a 2,3-dihydrofuranyl group and a 2,3-dihydrothiophenyl group. A $C_1$-$C_{10}$ heterocycloalkenylene group used herein refers to a divalent group having the same structure as the $C_1$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and/or the $C_6$-$C_{60}$ arylene group include two or more rings, the rings may be respectively fused (e.g., coupled) to each other.

A $C_1$-$C_{60}$ heteroaryl group used herein refers to a monovalent group having a carbocyclic aromatic system that has at least one heteroatom selected from N, O, P, and S as a ring-forming atom, and 1 to 60 carbon atoms. A $C_1$-$C_{60}$ heteroarylene group used herein refers to a divalent group having a carbocyclic aromatic system that has at least one hetero atom selected from N, O, P, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and/or the $C_1$-$C_{60}$ heteroarylene group include two or more rings, the rings may be respectively fused (e.g., coupled) to each other.

A $C_6$-$C_{60}$ aryloxy group used herein refers to a monovalent group represented by —$OA_{102}$ (where $A_{102}$ is the $C_6$-$C_{60}$ aryl group), and a $C_6$-$C_{60}$ arylthio group used herein refers to a monovalent group represented by —$SA_{103}$ (where $A_{103}$ is the $C_6$-$C_{60}$ aryl group).

A monovalent non-aromatic condensed polycyclic group used herein refers to a monovalent group that has two or more rings condensed (e.g., coupled) to each other, only carbon atoms as ring-forming atoms (for example, having 8 to 60 carbon atoms), and does not have overall aromaticity. A non-limiting example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group used herein refers to a monovalent group that has two or more rings condensed (e.g., coupled) to each other, has at least one heteroatom selected from N, O P, and S as a ring-forming atom, and carbon atoms (for example, having 1 to 60 carbon atoms), and does not have overall aromaticity. A non-limiting example of the monovalent non-aromatic condensed heteropolycyclic group is a carbazolyl group. A divalent non-aromatic condensed heteropolycyclic group used herein refers to a divalent group having the same structure as the monovalent non-aromatic condensed heteropolycyclic group.

At least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —B($Q_{14}$)($Q_{15}$), and —N($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —B($Q_{24}$)($Q_{25}$), and —N($Q_{26}$)($Q_{27}$); and —Si($Q_{31}$)($Q_{32}$)($Q_{33}$), —B($Q_{34}$)($Q_{35}$) and —N($Q_{36}$)($Q_{37}$), where $Q_{11}$ to $Q_{17}$, $Q_{21}$ to $Q_{27}$ and $Q_{31}$ to $Q_{37}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{11}$)($Q_{12}$), —B($Q_{13}$)($Q_{14}$) and —Si($Q_{15}$)($Q_{16}$)($Q_{17}$);

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group and an imidazopyrimidinyl group;

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{21}$)($Q_{22}$), —B($Q_{23}$)($Q_{24}$), and —Si($Q_{25}$)($Q_{26}$)($Q_{27}$); and —N($Q_{31}$)($Q_{32}$), —B($Q_{33}$)($Q_{34}$), and —Si($Q_{35}$)($Q_{36}$)($Q_{37}$), where $Q_{11}$ to $Q_{17}$, $Q_{21}$ to $Q_{27}$ and $Q_{31}$ to $Q_{37}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, but embodiments of the present disclosure are not limited thereto.

The term "Ph" used herein refers to a phenyl group, the term "Me" used herein refers to a methyl group, the term "Et" used herein refers to an ethyl group, and the term "ter-Bu" or "Bu'" used herein refers to a tert-butyl group.

Hereinafter, an organic light-emitting device according to one or more embodiments of the present disclosure will be described in more detail with reference to Synthesis Examples and Examples. Here, the phrase "B was used instead of A" used in describing Synthesis Examples refers to a molar equivalent of A being identical to a molar equivalent of B.

EXAMPLE

Synthesis Example 1: Synthesis of Compound 1

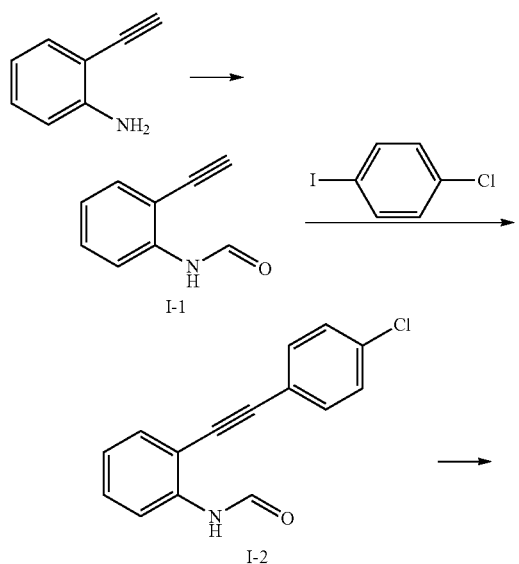

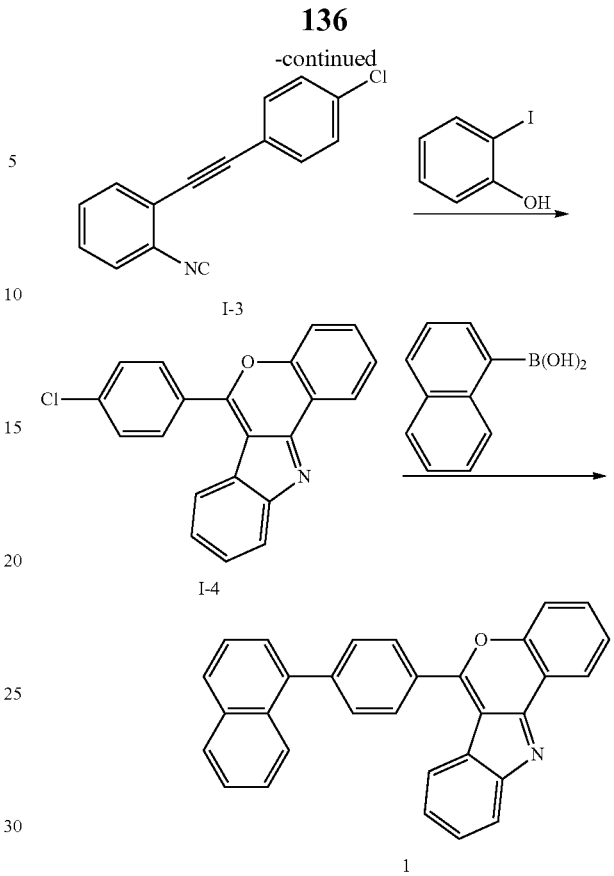

Synthesis of Intermediate I-2

Formic acid (1.21 mL, 32.0 mmol) was added to anhydrous acetate (1.08 mL, 11.4 mmol), and then, the resulting mixture was stirred for 10 minutes at room temperature. o-ethynylanyline (1.07 g, 9.13 mmol) dissolved in 30 mL of dichloromethane was added thereto, and then, the result was stirred for 1 hour. A solvent was removed from the resulting mixed solution to obtain Intermediate I-1.

Intermediate I-1 (1.32 g, 9.13 mmol), 1-chloro-4-iodobenzene (1.81 g, 7.61 mmol), Et$_3$N (28 mL), Pd(PPh$_3$)$_2$Cl$_2$ (260 mg, 0.38 mmol), and CuI (76 mg, 0.38 mmol) were added thereto, and then, the result was stirred for 12 hours at room temperature. The obtained reaction solution was filtered via celite, and then, subjected to an extraction process using an ammonium chloride solution and a chloroform solution. The obtained solvent was removed therefrom by evaporation and the residual was separation-purified by silicagel column chromatography to obtain 1.10 g (yield of 47%) of Intermediate I-2. The obtained compound was confirmed by LC-MS. C$_{15}$H$_{10}$ClNO: M+1 256.0

Synthesis of Intermediate I-3

Intermediate I-2 (4.43 g, 20.0 mmol) and 14 mL of Et$_3$N were dissolved in 20 mL of THF, and then, at a temperature of 0° C., phosphoryl chloride (2.8 mL, 30 mmol) was added dropwise thereto. After one hour of stirring, the resulting reaction solution was subjected to an extraction process using a NaHCO$_3$ aqueous solution and diethylether. The obtained solvent was removed therefrom by evaporation, and the residual was separation purified by alumina column chromatography to obtain 2.85 g of Intermediate I-3 (yield of 50%). The obtained compound was confirmed by LC-MS. C$_{15}$H$_8$ClN: M+1 238.0

Synthesis of Intermediate I-4

2-iodophenol (2.20 g, 10.0 mmol), Pd(OAc)$_2$ (22 mg, 0.10 mmol), Ad$_2$P$_n$Bu (72 mg, 0.20 mmol), and Cs$_2$CO$_3$ (9.77 g, 30.0 mmol) were dissolved in 50 mL of toluene, and then, the resulting mixture was stirred at a temperature of 100° C. for 10 minutes, and then, Intermediate I-3 (2.37 g, 10.0 mmol) was slowly added dropwise thereto. After one hour of stirring, the resulting reaction solution was subjected to an extraction process using NaHCO$_3$ aqueous solution and diethylether. The obtained solvent was removed therefrom by evaporation, and the residual was separation-purified by silicagel column chromatography to obtain 2.37 g (yield of 72%) of Intermediate I-4. The obtained compound was confirmed by LC-MS. C$_{21}$H$_{12}$ClNO: M+1 330.1

Synthesis of Compound 1

3.29 g (10.0 mmol) of Intermediate I-4, 1.72 g (10 mmol) of 1-naphthaleneboronic acid, 0.46 g (0.5 mmol) of Pd$_2$(dba)$_3$, 0.2 g (1.0 mmol) of PtBu$_3$, and 4.89 g (15 mmol) of cesium carbonate were dissolved in 50 mL of 1,4-dioxane solution, and then, the result was stirred at a temperature of 90° C. for 20 hours. The obtained reaction solution was cooled to room temperature, and then, 40 mL of water was added thereto and an extraction process was performed thereon by using 40 mL of ethylether three times. The collected organic layer was dried by using magnesium sulfate, and then, the residual obtained by drying using sulfate was separation-purified by separation-purified by silicagel column chromatography to obtain 2.87 g (yield of 68%) of Compound 1. The obtained compound was confirmed by MS/FAB and $^1$H NMR. C$_{31}$H$_{19}$NO cal. 421.15. found 421.14.

Synthesis Example 2: Synthesis of Compound 5

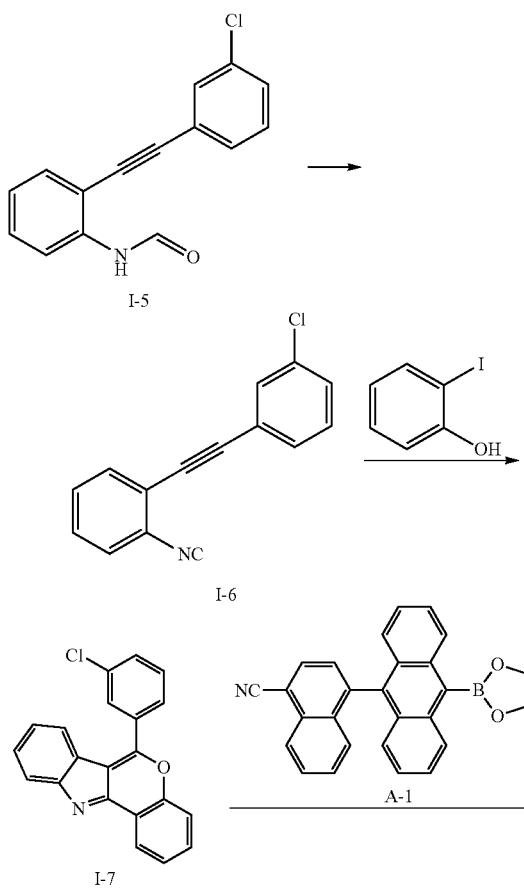

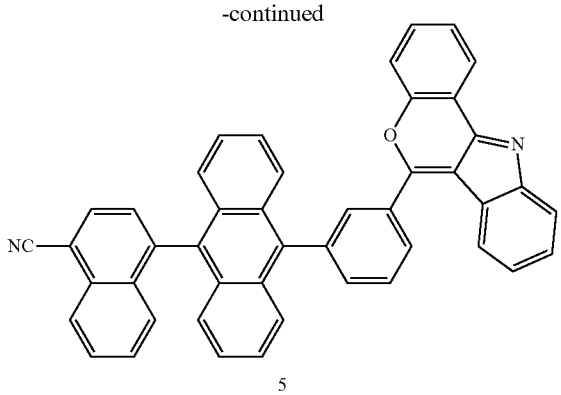

Synthesis of Intermediate I-5

2.40 g (yield of 60%) of Intermediate I-5 was obtained in the same (or substantially the same) manner as in synthesis of Intermediate I-2, except that 1-chloro-3-iodobenzene was used instead of 1-chloro-4-iodobenzene. The obtained compound was confirmed by LC-MS. C$_{15}$H$_{10}$ClNO: M+1 256.0

Synthesis of Intermediate I-6

2.80 g (yield of 59%) of Intermediate I-6 was obtained in the same (or substantially the same) manner as in synthesis of Intermediate I-3, except that Intermediate I-5 was used instead of Intermediate I-2. The obtained compound was confirmed by LC-MS. The obtained compound was confirmed by LC-MS. C$_{15}$H$_8$ClN: M+1 238.0

Synthesis of Intermediate I-7

2.31 g (yield of 70%) of Intermediate I-7 was obtained in the same (or substantially the same) manner as in synthesis of Intermediate I-4, except that Intermediate I-6 was used instead of Intermediate I-3. The obtained compound was confirmed by LC-MS. The obtained compound was confirmed by LC-MS. C$_{21}$H$_{12}$ClNO: M+1 330.1

Synthesis of Compound 5

4.11 g (yield of 66%) of Compound 5 was obtained in the same (or substantially the same) manner as in synthesis of Compound 1, except that Intermediate I-7 was used instead of Intermediate I-4 and Intermediate A-1 was used instead of 1-naphthaleneboronic acid. The obtained compound was confirmed by MS/FAB and $^1$H NMR. C$_{46}$H$_{26}$N$_2$O cal. 622.20. found 622.19.

Synthesis Example 3: Synthesis of Compound 7

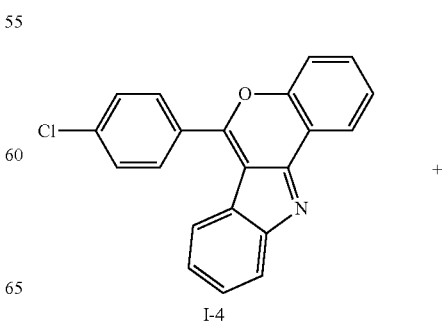

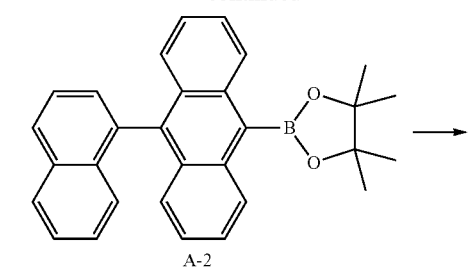

A-2

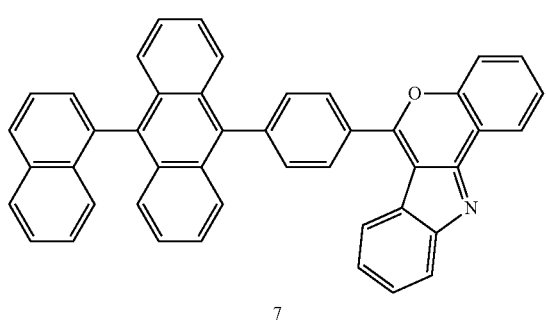

7

4.12 g (yield of 69%) of Compound 7 was obtained in the same (or substantially the same) manner as in synthesis of Compound 1, except that Intermediate A-2 was used instead of 1-naphthaleneboronic acid. The obtained compound was confirmed by MS/FAB and $^1$H NMR. $C_{45}H_{27}NO$ cal. 597.21. found 597.22.

Synthesis Example 4: Synthesis of Compound 12

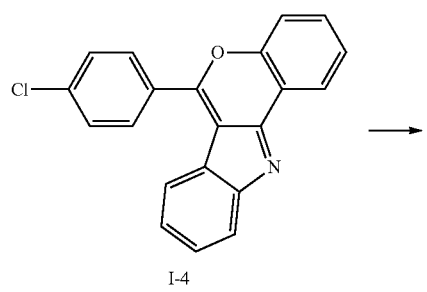

I-4

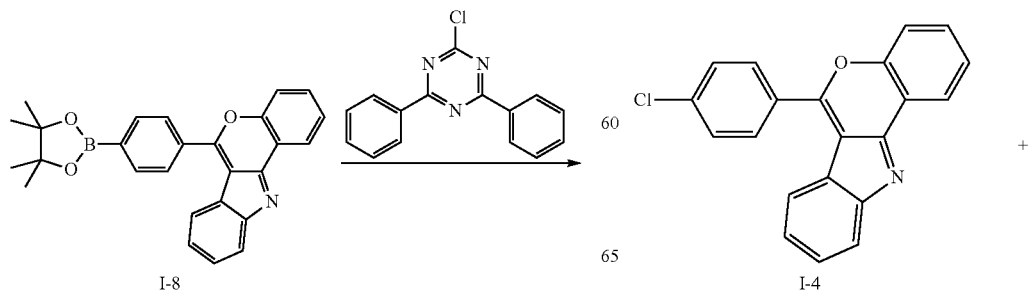

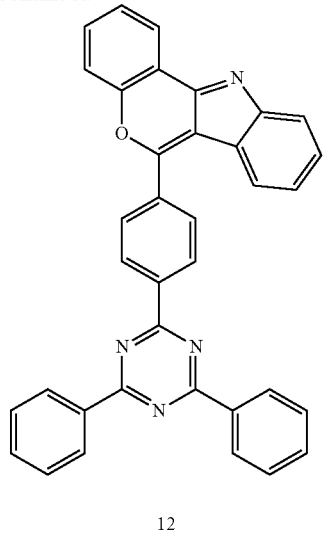

12

Synthesis of Intermediate I-8

3.29 g (10.0 mmol) of Intermediate I-4, 2.56 g (10.0 mmol) of bis(pinacolato)dibrane, 0.35 g (0.50 mmol) of [1,1'-bis(diphenylphosphino)pherocene]dichloropalladium (II) (hereinafter referred to as PdCl$_2$(dppf)$_2$), and 2.94 g (30.0 mmol) of KOAc were dissolved in 40 ml of DMSO, and then, the resulting mixture was stirred at a temperature of 80° C. for 6 hours. The obtained reaction solution was cooled at room temperature, and then, subjected to an extraction process three times using 40 mL of water and 40 mL of diethylether. The collected organic layer was dried by using magnesium sulfate, and then, the residual obtained by drying using sulfate was separation-purified by separation-purified by silicagel column chromatography to obtain 2.44 g (yield of 58%) of Intermediate I-8. The obtained compound was confirmed by LC-MS. $C_{27}H_{24}BNO_3$: M+1 422.2

Synthesis of Compound 12

3.47 g (yield of 66%) of Compound 12 was obtained in the same (or substantially the same) manner as in synthesis of Compound 1, except that Intermediate I-8 was used instead of Intermediate I-4, and 2-chloro-4,6-diphenyl-1,3,5-triazine was used instead of 1-naphthaleneboronic acid. The obtained compound was confirmed by MS/FAB and $^1$H NMR. $C_{36}H_{22}N_4O$ cal. 526.18. found 526.20.

Synthesis Example 5: Synthesis of Compound 20

-continued

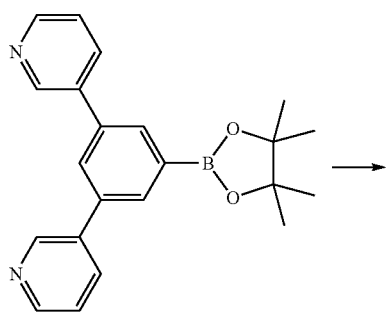

A-3

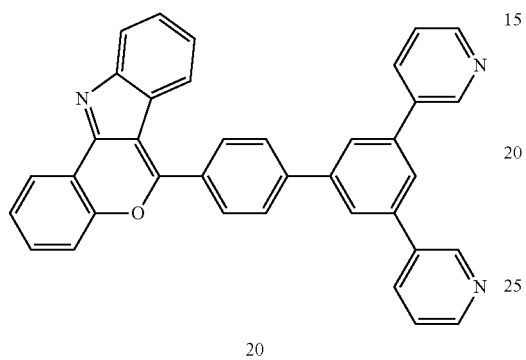

20

3.78 g (yield of 72%) of Compound 20 was obtained in the same (or substantially the same) manner as in synthesis of Compound 1, except that Intermediate A-3 was used instead of 1-naphthaleneboronic acid. The obtained compound was confirmed by MS/FAB and $^1$H NMR. $C_{37}H_{23}N_3O$ cal. 525.19. found 525.18.

Synthesis Example 6: Synthesis of Compound 54

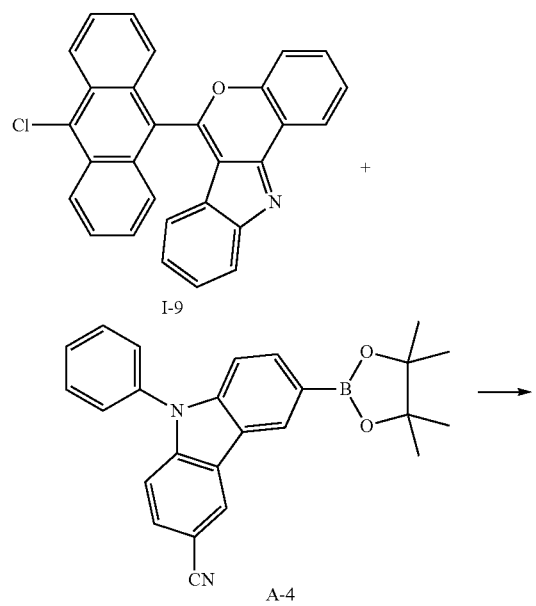

-continued

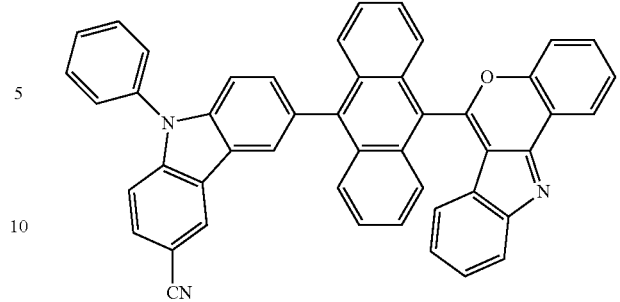

54

4.30 g (yield of 65%) of Compound 54 was obtained in the same (or substantially the same) manner as in synthesis of Compound 1, except that Intermediate I-9 was used instead of Intermediate I-4 and Intermediate A-4 was used instead of 1-naphthaleneboronic acid. The obtained compound was confirmed by MS/FAB and $^1$H NMR. $C_{48}H_{27}N_3O$ cal. 661.22. found 661.23.

Synthesis Example 7: Synthesis of Compound 66

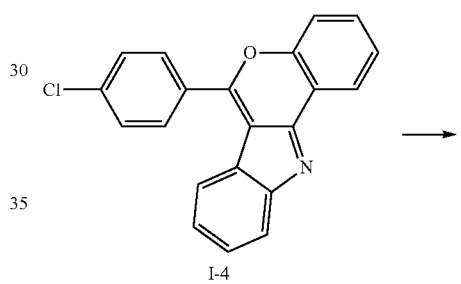

I-4

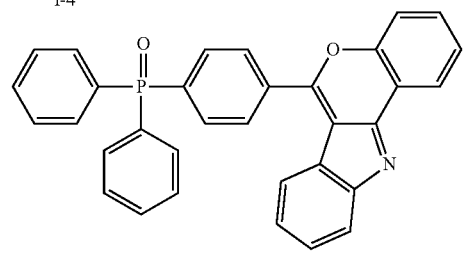

66

3.29 g (10 mmol) of Intermediate I-4 was dissolved in 40 mL of THF, and then at a temperature of −78° C., 4 mL (2.5M in Hexane) of normal butyllithium was added thereto. One hour after, 2.20 g (10 mmol) of chlorodiphenylphosphine was slowly added dropwise thereto, and the result was stirred for 3 hours, and then, the temperature was raised to room temperature. Water was added thereto, and the resultant solution was washed three times using 30 mL of ethylacetate (30 mL). The washed ethylacetate layer was dried using $MgSO_4$. After a solvent was removed therefrom, the residual was dissolved in 25 mL of dichloromethane, and 2 mL of hydrogen peroxide was added thereto, followed by stirring at room temperature for 20 hours. Next, 20 mL of water was added thereto, and an extraction process was performed thereon three times by using 20 mL of dichloromethane. The collected organic layer was dried using magnesium sulfate, and the residual obtained by removing a solvent therefrom by evaporation was separation-purified by silicagel column chromatography to obtain 3.12 g (yield of 63%) of Compound 66. The obtained compound was confirmed by MS/FAB and $^1$H NMR. $C_{33}H_{22}NO_2P$ cal. 495.14. found 495.15.

$^1$H NMR and MS/FAB results of the synthesized compounds are shown in Table 1.

Synthesis methods of compounds other than those shown in Table 1 should be apparent to those of ordinary skill in the art of organic light-emitting devices by referring to the above-described synthesis pathways and source materials.

TABLE 1

| Compound | $^1$H NMR (CDCl$_3$, 400 MHz) | MS/FAB found | MS/FAB calc. |
|---|---|---|---|
| 1 | 8.11-8.08 (m, 1H), 7.80-8.78 (m, 1H), 7.76-7.74 (m, 1H), 7.72-7.70 (m, 1H), 7.63-7.57 (m, 5H), 7.51 (d,1H), 7.47-7.34 (m, 7H), 7.27-7.23 (m, 1H), 7.14-7.11 (m, 1H) | 421.14 | 421.15 |
| 5 | 8.28-8.26 (m, 1H), 8.21-8.18 (m, 1H), 8.14-8.12 (m, 2H), 8.01-7.98 (m, 1H), 7.90-7.89 (m, 2H),7.84-7.81 (dd, 2H), 7.80-7.73 (m, 3H), 7.62-7.60 (dd, 1H), 7.56-7.52 (m, 1H), 7.48-7.35 (m, 9H), 7.31-7.27 (m, 2H), 7.20-7.15 (m, 1H) | 622.19 | 622.20 |
| 7 | 8.22-8.27 (m, 1H), 7.84-7.81 (m, 3H), 7.80-7.78 (m, 1H), 7.75-7.71 (m, 4H), 7.67-7.60 (m, 4H), 7.48-7.7.43 (m, 3H), 7.39-7.27 (m, 10H), 7.10-7.05 (m, 1H) | 597.22 | 597.21 |
| 12 | 8.71-8.68 (m, 4H), 8.59-8.55 (m, 2H), 8.40-8.37 (m, 2H), 8.20-8.17 (m, 1H), 7.80-7.78 (m, 1H), 7.62-7.60 (m, 1H), 7.54-7.51 (m, 4H), 7.45-7.32 (m, 7H) | 526.20 | 526.18 |
| 20 | 8.83-8.82 (m, 2H), 8.51-8.49 (m, 2H), 8.22-8.19 (m, 1H), 8.10-8.07 (m, 2H), 8.01-7.99 (m, 2H), 7.96 (d, 1H), 7.93-7.90 (m, 2H), 7.83-7.78 (m, 2H), 7.62-7.60 (m, 1H), 7.48-7.33 (m, 8H) | 525.18 | 525.19 |

TABLE 1-continued

| Compound | $^1$H NMR (CDCl$_3$, 400 MHz) | MS/FAB found | MS/FAB calc. |
|---|---|---|---|
| 54 | 8.55-8.53 (m, 1H), 8.45-8.43 (m, 2H), 8.28-8.26 (m, 2H), 7.88-7.86 (m, 1H), 7.80-7.78 (m, 1H),7.71-7.62 (m, 5H), 7.53-7.41 (m, 11H), 7.33-7.24 (m, 2H), 7.19-7.15 (m, 2H) | 661.23 | 661.22 |
| 66 | 8.22-8.19 (m, 1H), 7.92-7.88 (m, 2H), 7.80-7.74 (m, 3H), 7.71-7.65 (m, 4H), 7.62-7.58 (m, 1H), 7.52-7.32 (m, 11H) | 495.15 | 495.14 |

Example 1

An ITO glass substrate (a product of Corning Inc.) including an ITO layer, which acts as an ITO anode, having a thickness of 15 Ω/cm$^2$ (1200 Å) was cut to a size of 50 mm×50 mm×0.7 mm, and sonicated using isopropyl alcohol and pure water, each for 5 minutes, and then, washed by exposure to ozone for 30 minutes. The resultant ITO glass substrate was mounted on a vacuum deposition apparatus.

2-TNATA was deposited on the ITO anode to form a hole injection layer having a thickness of 600 Å, and then, NPB was deposited on the hole injection layer to form a hole transport layer having a thickness of 300 Å. Next, ADN (as a host) and DPAVBi (as a dopant) were codeposited on the hole transport layer at a weight ratio of 98:2 to form an emission layer having a thickness of 300 Å.

Compound 1 was deposited on the emission layer to form an electron transport layer having a thickness of 300 Å, and LiF was deposited on the electron transport layer to form an electron injection layer having a thickness of 10 Å, and Al was deposited on the electron injection layer to form a cathode having a thickness of 3000 Å, thereby completing the manufacture of an organic light-emitting device.

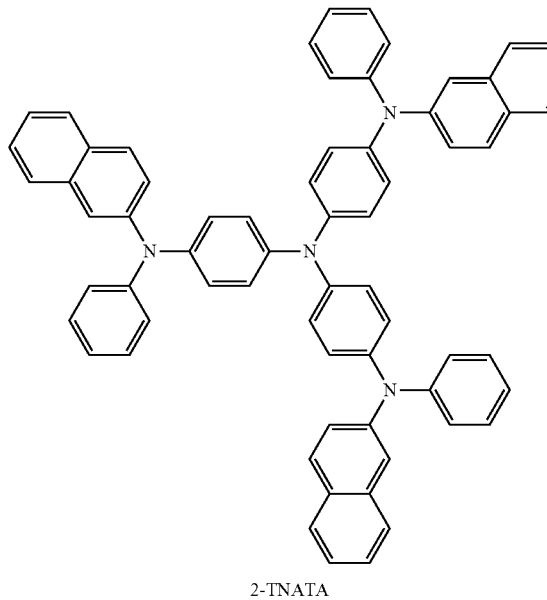

2-TNATA

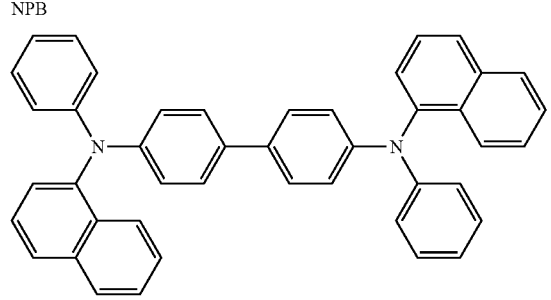

NPB

ADN

DPAVBi

Examples 2 to 7 and Comparative Examples 1 to 3

Organic light-emitting devices were each manufactured in the same (or substantially the same) manner as in Example 1, except that in forming an electron transport layer, compounds as shown in Table 2 were used instead of Compound 1.

Evaluation Example 1

The driving voltage, current density, luminance, efficiency, and half lifespan of the organic light-emitting devices manufactured according to Examples 1 to 7 and Comparative Examples 1 to 3 were measured by using Keithley SMU 236 and luminance meter PR650 (Photo Research, Inc.). Evaluation results are shown in Table 2. Half lifespan indicates a period of time that lapses until the brightness of the organic light-emitting device reduces to 50% of initial brightness.

TABLE 2

|  | Electron transport layer | Driving voltage (V) | Current density (mA/cm$^2$) | Luminance (cd/m$^2$) | Efficiency (cd/A) | Emission color | Half lifespan (hr @100 mA/cm$^2$) |
|---|---|---|---|---|---|---|---|
| Example 1 | Compound 1 | 5.27 | 50 | 3,115 | 6.23 | blue | 235 |
| Example 2 | Compound 5 | 5.33 | 50 | 3,315 | 6.63 | blue | 287 |
| Example 3 | Compound 7 | 5.39 | 50 | 3,275 | 6.55 | blue | 245 |
| Example 4 | Compound 12 | 5.21 | 50 | 3,475 | 6.95 | blue | 252 |
| Example 5 | Compound 20 | 5.54 | 50 | 3,185 | 6.37 | blue | 276 |
| Example 6 | Compound 54 | 5.52 | 50 | 3,240 | 6.48 | blue | 305 |
| Example 7 | Compound 66 | 5.41 | 50 | 3,255 | 6.51 | blue | 335 |
| Comparative Example 1 | Alq$_3$ | 7.35 | 50 | 2,065 | 4.13 | blue | 145 |
| Comparative Example 2 | Compound A | 5.63 | 50 | 2,505 | 5.01 | blue | 130 |

TABLE 2-continued

|  | Electron transport layer | Driving voltage (V) | Current density (mA/cm$^2$) | Luminance (cd/m$^2$) | Efficiency (cd/A) | Emission color | Half lifespan (hr @100 mA/cm$^2$) |
|---|---|---|---|---|---|---|---|
| Comparative Example 3 | Compound C | 6.02 | 50 | 2,910 | 5.82 | blue | 220 |

Alq$_3$

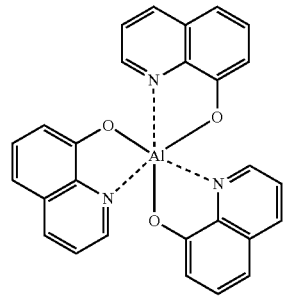

Alq$_3$

Compound A

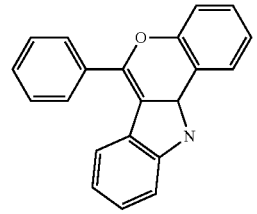 [SMILES: c1ccc(C2=C3c4ccccc4NC3c3ccccc3O2)cc1]

Compound C

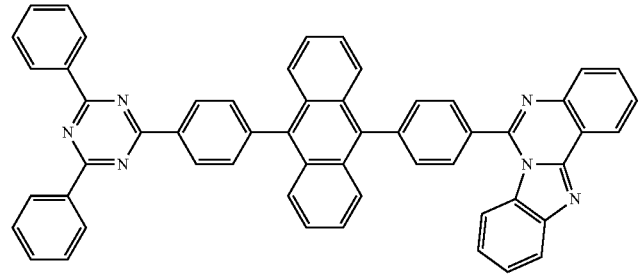 [SMILES: c1ccc(-c2nc(-c3ccccc3)nc(-c3ccc(-c4c5ccccc5c(-c5ccc(-c6nc7ccccc7c7nc8ccccc8n67)cc5)c5ccccc45)cc3)n2)cc1]

As shown by the results in Table 1, the organic light-emitting devices manufactured according to Examples 1 to 7 had lower driving voltage, maintained current density, exhibited higher luminance, higher efficiency, and a longer half lifespan than the organic light-emitting devices of Comparative Examples 1 to 3.

Accordingly, an organic light-emitting device including one or more of the condensed cyclic compounds according to embodiments of the present disclosure may have low driving voltage, high efficiency, high luminance, and long lifespan.

It will be understood that the terms, such as "comprises," "comprising," "includes", and/or "including", when used in this specification, specify the presence of stated features, integers, steps, operations, elements, and/or components, but do not preclude the presence or addition of one or more other features, integers, steps, operations, elements, components, and/or groups thereof.

Expressions such as "at least one selected from" and "one selected from," when preceding a list of elements, modify the entire list of elements and do not modify the individual elements of the list. Further, the use of "may" when describing embodiments of the present disclosure refers to "one or more embodiments of the present disclosure."

In addition, as used herein, the terms "use," "using," and "used" may be considered synonymous with the terms "utilize," "utilizing," and "utilized," respectively.

As used herein, the term "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. § 112(a), and 35 U.S.C. § 132(a).

It should be understood that the example embodiments described therein should be considered in a descriptive sense only and not for purposes of limitation. Descriptions of features or aspects within each embodiment should typically be considered as available for other similar features or aspects in other embodiments included within the spirit and scope of the appended claims and equivalents thereof.

What is claimed is:

1. A condensed cyclic compound represented by one selected from Formulae 1-1 and 1-2:

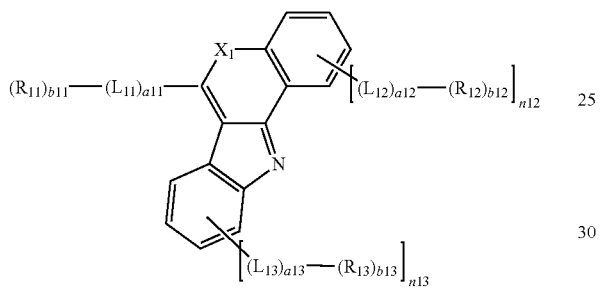

Formula 1-1

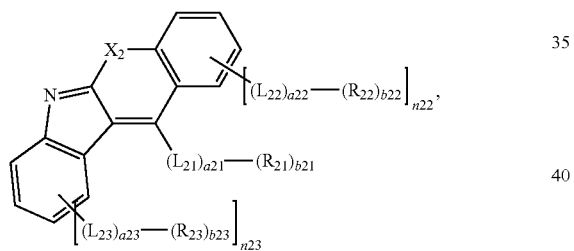

Formula 1-2 wherein in Formulae 1-1 and 1-2, $X_1$ and $X_2$ are each independently O or S;

$L_{11}$ to $L_{13}$ and $L_{21}$ to $L_{23}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a11 to a13 and a21 to a23 are each independently selected from 0, 1, 2, and 3, and when a11 is 2 or more, 2 or more $L_{11}(s)$ are identical to or different from each other, and when a12 is 2 or more, 2 or more $L_{12}(s)$ are identical to or different from each other, and when a13 is 2 or more, 2 or more $L_{13}(s)$ are identical to or different from each other, and when a21 is 2 or more, 2 or more $L_{21}(s)$ are identical to or different from each other, and when a22 is 2 or more, 2 or more $L_{22}(s)$ are identical to or different from each other, and when a23 is 2 or more, 2 or more $L_{23}(s)$ are identical to or different from each other;

$R_{11}$ to $R_{13}$ and $R_{21}$ to $R_{23}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —P(=O)($Q_4$)($Q_5$), —S(=O)($Q_6$), and —S(=O)$_2$($Q_7$);

b11 to b13 and b21 to b23 are each independently selected from 0, 1, 2, and 3, and when b11 is 2 or more, 2 or more $R_{11}(s)$ are identical to or different from each other, and when b12 is 2 or more, 2 or more $R_{12}(s)$ are identical to or different from each other, and when b13 is 2 or more, 2 or more $R_{13}(s)$ are identical to or different from each other, and when b21 is 2 or more, 2 or more $R_{21}(s)$ are identical to or different from each other, and when b22 is 2 or more, 2 or more $R_{22}(s)$ are identical to or different from each other, and when b23 is 2 or more, 2 or more $R_{23}(s)$ are identical to or different from each other; and n12, n13, n22, and n23 are each independently selected from 0, 1, 2, 3, and 4, wherein in Formula 1-1, —($R_{11}$)$_{b11}$-($L_{11}$)$_{a11}$- is neither hydrogen, nor a substituted or an unsubstituted $C_1$-$C_6$ alkyl group, nor an unsubstituted phenyl group and the compound represented by Formula 1-1 is neither Compound A nor Compound B, and wherein in Formula 1-2, -($L_{21}$)$_{a21}$-($R_{21}$)$_{b21}$— is not hydrogen, an unsubstituted phenyl group, —Cl, an amino group, a substituted or unsubstituted $C_1$-$C_2$ alkyl group, or a substituted or unsubstituted $C_1$-$C_{10}$ heterocycloalkyl group and the compound represented by Formula 1-2 is not Compound D:

Compound A

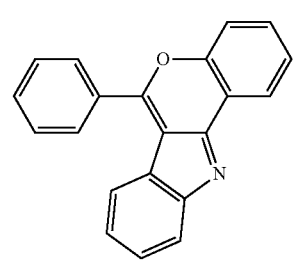

-continued

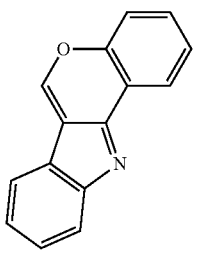
Compound B

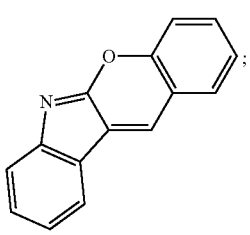
Compound D and
wherein at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group and substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, —Si($Q_{11}$)($Q_{12}$)($Q_{13}$), —B($Q_{14}$)($Q_{15}$), and —N($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —B($Q_{24}$)($Q_{25}$), and —N($Q_{26}$)($Q_{27}$); and —Si($Q_{31}$)($Q_{32}$)($Q_{33}$), —B($Q_{34}$)($Q_{35}$), and —N($Q_{36}$)($Q_{37}$), wherein $Q_1$ to $Q_7$, $Q_{11}$ to $Q_{17}$, $Q_{21}$ to $Q_{27}$ and $Q_{31}$ to $Q_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

2. The condensed cyclic compound of claim 1, wherein when at least one of a11, a12, a13, a21, a22 and a23 is not 0, $L_{11}$ to $L_{13}$ and $L_{21}$ to $L_{23}$ are each independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group;

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

3. The condensed cyclic compound of claim 1, wherein when at least one of a11, a12, a13, a21, a22 and a23 is not 0, $L_{11}$ to $L_{13}$ and $L_{21}$ to $L_{23}$ are each independently represented by any one selected from Formulae 3-1 to 3-25:

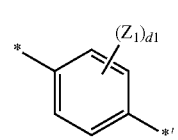

Formula 3-1

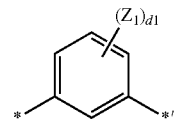

Formula 3-2

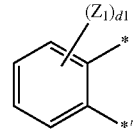

Formula 3-3

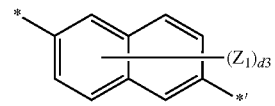

Formula 3-4

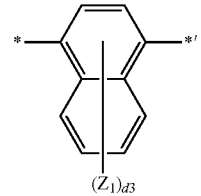

Formula 3-5

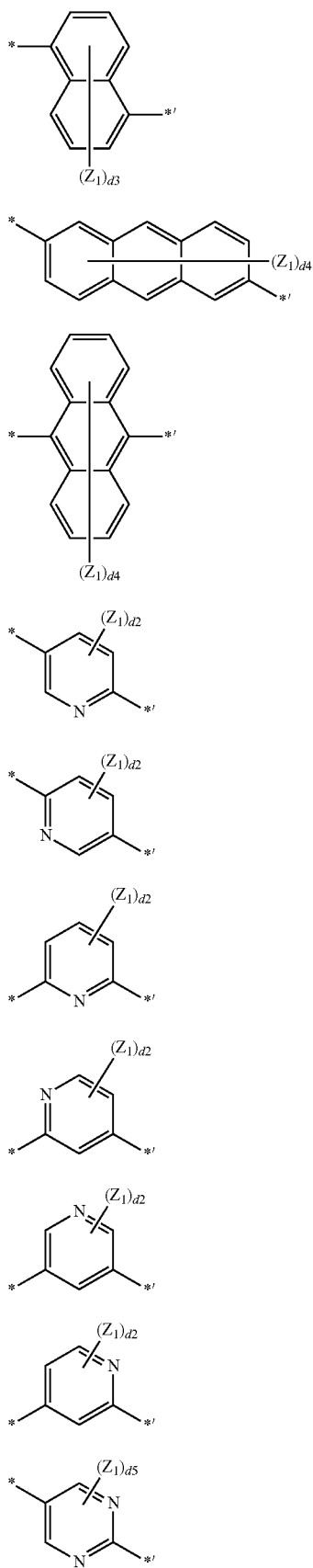
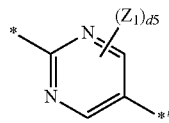
Formula 3-16
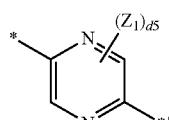
Formula 3-17
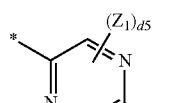
Formula 3-18
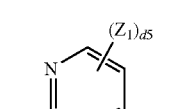
Formula 3-19
Formula 3-20
Formula 3-21
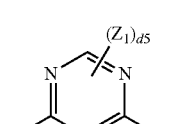
Formula 3-22
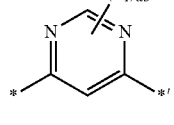
Formula 3-23
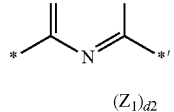
Formula 3-24
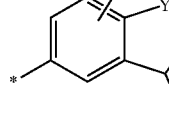
Formula 3-25
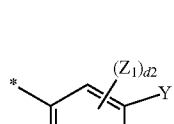
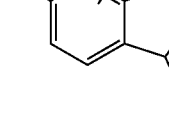
wherein in Formulae 3-1 to 3-25,
Y₁ is selected from O, S, C(Z₃)(Z₄), and N(Z₅);
Z₁ to Z₅ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, d1 is an integer selected from 1 to 4, d2 an integer selected from 1 to 3, d3 is an integer selected from 1 to 6, d4 is an integer selected from 1 to 8, d5 is 1 or 2, and each of * and *' is a binding site to a neighboring atom.

4. The condensed cyclic compound of claim 1, wherein when at least one of a11, a12, a13, a21, a22 and a23 is not 0, $L_{11}$ to $L_{13}$ and $L_{21}$ to $L_{23}$ are each independently represented by any one selected from Formulae 4-1 to 4-8:

Formula 4-1

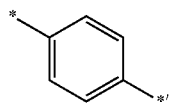

Formula 4-2

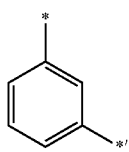

Formula 4-3

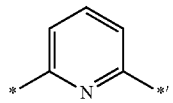

Formula 4-4

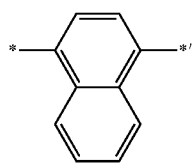

Formula 4-5

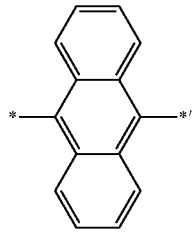

Formula 4-6

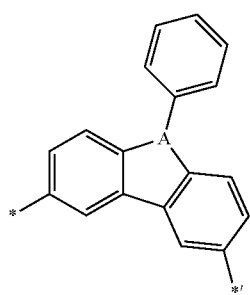

Formula 4-7

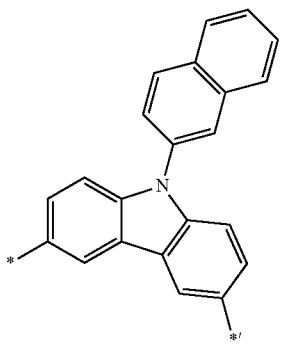

Formula 4-8

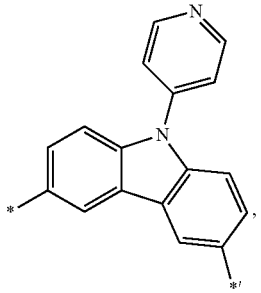

wherein each of * and *' in Formulae 4-1 and 4-8 is a binding site to a neighboring atom.

5. The condensed cyclic compound of claim 1, wherein a11 and a21 are each independently selected from 0, 1, and 2, and a12, a13, a22, and a23 are each independently 0 or 1.

6. The condensed cyclic compound of claim 1, wherein when at least one of b11, b12, b13, b21, b22 and b23 is not 0, $R_{11}$ to $R_{13}$ and $R_{21}$ to $R_{23}$ are each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthrolinyl group, a phenanthridinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dinaphthofuranyl group, a dinaphthothiophenyl group, a benzocarbazolyl group, a dibenzocarbazolyl group, an imidazopyridinyl group and an imidazopyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthrolinyl group, a phenanthridinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dinaphthofuranyl group, a dinaphthothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthrolinyl group, a phenanthridinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dinaphthofuranyl group, a dinaphthothiophenyl group, a benzocarbazolyl group, a dibenzocarbazolyl group, an imidazopyridinyl group, an imidazopyrimidinyl group, and —Si($Q_{31}$)($Q_{32}$)($Q_{33}$); and —Si($Q_1$)($Q_2$)($Q_3$), —P(=O)($Q_4$)($Q_5$), —S(=O)($Q_6$), and —S(=O)$_2$($Q_7$), wherein $Q_1$ to $Q_7$ and $Q_{31}$ to $Q_{33}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a carbazolyl group.

7. The condensed cyclic compound of claim 1, wherein when at least one of b11 and b21 is not 0, $R_{11}$ and $R_{21}$ are each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a phenanthrolinyl group, a phenanthridinyl group, a benzofuranyl group, a benzothiophenyl group, a dibenzofuranyl group, a dibenzothiophenyl group, a dinaphthofuranyl group, a dinaphthothiophenyl group, a triazinyl group, a benzocarbazolyl group, and a dibenzocarbazolyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a phenanthrolinyl group, a phenanthridinyl group, a benzofuranyl group, a benzothiophenyl group, a dibenzofuranyl group, a dibenzothiophenyl group, a dinaphthofuranyl group, a dinaphthothiophenyl group, a triazinyl group, a benzocarbazolyl group, and a dibenzocarbazolyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a benzofuranyl group, a benzothiophenyl group, a triazinyl group, a benzocarbazolyl group, a dibenzocarbazolyl group, and —Si(Q$_{31}$)(Q$_{32}$)(Q$_{33}$); and Si(Q$_1$)(Q$_2$)(Q$_3$), —P(=O)(Q$_4$)(Q$_5$), —S(=O)(Q$_6$), and —S(=O)$_2$(Q$_7$), wherein Q$_1$ to Q$_7$ and Q$_{31}$ to Q$_{33}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group.

8. The condensed cyclic compound of claim 1, wherein when at least one of b11 and b21 is not 0, R$_{11}$ and R$_{21}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, and groups represented by any one selected from Formulae 5-1 to 5-44:

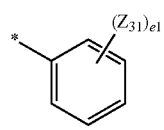

Formula 5-1

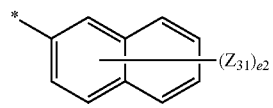

Formula 5-2

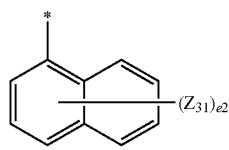

Formula 5-3

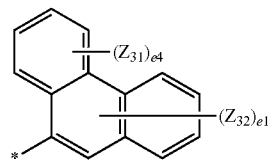

Formula 5-4

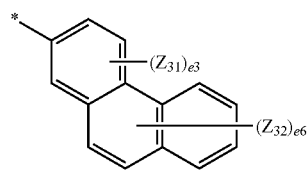

Formula 5-5

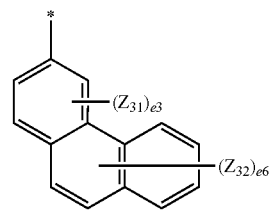

Formula 5-6

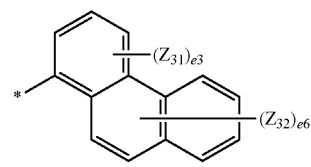

Formula 5-7

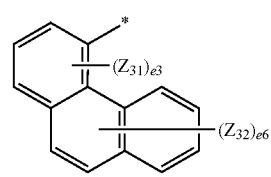

Formula 5-8

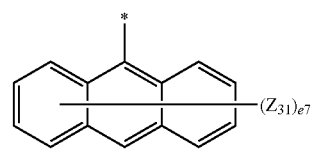

Formula 5-9

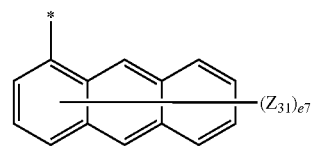

Formula 5-10

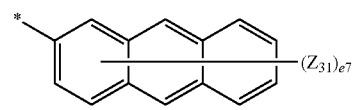

Formula 5-11

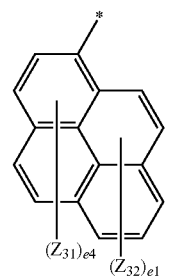

Formula 5-12

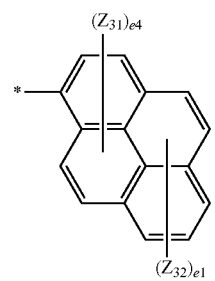

Formula 5-13

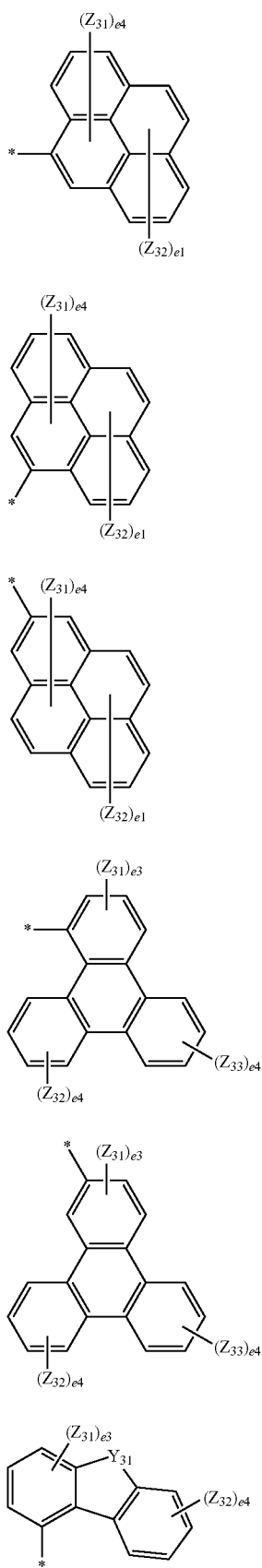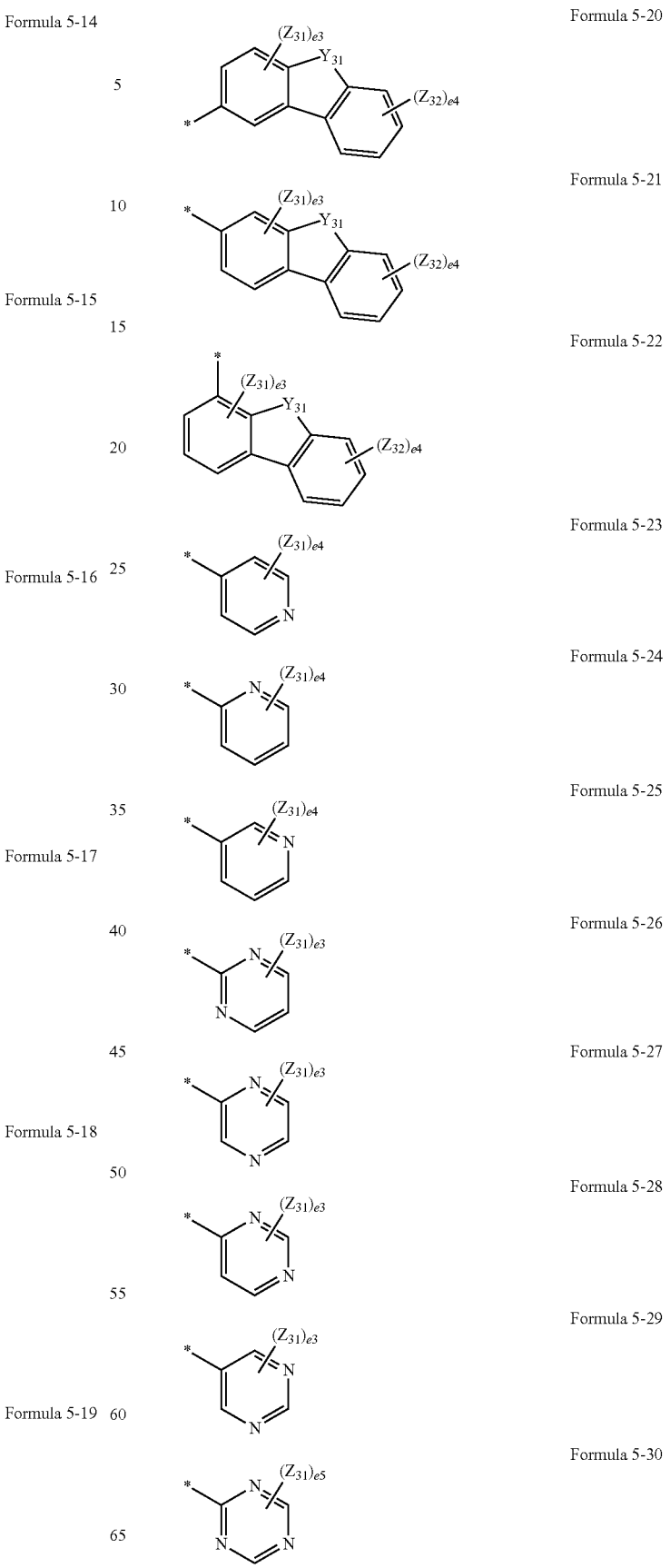

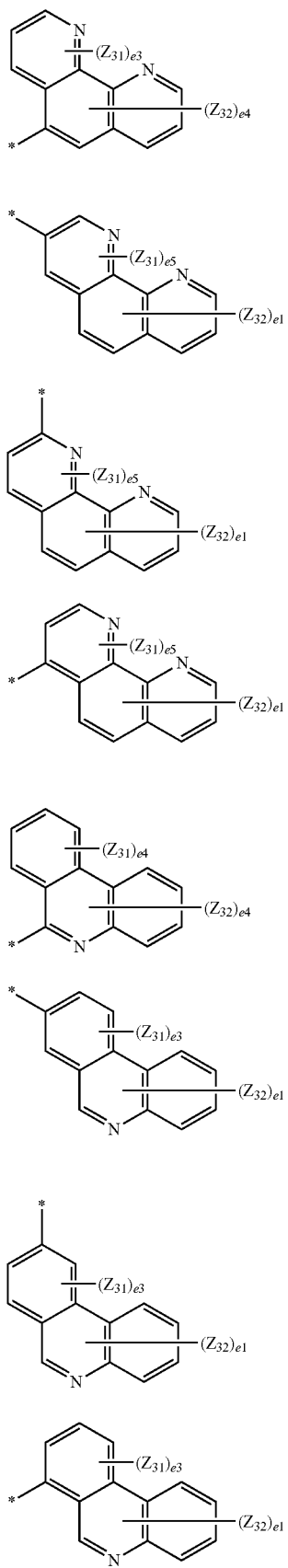

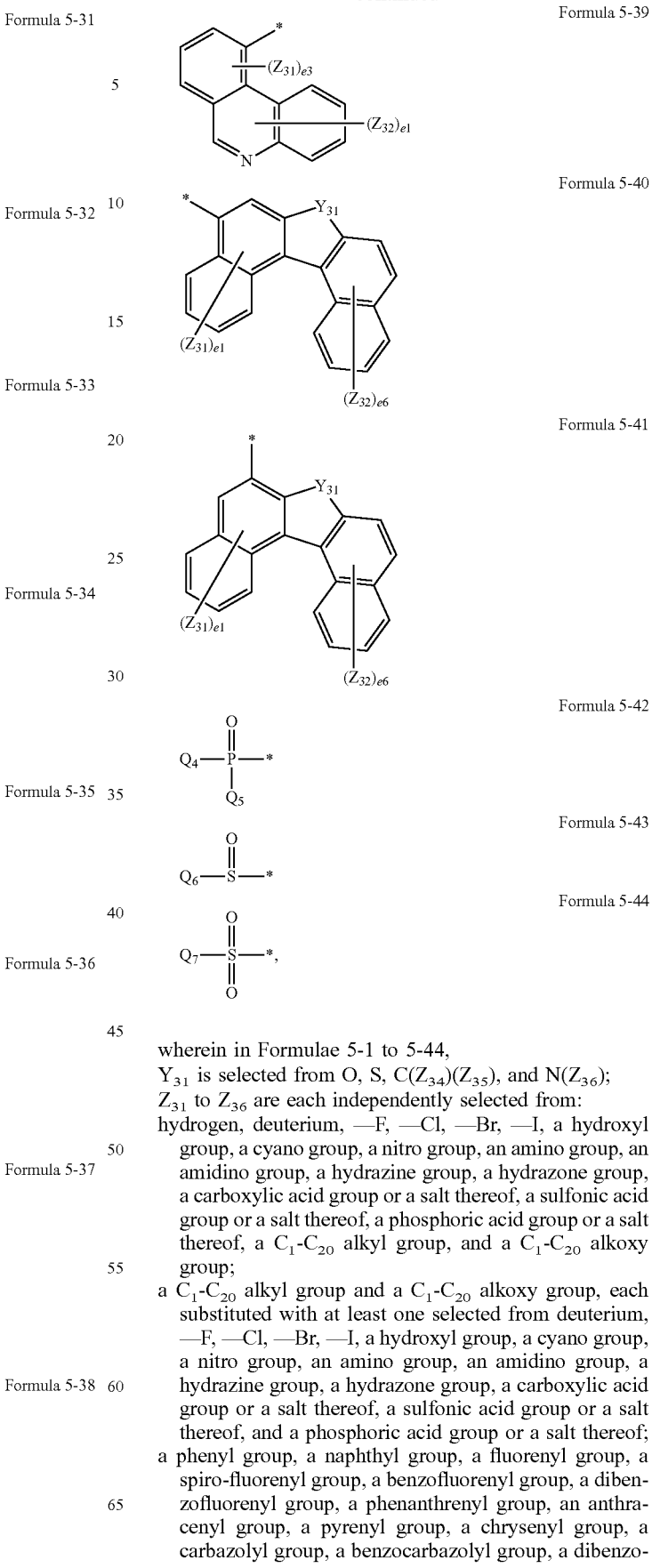

wherein in Formulae 5-1 to 5-44,
$Y_{31}$ is selected from O, S, $C(Z_{34})(Z_{35})$, and $N(Z_{36})$;
$Z_{31}$ to $Z_{36}$ are each independently selected from:
hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, a dibenzocarbazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, a dibenzocarbazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group; and —Si($Q_{31}$)($Q_{32}$)($Q_{33}$), wherein $Q_4$ to $Q_7$ and $Q_{31}$ to $Q_{33}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a carbazolyl group;

e1 is an integer selected from 1 to 5, e2 is an integer selected from 1 to 7, e3 is an integer selected from 1 to 3, e4 is an integer selected from 1 to 4, e5 is an integer selected from 1 and 2, e6 is an integer selected from 1 to 6, e7 is an integer selected from 1 to 9, and * is a binding site to a neighboring atom.

9. The condensed cyclic compound of claim 8, wherein when $R_{11}$ and $R_{21}$ are each independently represented by any one selected from Formulae 5-1 to 5-44, $Z_{31}$ to $Z_{36}$ in Formulae 5-1 to 5-44 are each independently selected from hydrogen, deuterium, —F, —Cl, —Br, —I, a hydroxyl group, a cyano group, a nitro group, an amino group, an amidino group, a hydrazine group, a hydrazone group, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, a dibenzocarbazolyl group, a pyridinyl group, a pyrazinyl group, a pyrimidinyl group, and a pyridazinyl group.

10. The condensed cyclic compound of claim 1, wherein when at least one of b11 and b21 is not 0, $R_{11}$ and $R_{21}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, and a group represented by any one selected from Formulae 6-1 to 6-42:

Formula 6-1

Formula 6-2

Formula 6-3

Formula 6-4

Formula 6-5

Formula 6-6

-continued
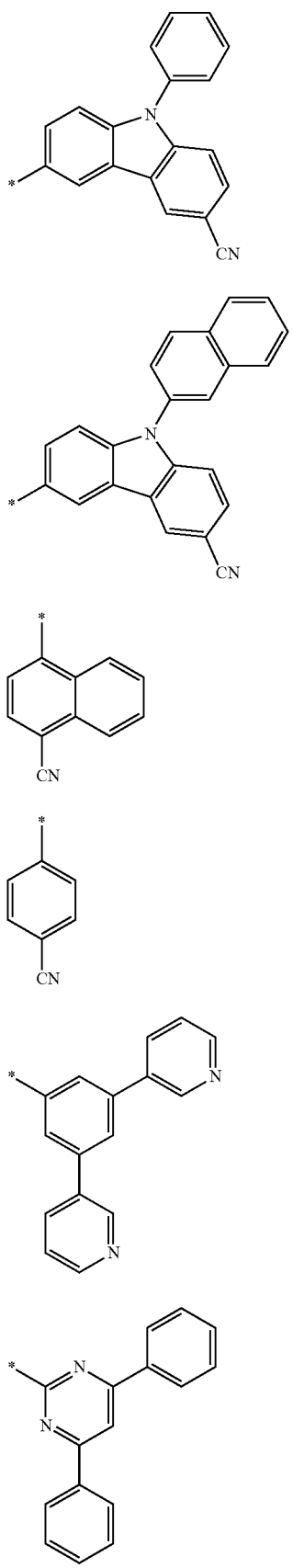
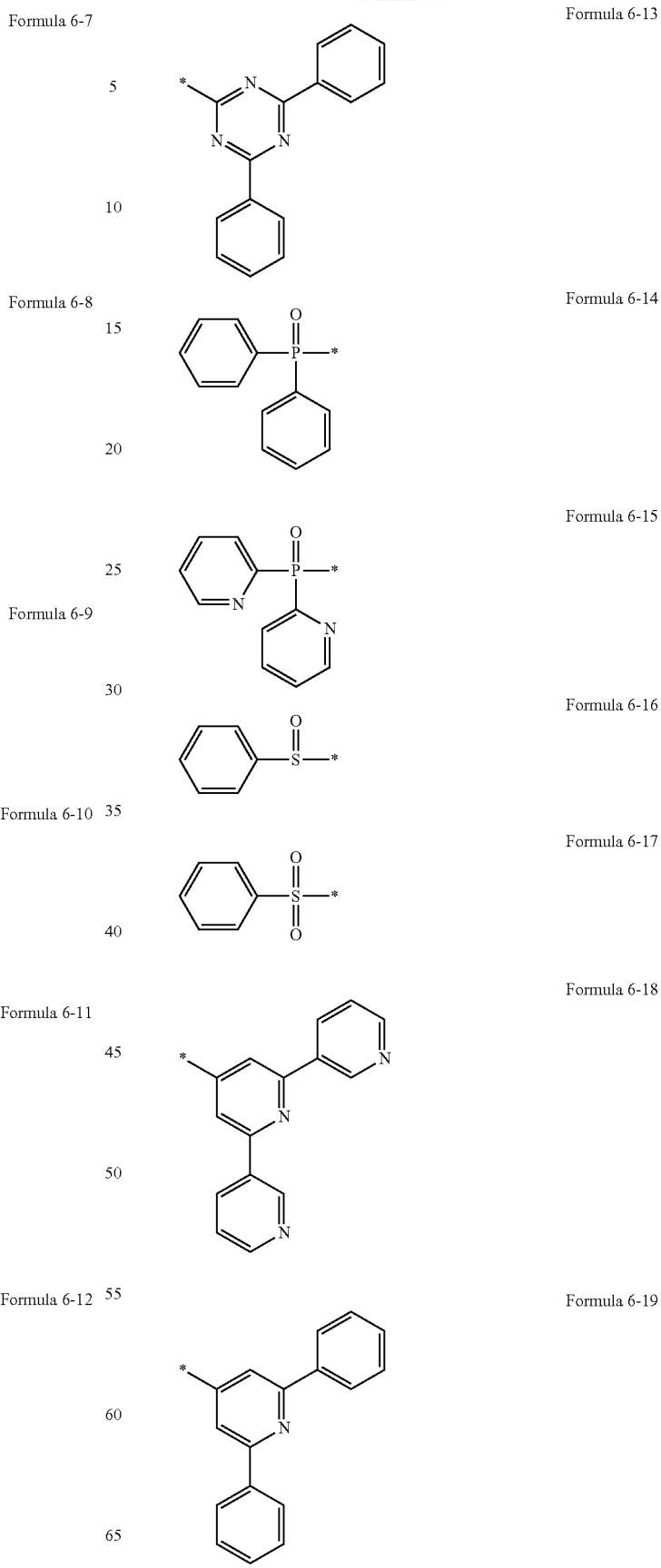
Formula 6-7
Formula 6-8
Formula 6-9
Formula 6-10
Formula 6-11
Formula 6-12
Formula 6-13
Formula 6-14
Formula 6-15
Formula 6-16
Formula 6-17
Formula 6-18
Formula 6-19

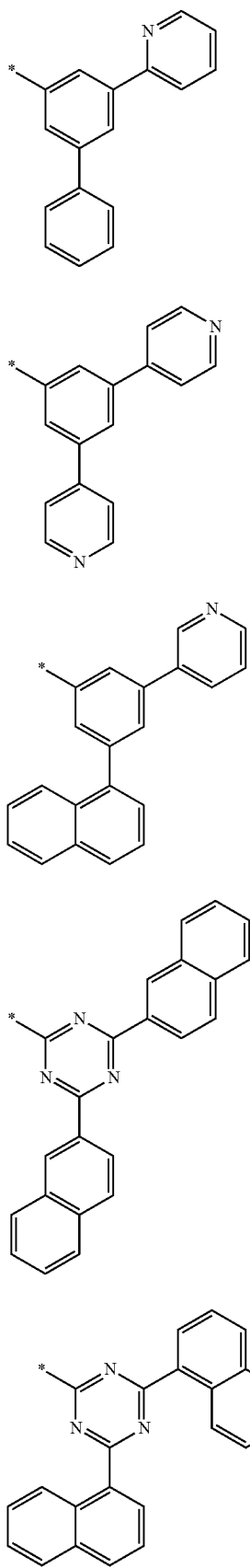
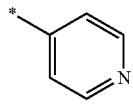
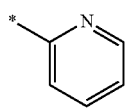
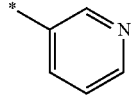
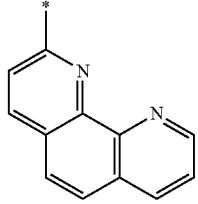
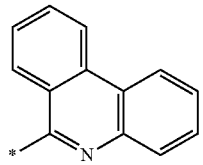
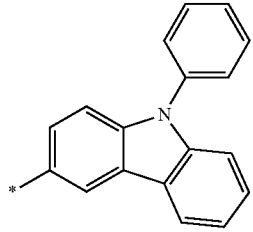
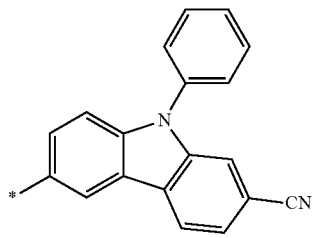
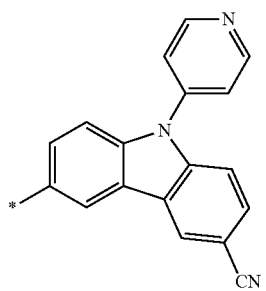
Formula 6-20
Formula 6-21
Formula 6-22
Formula 6-23
Formula 6-24
Formula 6-25
Formula 6-26
Formula 6-27
Formula 6-28
Formula 6-29
Formula 6-30
Formula 6-31
Formula 6-32

-continued

Formula 6-33
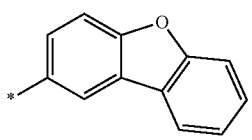

Formula 6-34
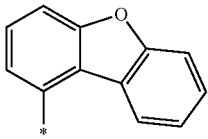

Formula 6-35
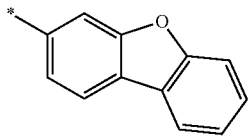

Formula 6-36
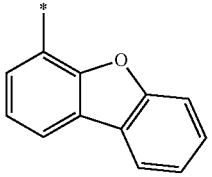

Formula 6-37
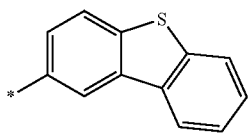

Formula 6-38
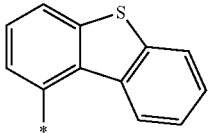

Formula 6-39
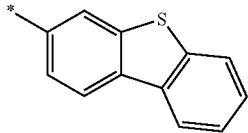

Formula 6-40
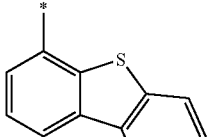

Formula 6-41
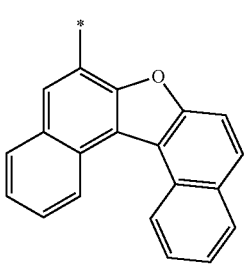

-continued

Formula 6-42
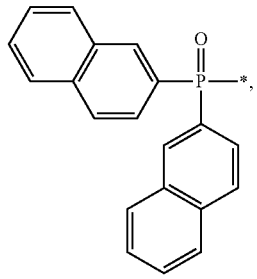

wherein * in Formulae 6-1 to 6-42 is a binding site to a neighboring atom.

11. The condensed cyclic compound of claim 1, wherein when at least one of b12, b13, b22 and b23 is not 0, $R_{12}$, $R_{13}$, $R_{22}$ and $R_{23}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, and groups represented by any one selected from Formulae 7-1 to 7-44:

Formula 7-1
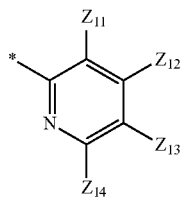

Formula 7-2

Formula 7-3
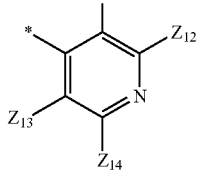

Formula 7-4
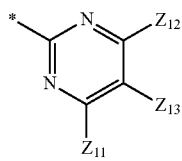

Formula 7-5
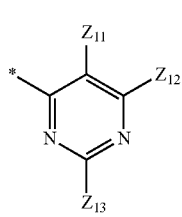

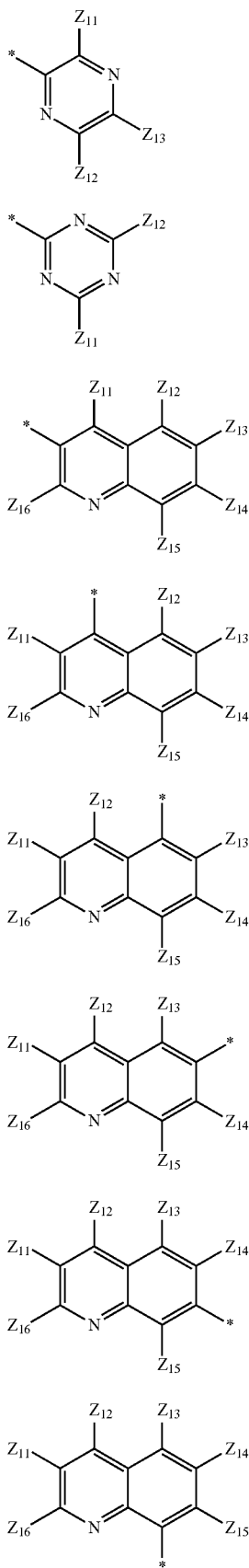
Formula 7-6
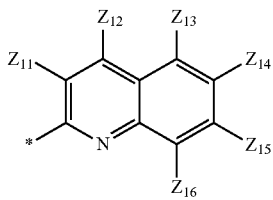
Formula 7-14
Formula 7-7
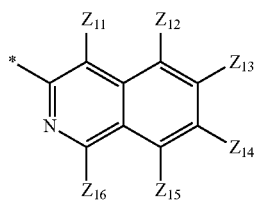
Formula 7-15
Formula 7-8
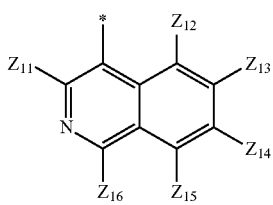
Formula 7-16
Formula 7-9
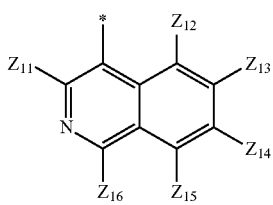
Formula 7-10
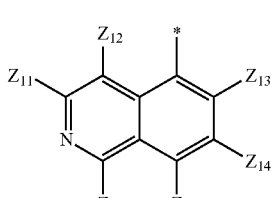
Formula 7-17
Formula 7-11
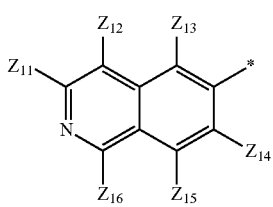
Formula 7-18
Formula 7-12
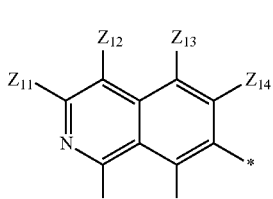
Formula 7-19
Formula 7-13
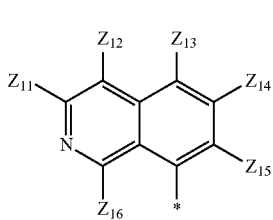
Formula 7-20

-continued
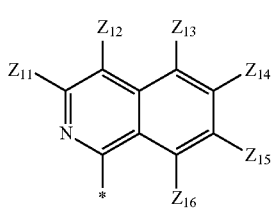
Formula 7-21
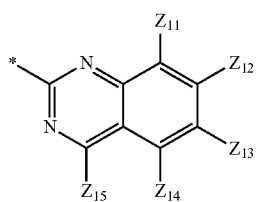
Formula 7-22
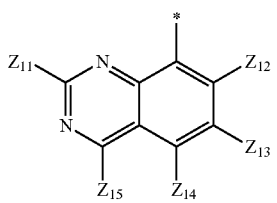
Formula 7-23
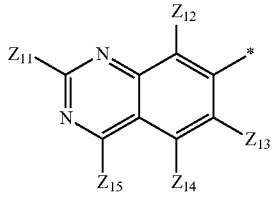
Formula 7-24
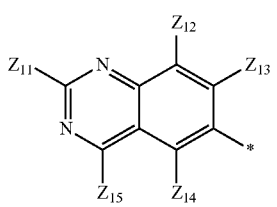
Formula 7-25
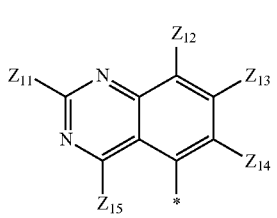
Formula 7-26
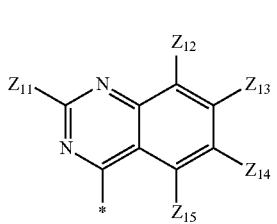
Formula 7-27
-continued
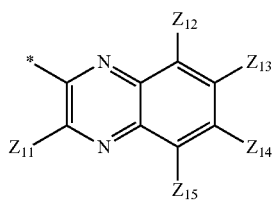
Formula 7-28
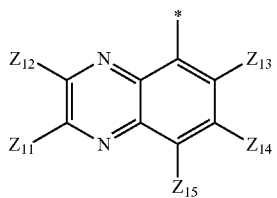
Formula 7-29
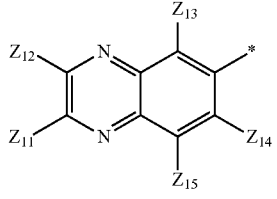
Formula 7-30
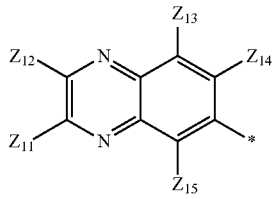
Formula 7-31
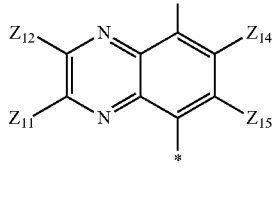
Formula 7-32
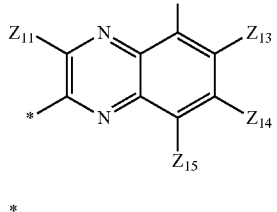
Formula 7-33
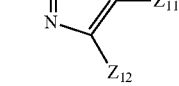
Formula 7-34
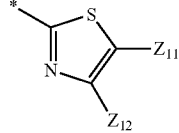
Formula 7-35

-continued

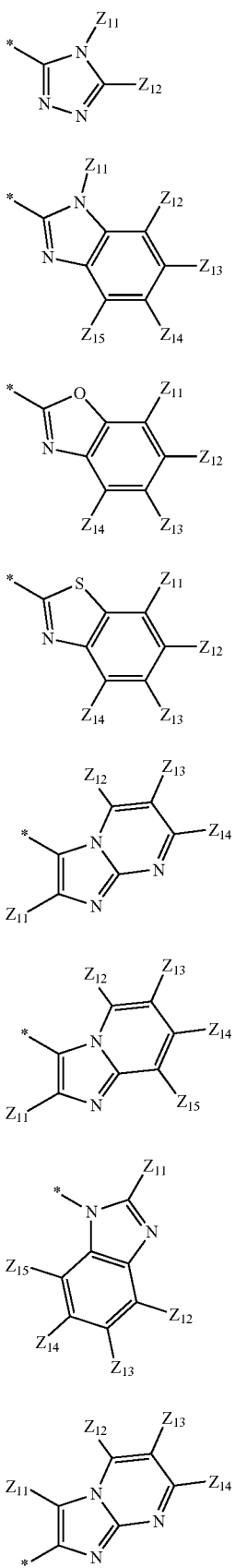

-continued

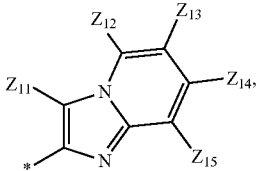

wherein in Formulae 7-1 to 7-44, $Z_{11}$ to $Z_{16}$ are each independently selected from hydrogen, deuterium, —F, —Cl, —Br, —I, a hydroxyl group, a cyano group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, phenanthridinyl, acridinyl, phenanthrolinyl, phenazinyl, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group and an imidazopyrimidinyl group, and * indicates a binding site to a neighboring atom.

12. The condensed cyclic compound of claim 1, wherein when at least one of b12, b13, b22 and b23 is not 0, $R_{12}$, $R_{13}$, $R_{22}$, and $R_{23}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a triazolyl group, and a triazinyl group.

13. The condensed cyclic compound of claim 1, wherein the condensed cyclic compound is represented by Formula 1-1;
a11 is selected from 0, 1, and 2; and
each of a12 and a13 is 0.

14. The condensed cyclic compound of claim 1, wherein the condensed cyclic compound is represented by any one selected from Formulae 1-1A and 1-1B:

Formula 1-1A
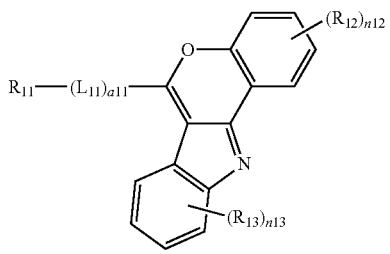

Formula 1-1B
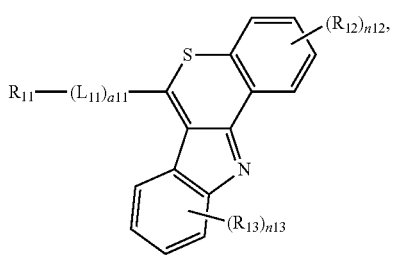

wherein descriptions of $L_{11}$, a11, $R_{11}$ to $R_{13}$, n12, and n13 in Formulae 1-1A and 1-1B are the same as in Formula 1-1.

15. The condensed cyclic compound of claim 1, wherein the condensed cyclic compound is represented by any one selected from Formulae 1-1C and 1-1D:

Formula 1-1C
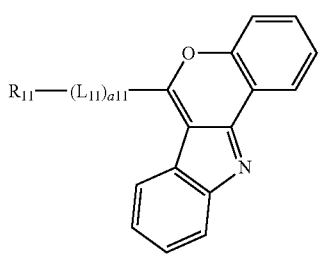

Formula 1-1D
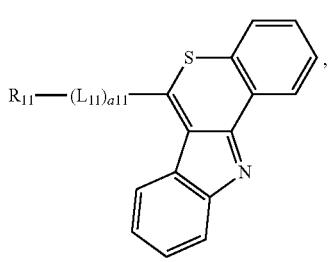

wherein $L_{11}$ in Formulae 1-1C and 1-1D is represented by one selected from Formulae 4-1 to 4-8:

Formula 4-1
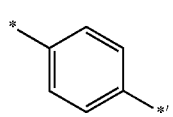

Formula 4-2
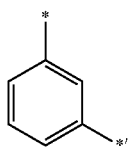

Formula 4-3
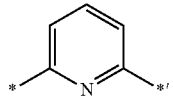

Formula 4-4
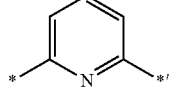

Formula 4-5
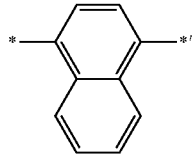

Formula 4-6
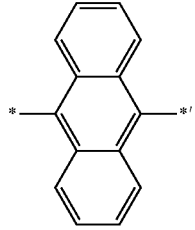

Formula 4-7
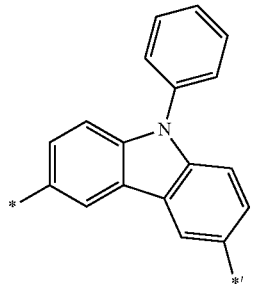

Formula 4-8
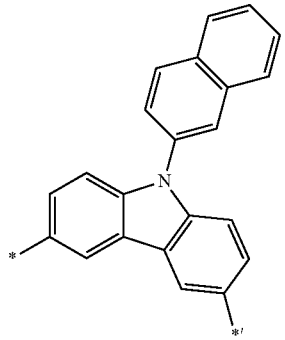

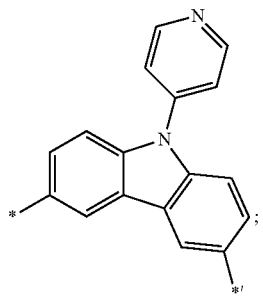

a11 is selected from 0, 1, and 2, and when a11 is 2, 2 $L_{11}(s)$ are identical to or different from each other; and $R_{11}$ is represented by one selected from Formulae 6-1 to 6-42:

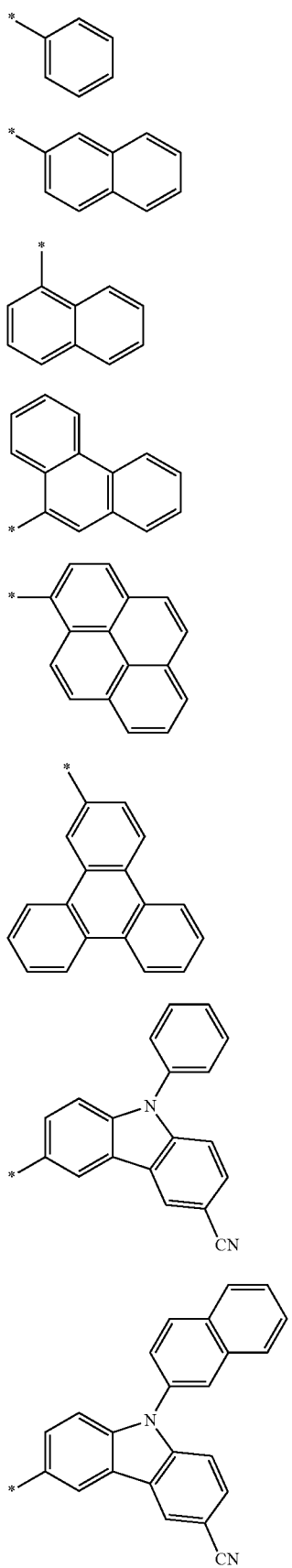
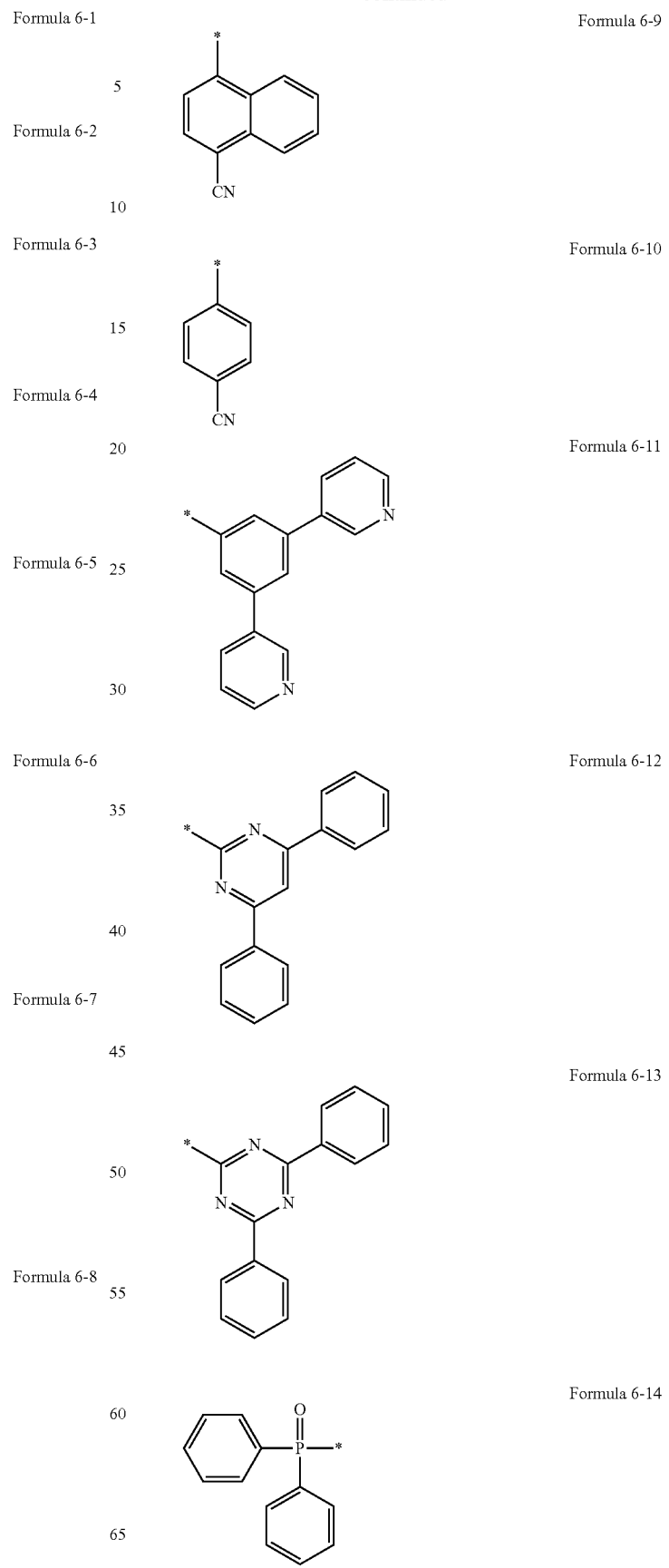

Formula 6-15

Formula 6-16

Formula 6-17

Formula 6-18

Formula 6-19

Formula 6-20

Formula 6-21

Formula 6-22

Formula 6-23

Formula 6-24

Formula 6-25

Formula 6-26

Formula 6-27

Formula 6-28

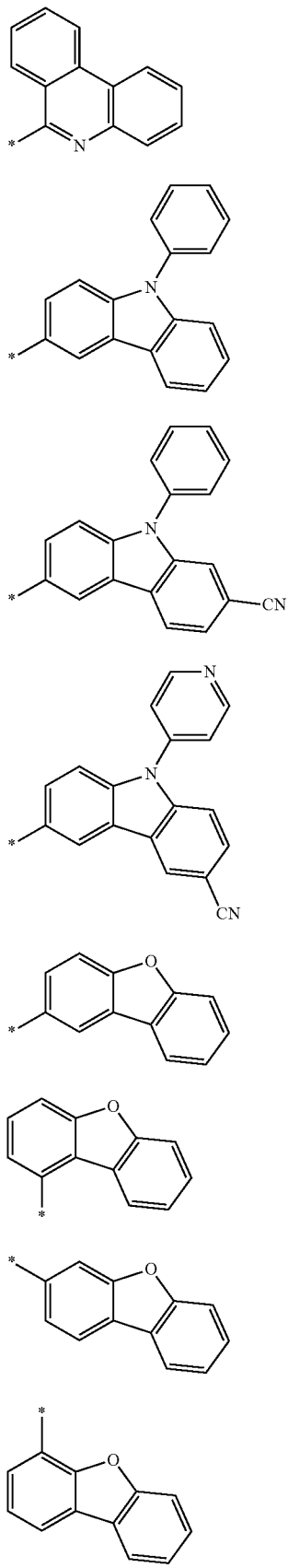
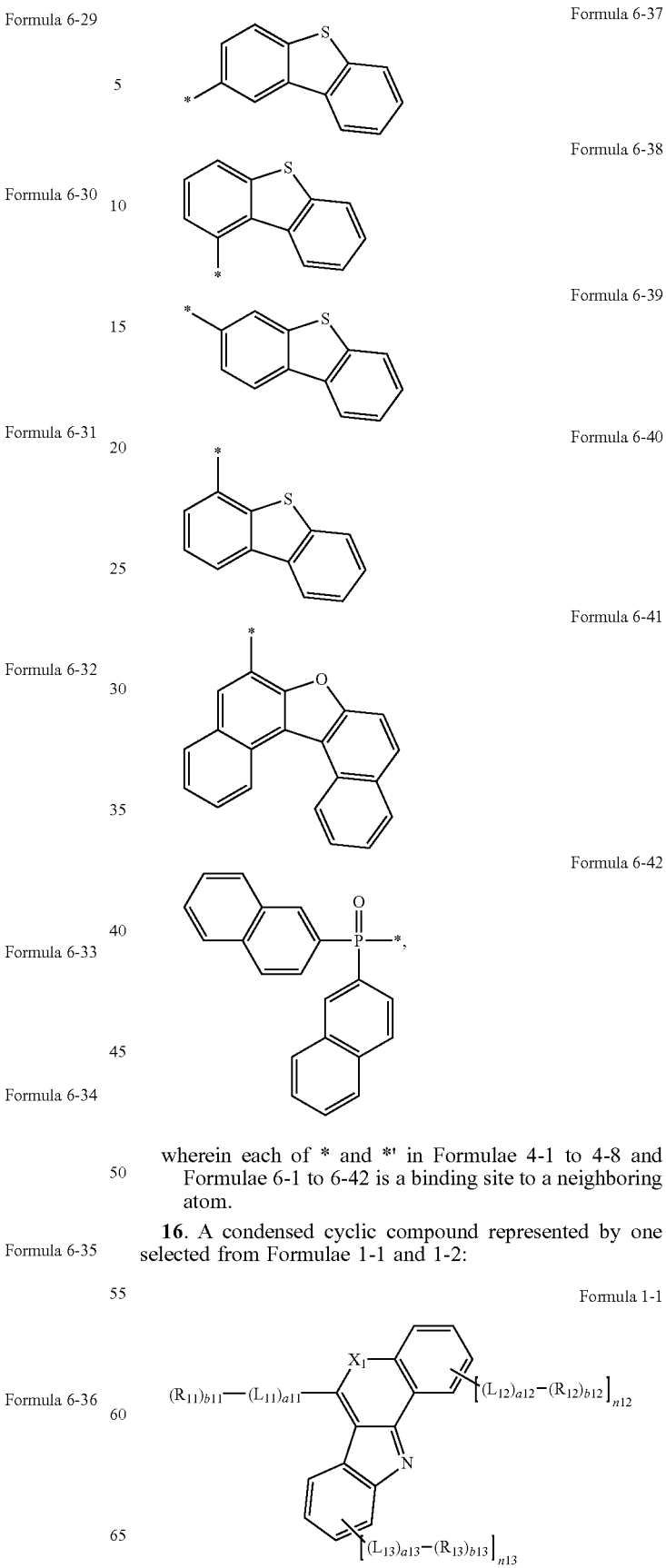
wherein each of * and *' in Formulae 4-1 to 4-8 and Formulae 6-1 to 6-42 is a binding site to a neighboring atom.
16. A condensed cyclic compound represented by one selected from Formulae 1-1 and 1-2:

Formula 1-2

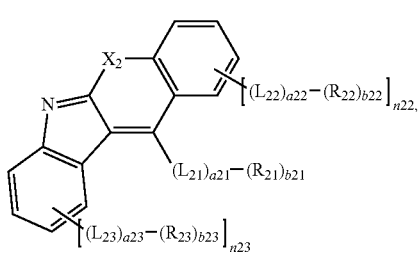

wherein in Formulae 1-1 and 1-2, $X_1$ and $X_2$ are each independently O or S;

$L_{11}$ to $L_{13}$ and $L_{21}$ to $L_{23}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a11 to a13 and a21 to a23 are each independently selected from 0, 1, 2, and 3, and when a11 is 2 or more, 2 or more $L_{11}$(s) are identical to or different from each other, and when a12 is 2 or more, 2 or more $L_{12}$(s) are identical to or different from each other, and when a13 is 2 or more, 2 or more $L_{13}$(s) are identical to or different from each other, and when a21 is 2 or more, 2 or more $L_{21}$(s) are identical to or different from each other, and when a22 is 2 or more, 2 or more $L_{22}$(s) are identical to or different from each other, and when a23 is 2 or more, 2 or more $L_{23}$(s) are identical to or different from each other;

$R_{11}$ to $R_{13}$ and $R_{21}$ to $R_{23}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —P(=O)($Q_4$)($Q_5$), —S(=O)($Q_6$), and —S(=O)$_2$($Q_7$);

b11 to b13 and b21 to b23 are each independently selected from 0, 1, 2, and 3, and when b11 is 2 or more, 2 or more $R_{11}$(s) are identical to or different from each other, and when b12 is 2 or more, 2 or more $R_{12}$(s) are identical to or different from each other, and when b13 is 2 or more, 2 or more $R_{13}$(s) are identical to or different from each other, and when b21 is 2 or more, 2 or more $R_{21}$(s) are identical to or different from each other, and when b22 is 2 or more, 2 or more $R_{22}$(s) are identical to or different from each other, and when b23 is 2 or more, 2 or more $R_{23}$(s) are identical to or different from each other; and n12, n13, n22, and n23 are each independently selected from 0, 1, 2, 3, and 4, wherein the compound represented by Formula 1-1 is neither Compound A nor Compound B, and the compound represented by Formula 1-2 is not Compound D:

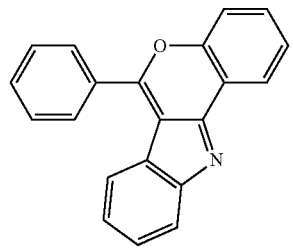

Compound A

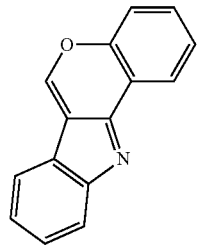

Compound B

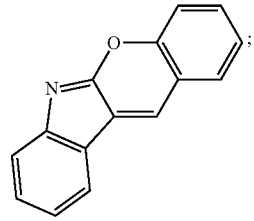

Compound D and wherein at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group and substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —B($Q_{14}$)($Q_{15}$), and —N($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —B($Q_{24}$)($Q_{25}$), and —N($Q_{26}$)($Q_{27}$); and —Si($Q_{31}$)($Q_{32}$)($Q_{33}$), —B($Q_{34}$)($Q_{35}$), and —N($Q_{36}$)($Q_{37}$), wherein $Q_1$ to $Q_7$, $Q_{11}$ to $Q_{17}$, $Q_{21}$ to $Q_{27}$ and $Q_{31}$ to $Q_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, wherein the condensed cyclic compound is one selected from Compounds 1 to 110:

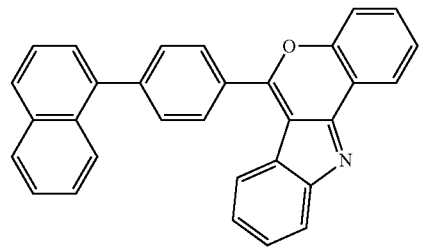

1

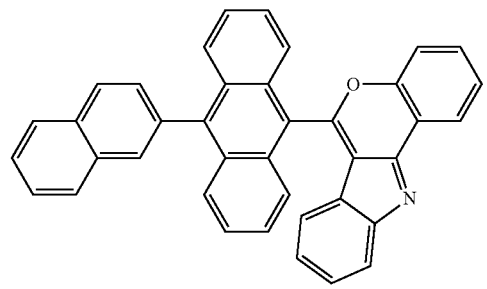

2

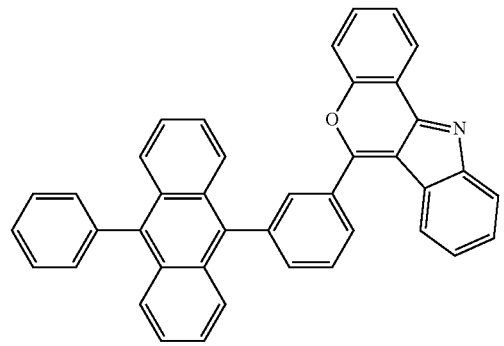

3

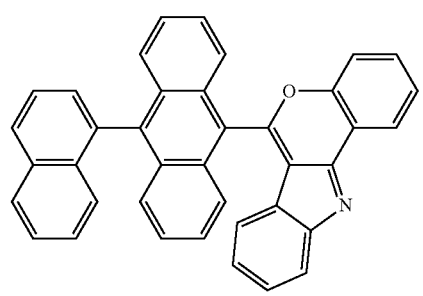

4

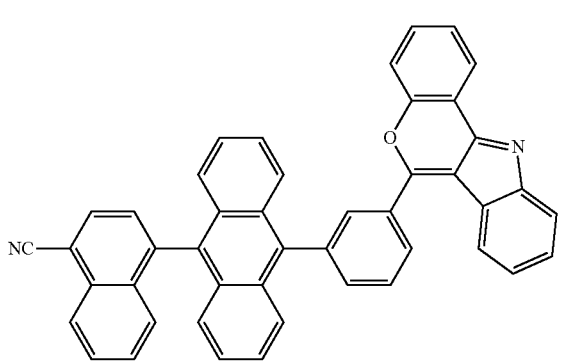

5

193
-continued
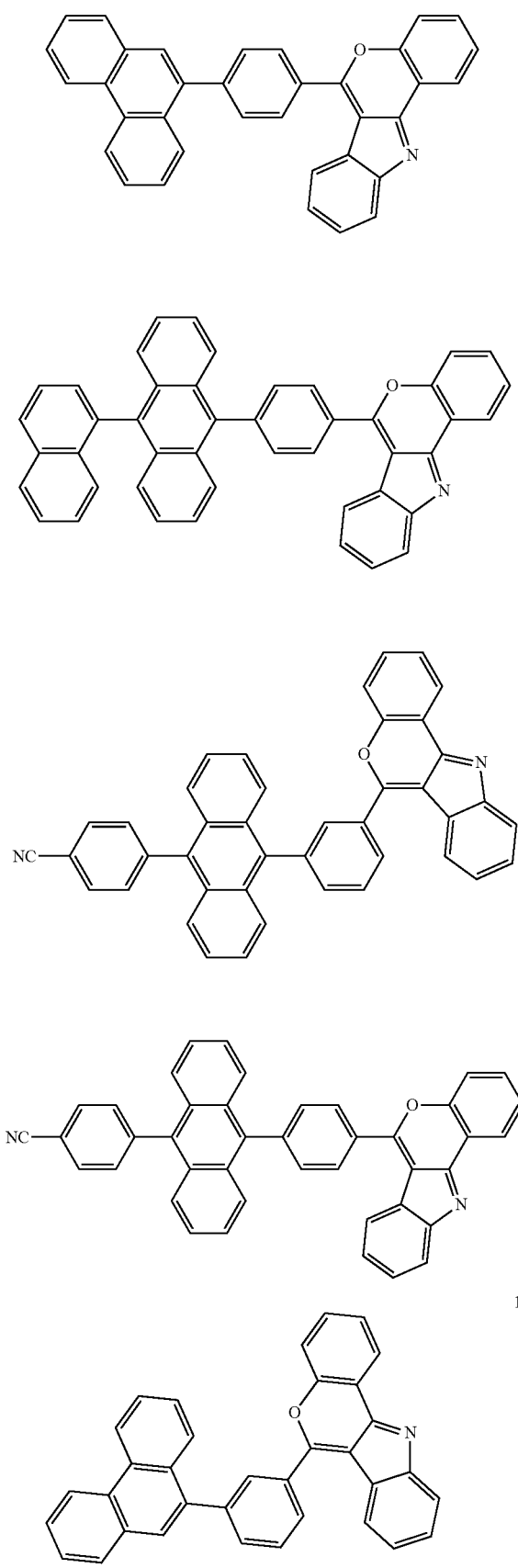
194
-continued
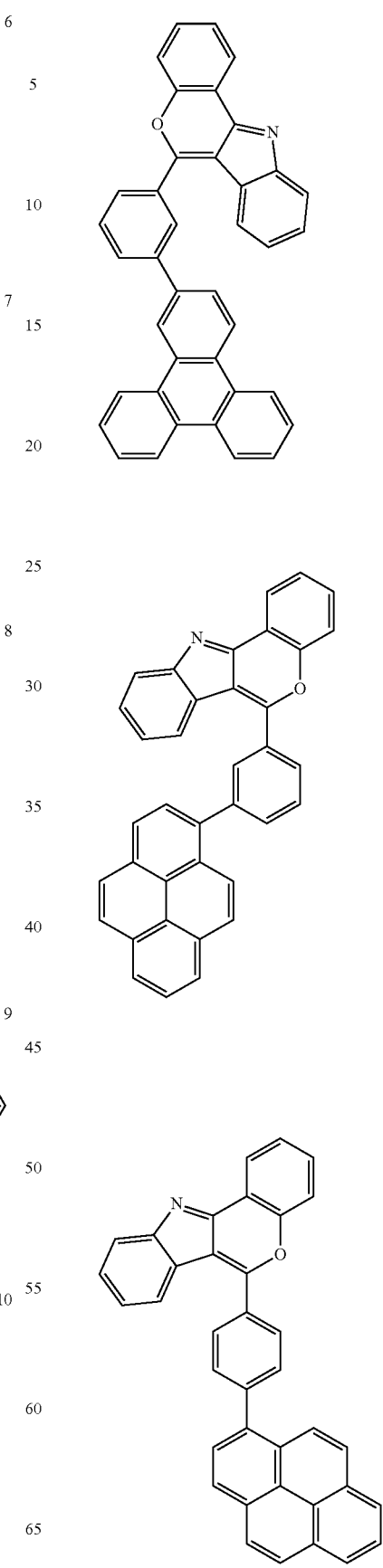

195
-continued
11
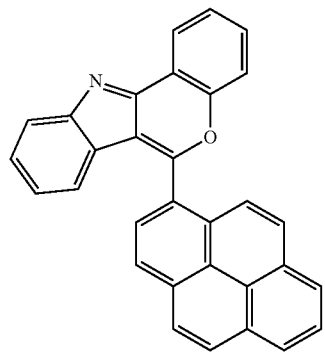
12
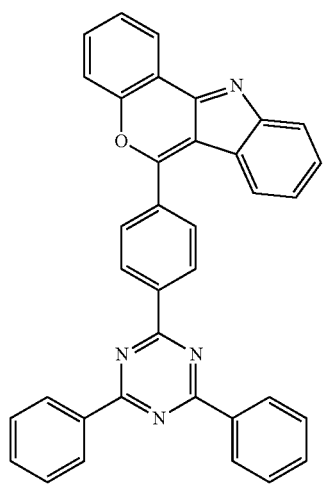
13
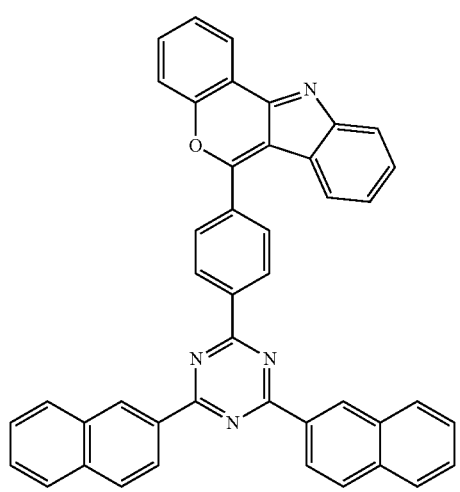
196
-continued
14
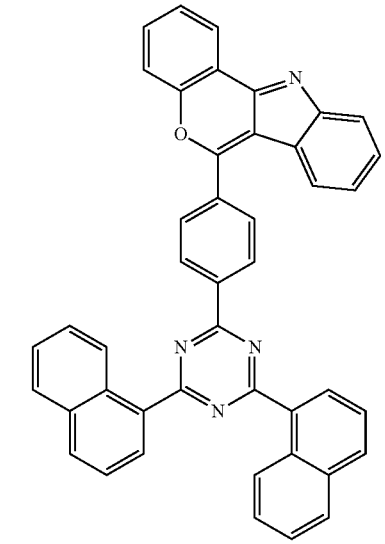
15
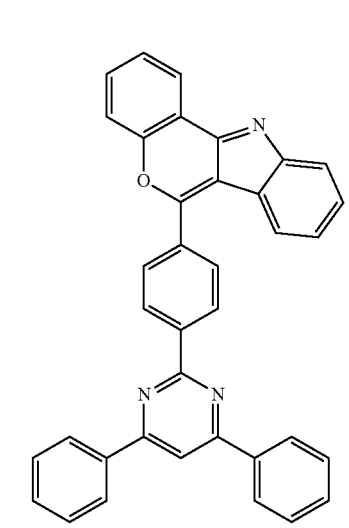
16
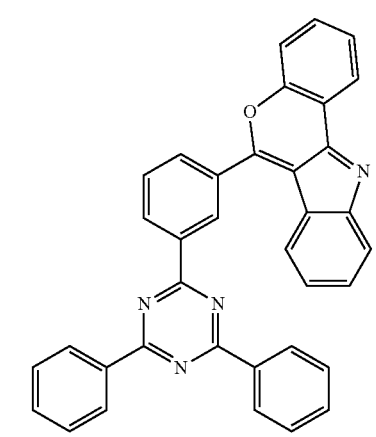

17
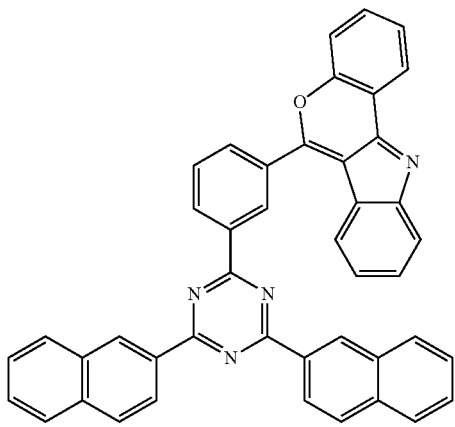
18
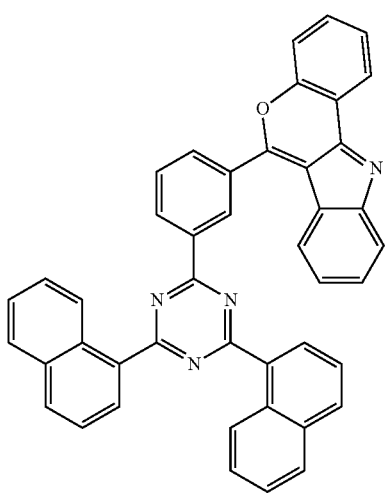
19
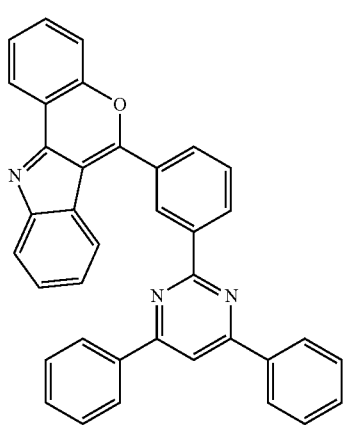
20
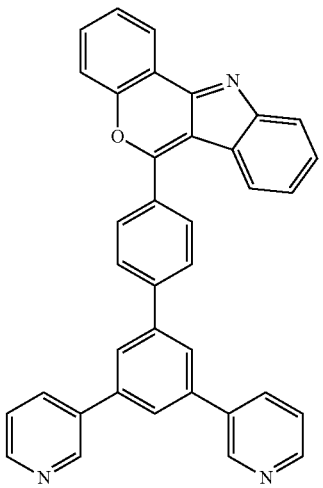
21
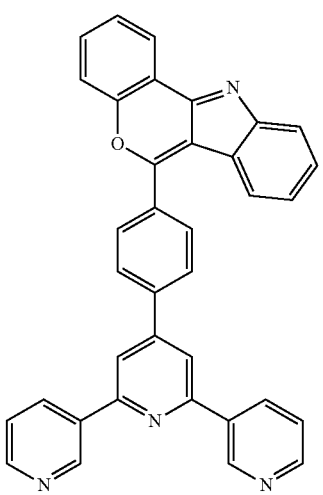
22
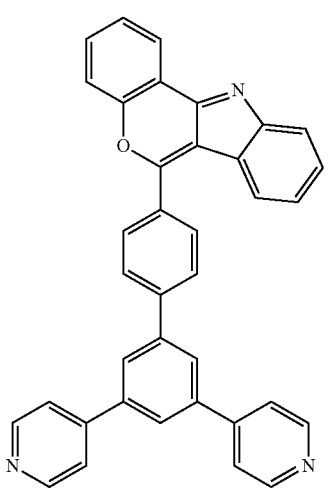

23
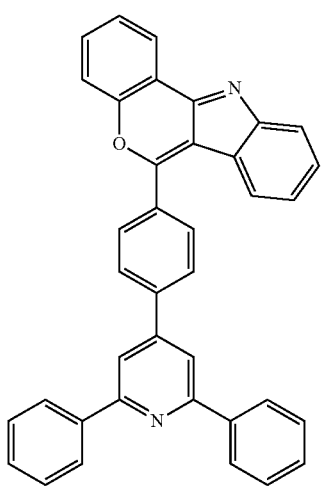
24
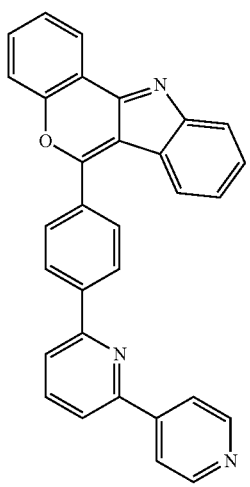
25
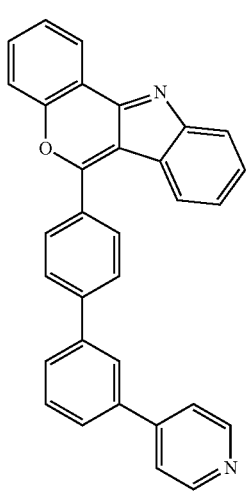
26
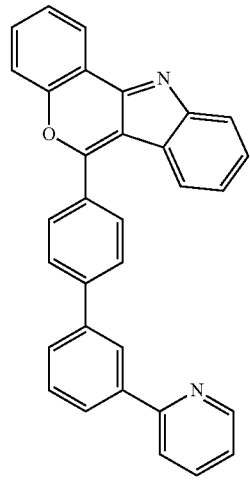
27
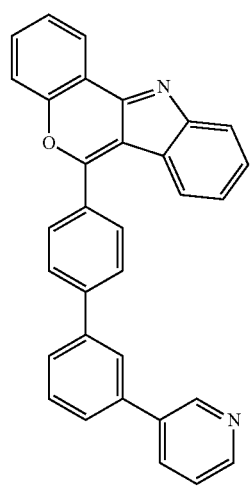
28
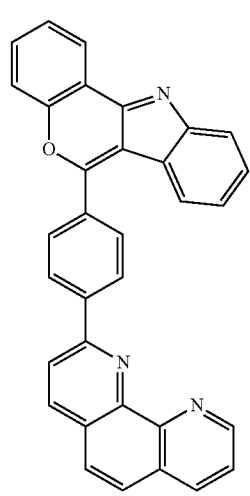

29
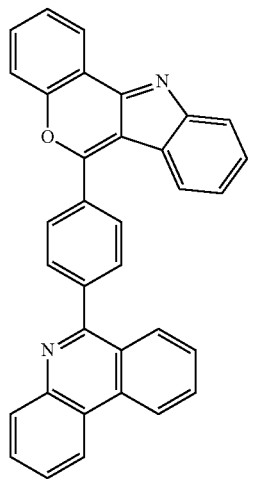
30
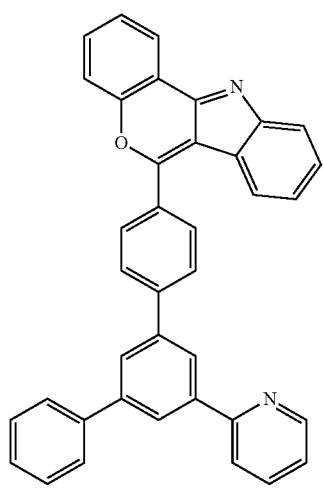
31
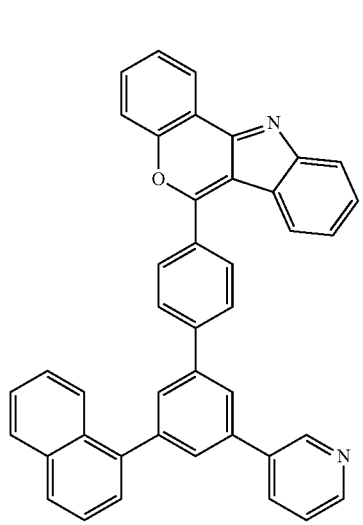
32
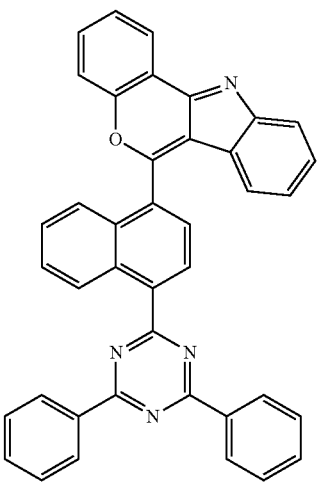
33
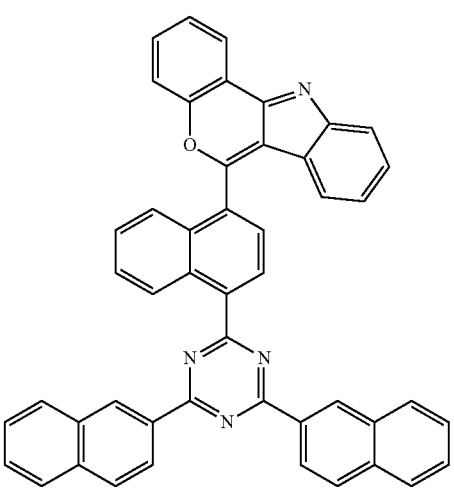
34
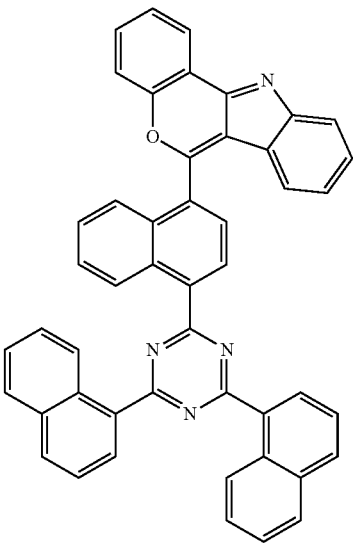

203
-continued
| 35 | 38 |
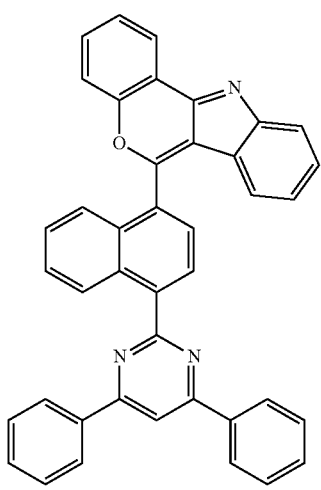
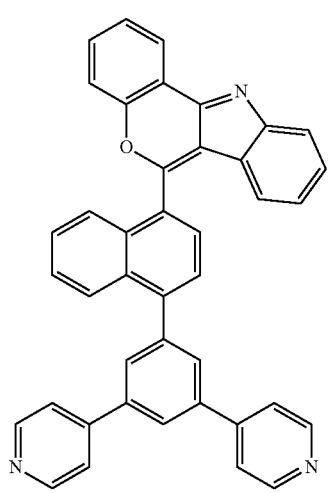
| 36 | 39 |
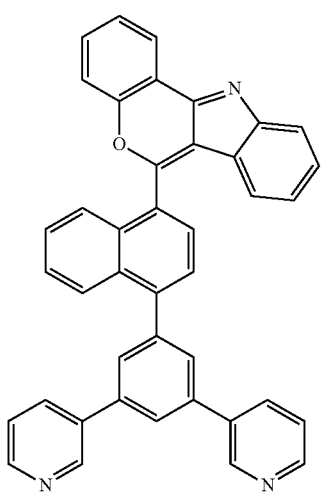
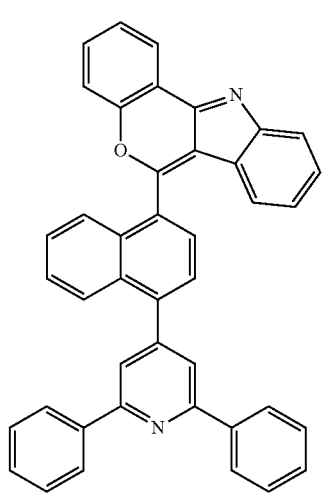
| 37 | 40 |
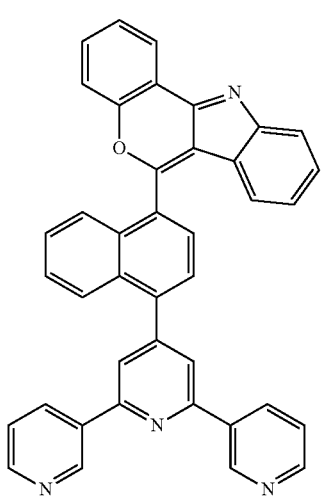
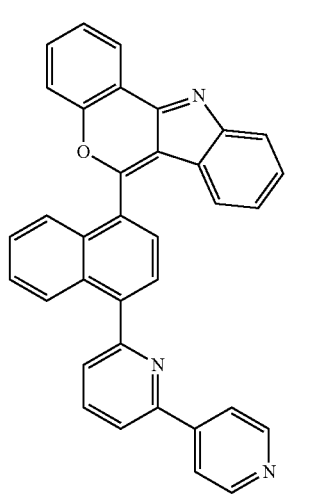

205
-continued
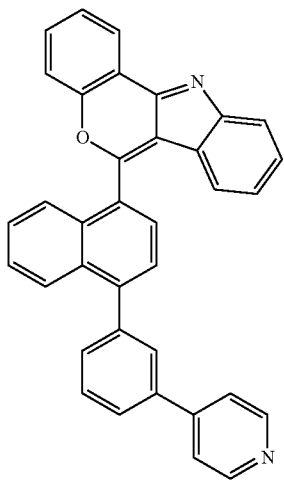
41
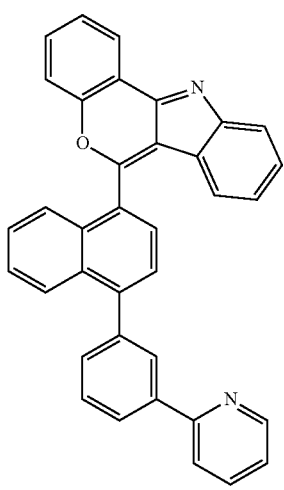
42
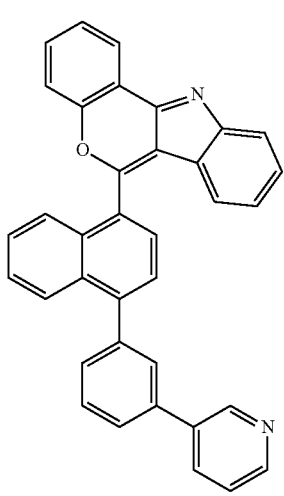
43
206
-continued
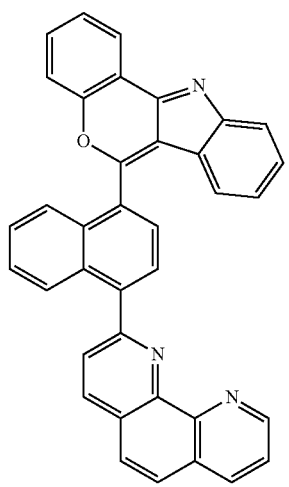
44
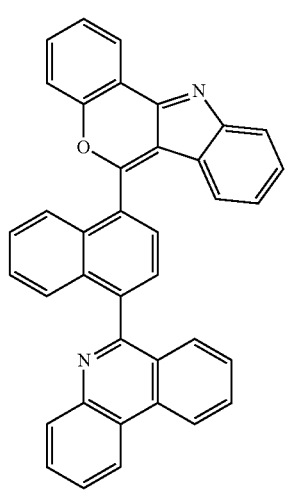
45
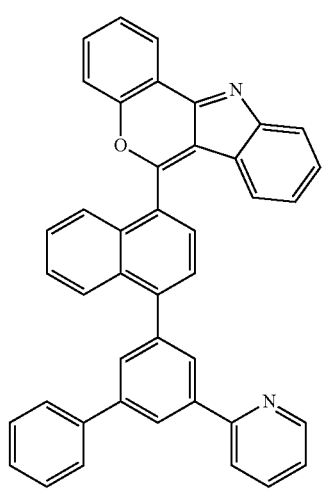
46

47
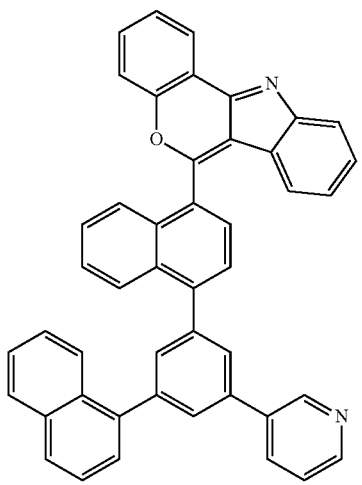
48
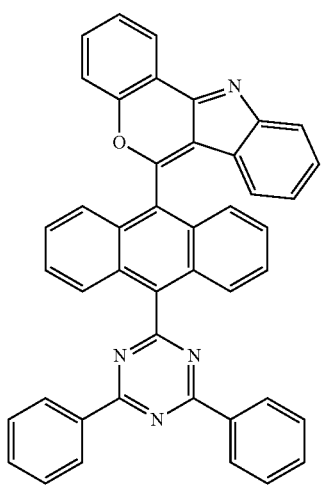
49
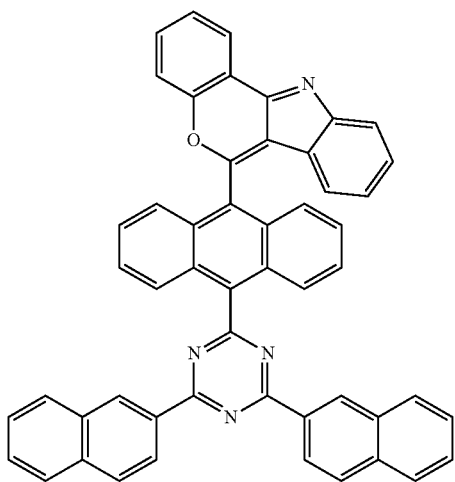
50
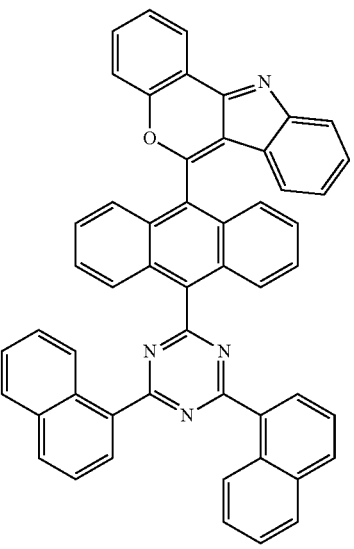
51
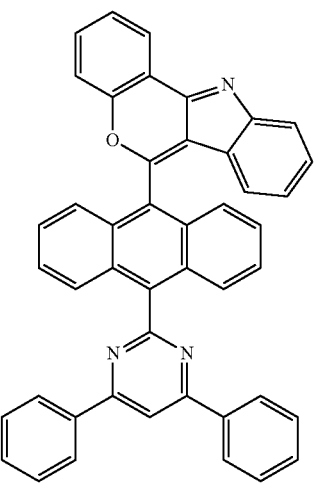
52
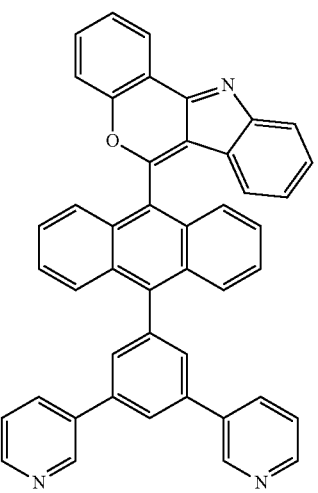

53
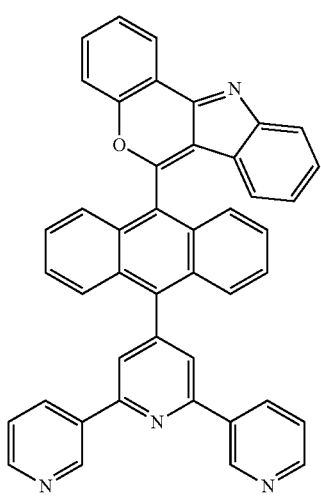
54
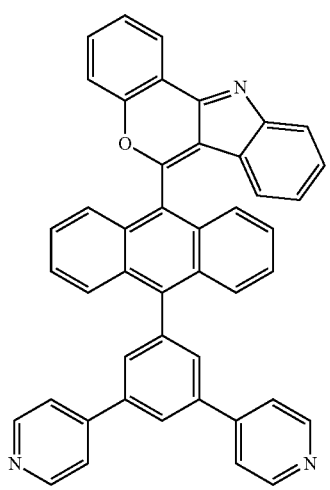
55
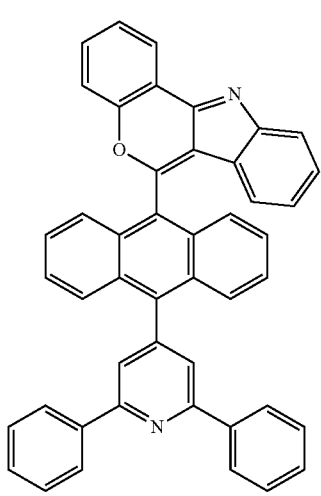
56
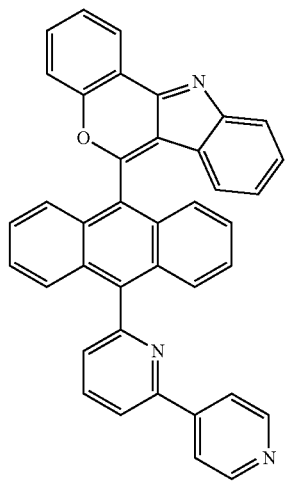
57
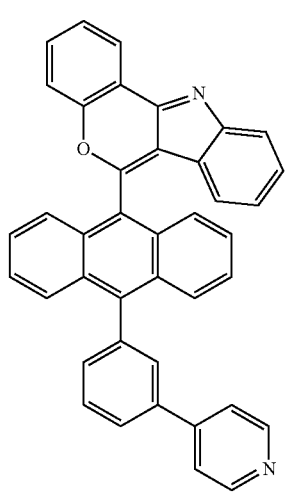
58
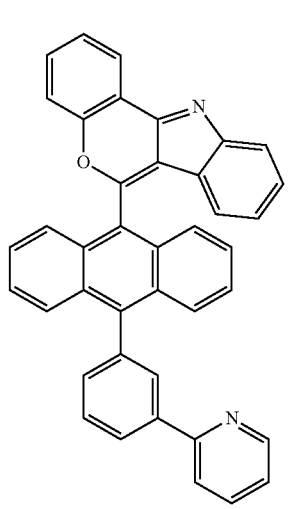

211
-continued
59
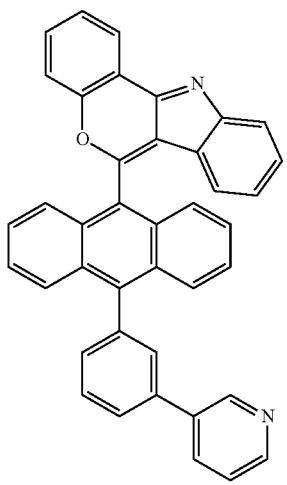
60
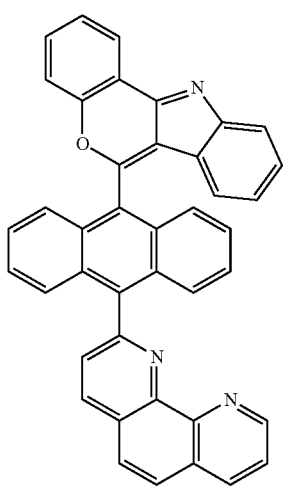
61
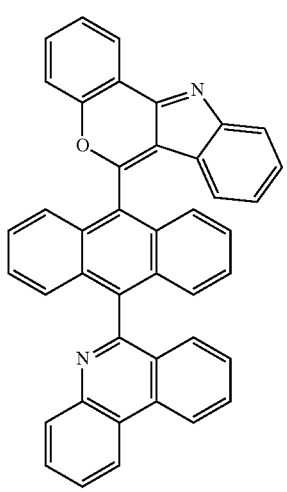
212
-continued
62
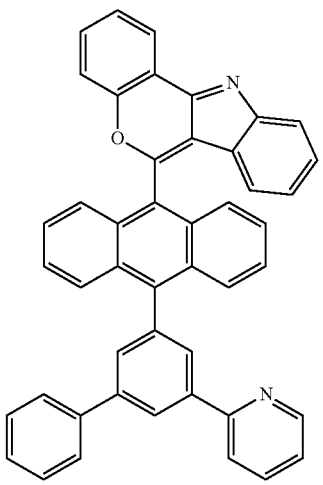
63
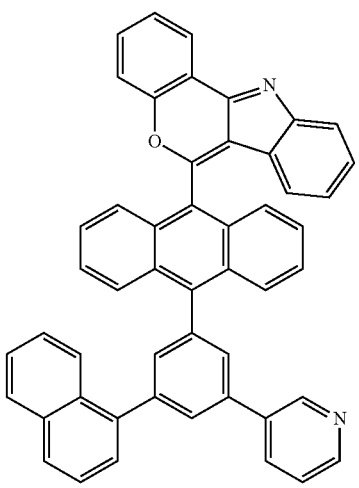
64
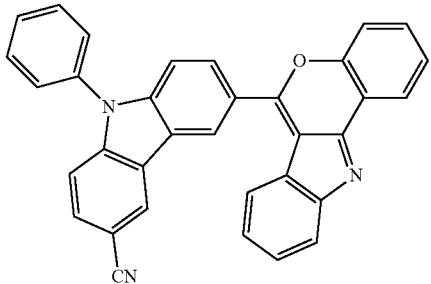
65
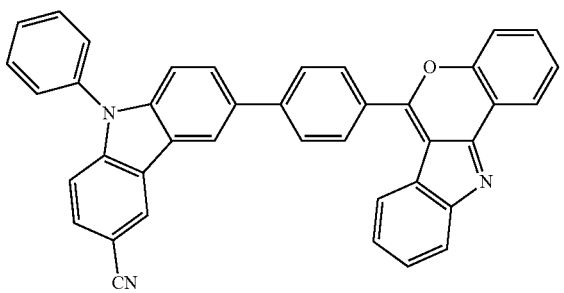

66
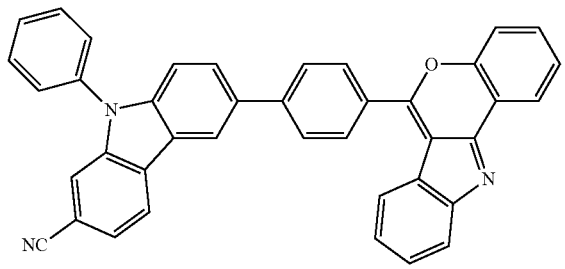
71
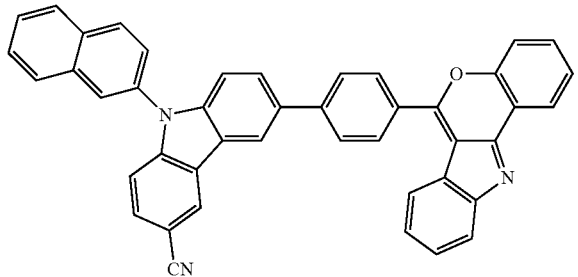
67
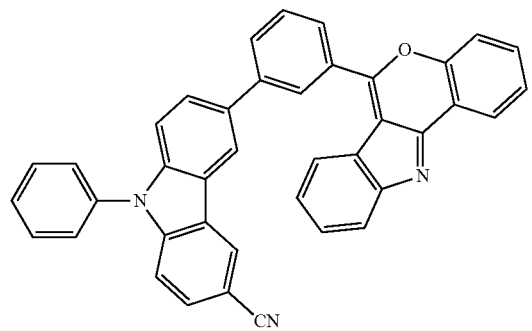
72
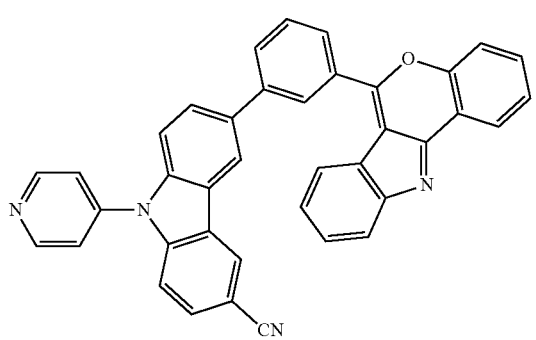
68
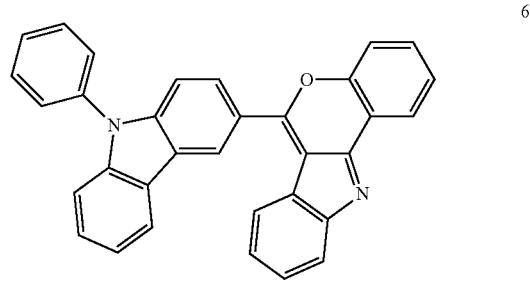
73
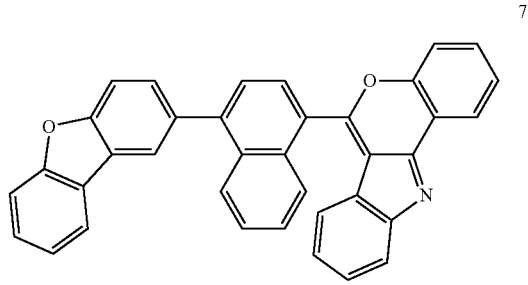
69
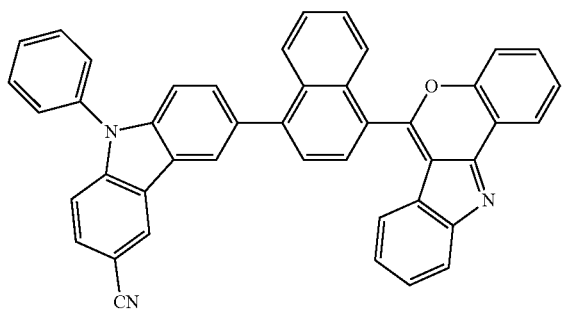
74
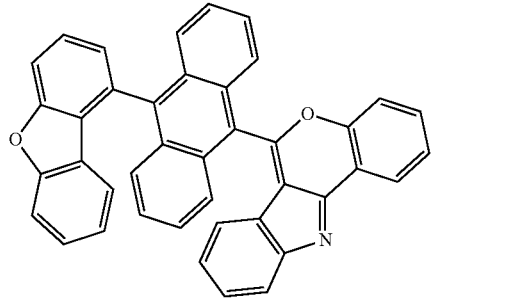
70
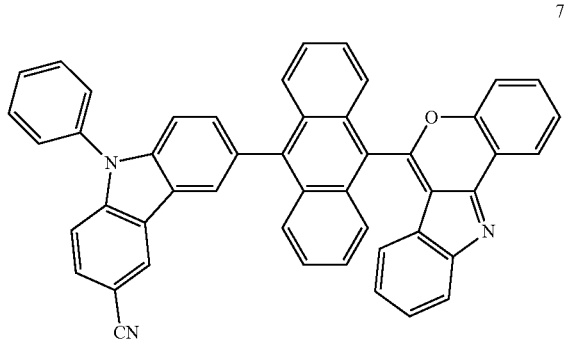
75
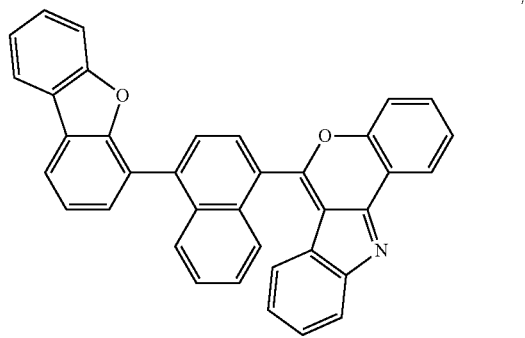

76
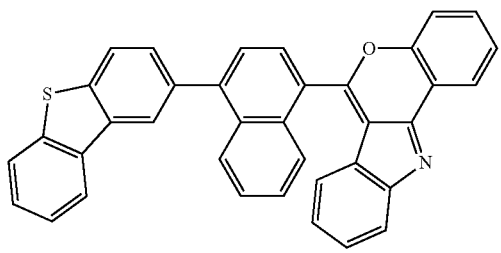
77
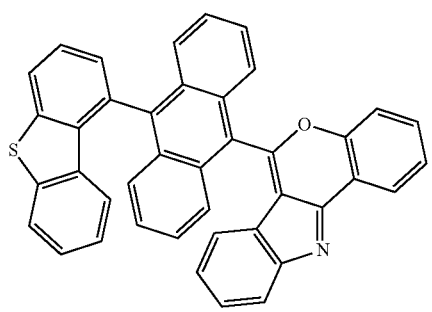
78
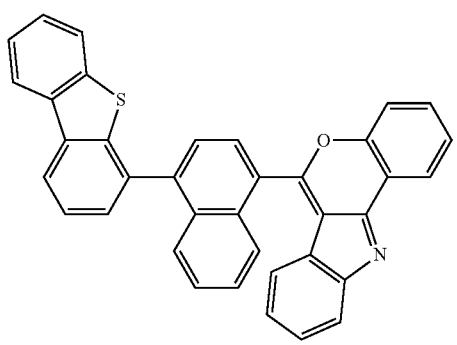
79
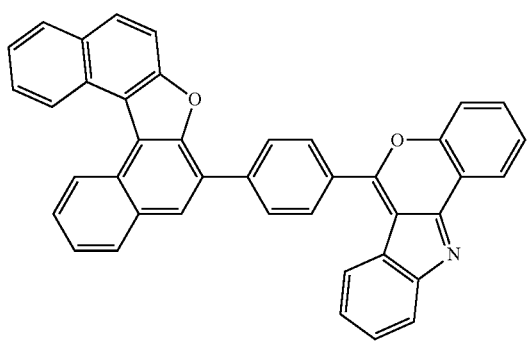
80
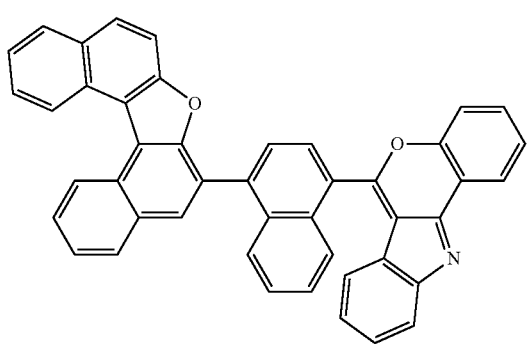
81
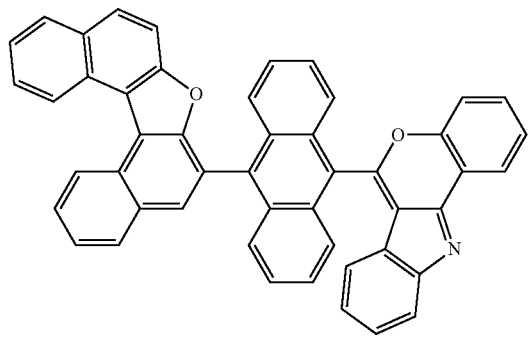
82
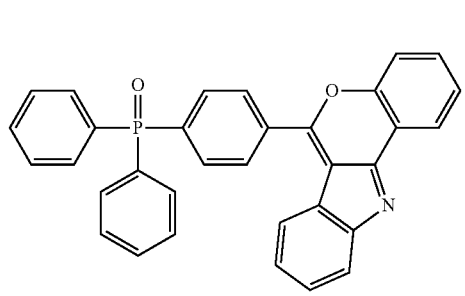
83
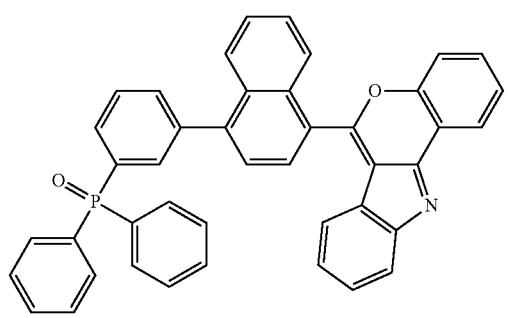
84
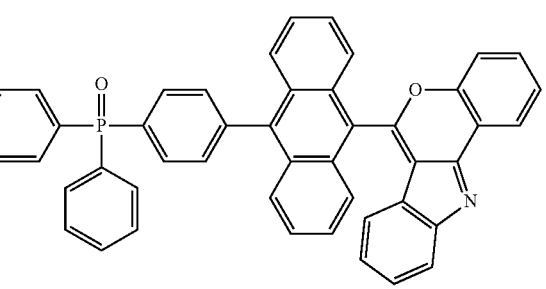
85
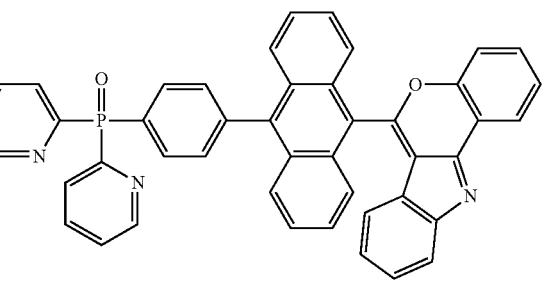

86
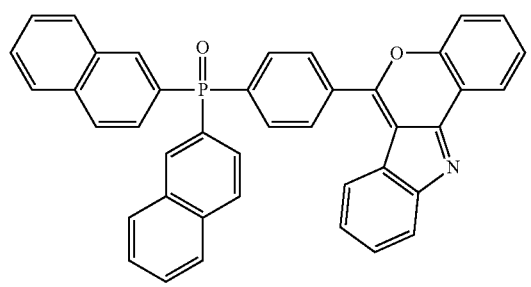
87
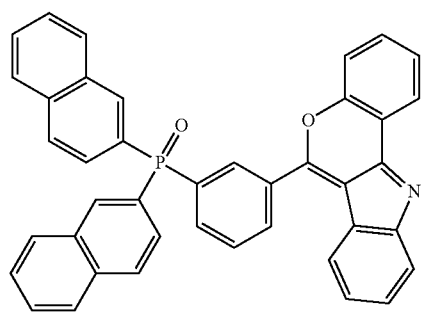
88
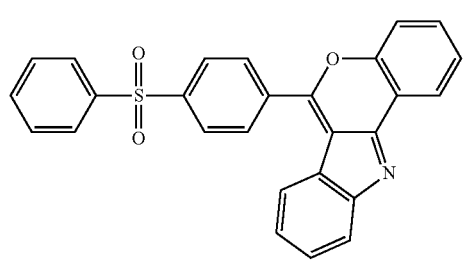
89
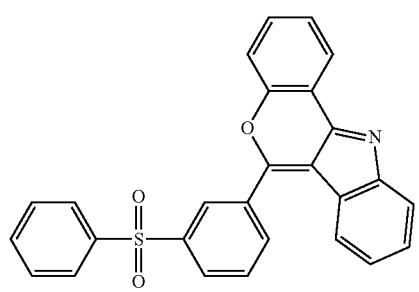
90
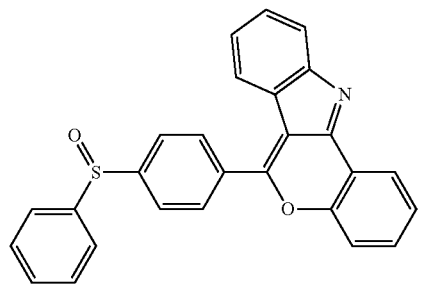
91
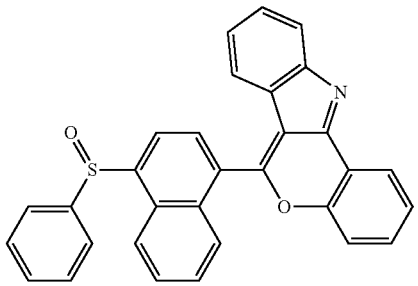
92
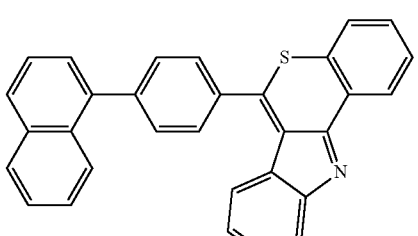
93
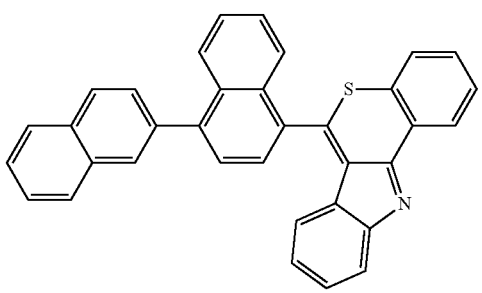
94
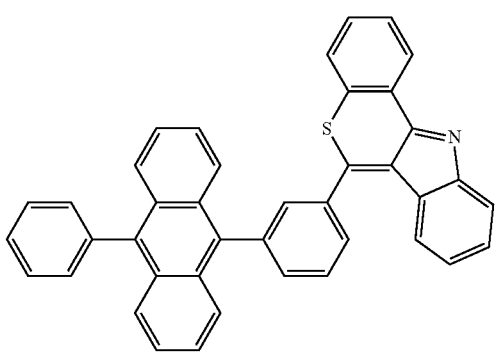
95
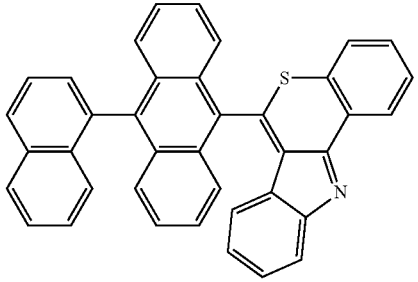

-continued
96
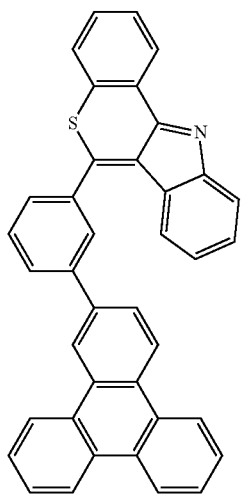
97
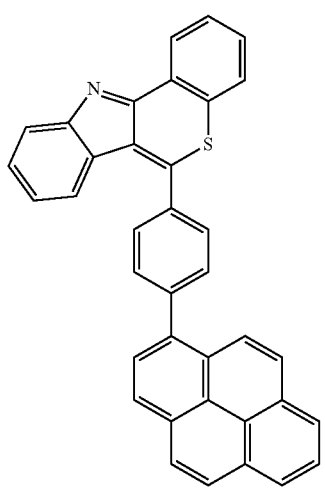
98
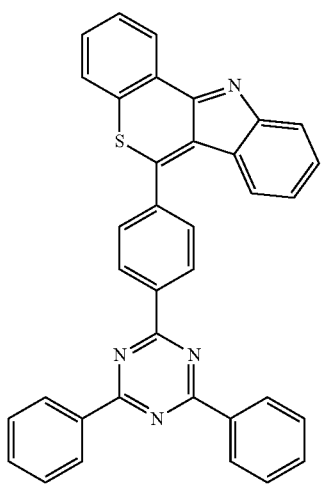
-continued
99
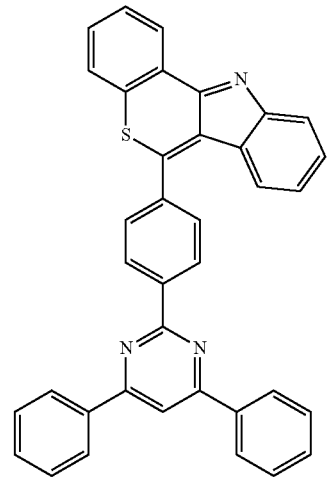
100
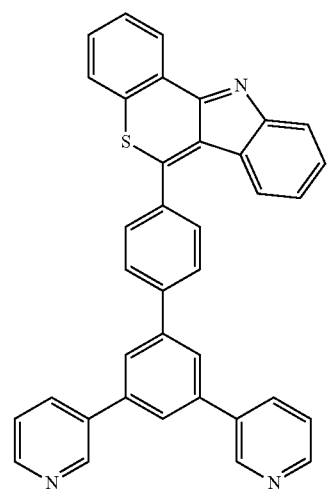
101
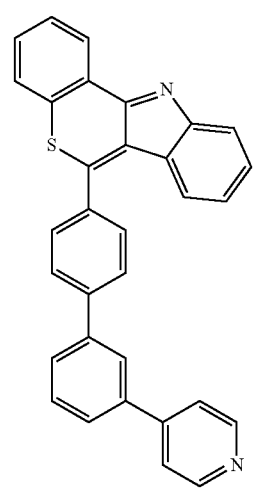

221
-continued
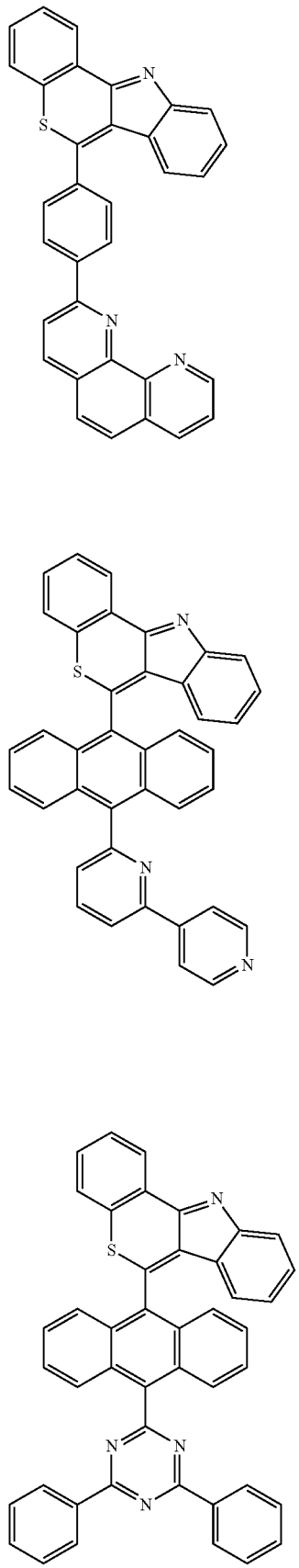
222
-continued
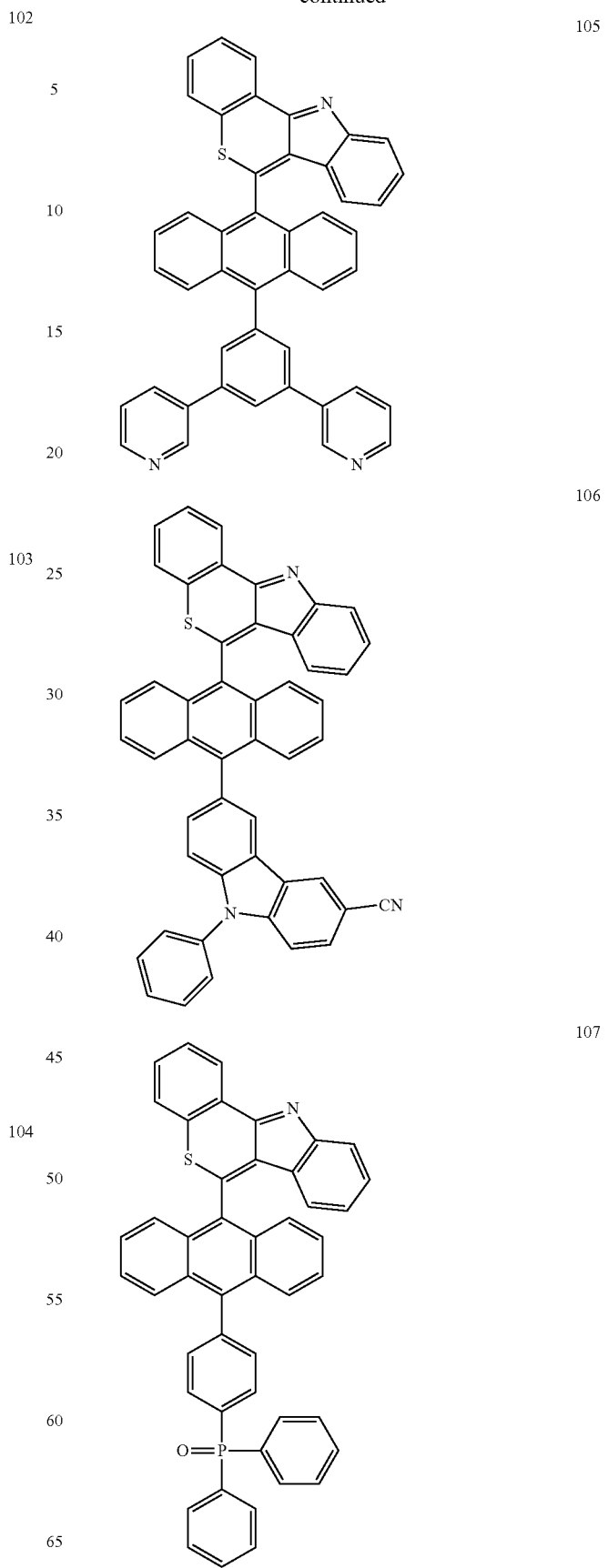

108

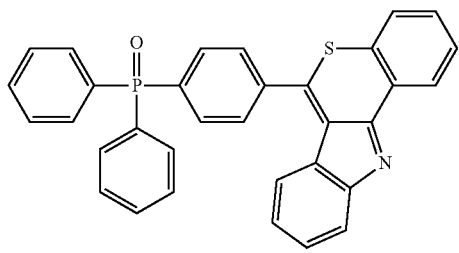

109

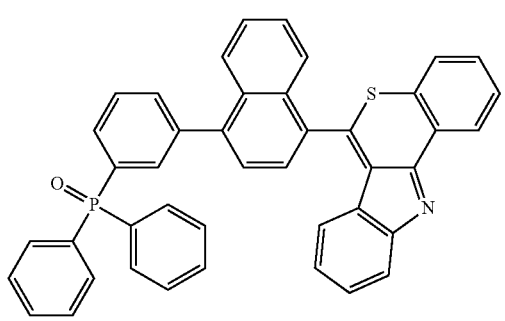

110

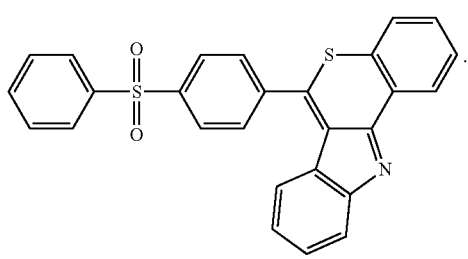

17. An organic light-emitting device comprising:

a first electrode;

a second electrode facing the first electrode; and an organic layer between the first electrode and the second electrode, the organic layer comprising an emission layer, wherein the organic layer comprises at least one condensed cyclic compound represented by one selected from Formulae 1-1 and 1-2:

Formula 1-1

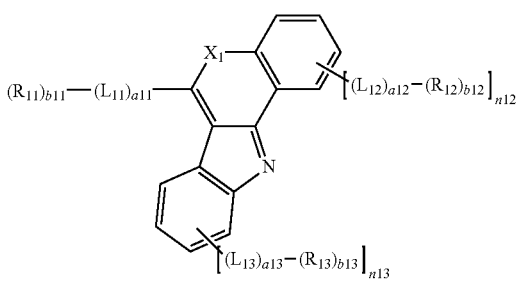

Formula 1-2

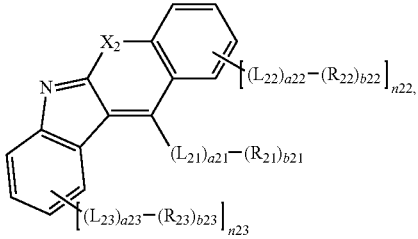

wherein in Formulae 1-1 and 1-2, $X_1$ and $X_2$ are each independently O or S;

$L_{11}$ to $L_{13}$ and $L_{21}$ to $L_{23}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a11 to a13 and a21 to a23 are each independently selected from 0, 1, 2, and 3, and when a11 is 2 or more, 2 or more $L_{11}$(s) are identical to or different from each other, and when a12 is 2 or more, 2 or more $L_{12}$(s) are identical to or different from each other, and when a13 is 2 or more, 2 or more $L_{13}$(s) are identical to or different from each other, and when a21 is 2 or more, 2 or more $L_{21}$(s) are identical to or different from each other, and when a22 is 2 or more, 2 or more $L_{22}$(s) are identical to or different from each other, and when a23 is 2 or more, 2 or more $L_{23}$(s) are identical to or different from each other;

$R_{11}$ to $R_{13}$ and $R_{21}$ to $R_{23}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, —P(=O)$(Q_4)(Q_5)$, —S(=O)$(Q_6)$, and —S(=O)$_2(Q_7)$;

b11 to b13 and b21 to b23 are each independently selected from 0, 1, 2, and 3, and when b11 is 2 or more, 2 or more $R_{11}$(s) are identical to or different from each other, and when b12 is 2 or more, 2 or more $R_{12}$(s) are identical to or different from each other, and when b13 is 2 or more, 2 or more $R_{13}$(s) are identical to or different from each other, and when b21 is 2 or more, 2 or more $R_{21}$(s) are identical to or different from each other, and when b22 is 2 or more, 2 or more $R_{22}$(s) are identical to or different from each other, and when b23 is 2 or more, 2 or more $R_{23}$(s) are identical to or different from each other; and n12, n13, n22, and n23 are each independently selected from 0, 1, 2, 3, and 4, wherein the compound represented by Formula 1-1 is neither Compound A nor Compound B, and the compound represented by Formula 1-2 is not Compound D:

Compound A

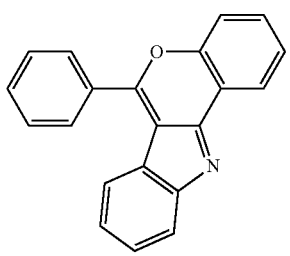

Compound B

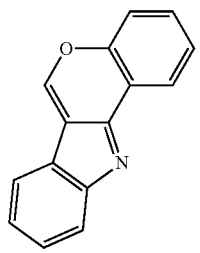

Compound D

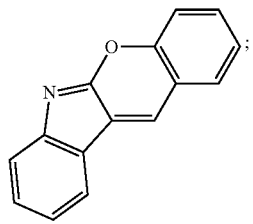

and wherein at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group and substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —B($Q_{14}$)($Q_{15}$), and —N($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —B($Q_{24}$)($Q_{25}$), and —N($Q_{26}$)($Q_{27}$); and —Si($Q_{31}$)($Q_{32}$)($Q_{33}$), —B($Q_{34}$)($Q_{35}$), and —N($Q_{36}$)($Q_{37}$), wherein $Q_1$ to $Q_7$, $Q_{11}$ to $Q_{17}$, $Q_{21}$ to $Q_{27}$ and $Q_{31}$ to $Q_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

18. The organic light-emitting device of claim 17, wherein
the first electrode is an anode,
the second electrode is a cathode,
the organic layer comprises:
i) a hole transport region between the first electrode and the emission layer, the hole transport region comprising at least one selected from a hole injection layer, a hole transport layer, a buffer layer, and an electron blocking layer and
ii) an electron transport region between the emission layer and the second electrode, the electron transport region comprising at least one selected from a hole blocking layer, an electron transport layer, and an electron injection layer.

19. The organic light-emitting device of claim 18, wherein the electron transport region comprises the condensed cyclic compound represented by one selected from Formulae 1-1 and 1-2.

20. The organic light-emitting device of claim 18, wherein the emission layer comprises the condensed cyclic compound represented by one selected from Formulae 1-1 and 1-2.

* * * * *